US008710298B2

(12) United States Patent
Hannah et al.

(10) Patent No.: US 8,710,298 B2
(45) Date of Patent: Apr. 29, 2014

(54) HEAT STABLE VARIANTS OF PLANT ADENOSINE DIPHOSPHATE GLUCOSE PYROPHOSPHORYLASE SMALL SUBUNIT

(75) Inventors: L. Curtis Hannah, Gainesville, FL (US); Carla R. Lyerly Linebarger, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1807 days.

(21) Appl. No.: 10/569,000

(22) PCT Filed: Aug. 18, 2004

(86) PCT No.: PCT/US2004/026965
§ 371 (c)(1),
(2), (4) Date: Oct. 10, 2006

(87) PCT Pub. No.: WO2005/019425
PCT Pub. Date: Mar. 3, 2005

(65) Prior Publication Data
US 2011/0167519 A1     Jul. 7, 2011

Related U.S. Application Data

(60) Provisional application No. 60/496,188, filed on Aug. 18, 2003.

(51) Int. Cl.
*C12N 15/82* (2006.01)
*A01H 5/00* (2006.01)
*C07H 21/04* (2006.01)

(52) U.S. Cl.
USPC ........... 800/289; 800/260; 800/270; 800/275; 800/276; 800/278; 800/295; 800/298; 800/320.1; 536/23.6; 536/23.2; 536/23.1; 536/22.1

(58) Field of Classification Search
None
See application file for complete search history.

(56) References Cited

U.S. PATENT DOCUMENTS

| 5,034,322 | A | 7/1991 | Rogers et al. | |
|---|---|---|---|---|
| 5,106,739 | A | 4/1992 | Comai et al. | |
| 5,589,618 | A | 12/1996 | Hannah et al. | |
| 5,625,136 | A | 4/1997 | Koziel et al. | |
| 5,650,557 | A | 7/1997 | Hannah et al. | |
| 5,872,216 | A | 2/1999 | Hannah et al. | |
| 6,069,300 | A | 5/2000 | Hannah et al. | |
| 6,403,863 | B1 | 6/2002 | Hannah et al. | |
| 2003/0150027 | A1* | 8/2003 | Giroux | 800/287 |
| 2009/0260101 | A1* | 10/2009 | Hannah et al. | 800/278 |
| 2011/0078821 | A1* | 3/2011 | Hannah et al. | 800/284 |

FOREIGN PATENT DOCUMENTS

| WO | WO 98/10082 | 3/1998 | | |
|---|---|---|---|---|
| WO | WO 98/22601 | 5/1998 | | |
| WO | WO 99/58698 | * 11/1999 | ............ C12N 15/82 |
| WO | WO 01/64928 | 9/2001 | | |
| WO | WO 02/072784 | 9/2002 | | |
| WO | WO 03/070901 | 8/2003 | | |

OTHER PUBLICATIONS

Ballicora et al. Adenosine 5'-diphosphate-glucose pyrophosphorylase from the potato tuber. (1995) Plant Physiology; vol. 109; pp. 245-251.*
Ballicora et al. Heat stability of the potato tuber ADP-glucose pyrophosphorylase: role of Cys residue 12 in the small subunit. (1999) Biochem. Biophys. Res. Comm.; vol. 257; pp. 782-786.*
Greene et al. Enhanced stability of maize endosperm ADP-glucose pryophosphorylase is gained through mutants that alter subunit interactions. (1998) PNAS; vol. 95; pp. 13342-13347.*
Ainsworth, C. et al. "Adenosine diphosphate glucose pyrophosphorylase genes in wheat: differential expression and gene mapping" *Planta*, 1995, pp. 1-10, vol. 197.
Altschul, S.F. et al. "Gapped BLAST and PSI-BLAST: A new generation of protein database search programs" *Nucleic Acids Research*, 1997, pp. 3389-3402, vol. 25, No. 17.
Anderson, J.M. et al. "The encoded primary sequence of a rice seed ADP-glucose pyrophosphorylase subunit and its homology to the bacterial enzyme" *J. Biol.Chem.*, 1989, pp. 12238-12242, vol. 264, No. 21.
Anderson, J.M. et al. "Molecular characterization of the gene encoding a rice endosperm-specific ADP-glucose pyrophosphorylase subunit and its developmental pattern of transcription" *Gene*, 1991, pp. 199-205, vol. 97.
Badu-Apraku, B. et al. "Effect of temperature during grain filling on whole plant and grain yield in maize" *Can. J. Plant. Sci.*, 1983, pp. 357-363, vol. 63.
Bae, J.M. et al. "Cloning and characterization of the *Brittle*-2 gene of maize" *Maydica*, 1990, pp. 317-322, vol. 35.

(Continued)

Primary Examiner — Cathy Kingdon Worley
(74) Attorney, Agent, or Firm — Saliwanchik, Lloyd & Eisenschenk

(57) ABSTRACT

The subject invention concerns polynucleotides encoding a small subunit of plant AGP having one or more mutations in the amino acid sequence wherein the mutation confers increased heat stability to the expressed AGP enzyme. Mutations in the N-terminus of the small subunit of heat labile plant AGP results in AGP enzymes that are significantly more heat stable compared to wild type AGP in that the mutant AGP retains significant levels of enzymatic activity following exposure to heat treatment. In one embodiment, the polynucleotide encodes a mutant small subunit of maize AGP. The subject invention also concerns methods for providing a plant with increased resistance to heat conditions. Plants with heat labile AGP can be transformed with a polynucleotide of the present invention. The subject invention also concerns these transformed plants and transgenic progeny thereof. The subject invention also concerns mutant polypeptides encoded by polynucleotides of the present invention.

57 Claims, 3 Drawing Sheets

(56) References Cited

OTHER PUBLICATIONS

Ballicora, M.A. et al. "Adenosine 5'-diphosphate-glucose pyrophosphorylase from the potato tuber" *Plant Physiol.*, 1995, pp. 245-251, vol. 109.

Ballicora, M.A. et al. "Heat stability of the potato tuber ADP-glucose pyrophosphorylase: role of Cys residue 12 in the small subunit" *Biochemical and Biophysical Research Communications*, 1999, pp. 782-786, vol. 257.

Beltz, G. A. et al. "Isolation of multigene families and determination of homologies by filter hybridization methods" *Methods of Enzymology*, 1983, pp. 266-285, vol. 100, Academic Press, New York.

Brave, M.R. et al. "Identification and molecular characterization of *Shrunken-2* cDNA clones of maize" *Plant Cell*, Jun. 1990, pp. 581-588, vol. 2.

Burger, B.T. et al. "Relative turnover numbers of maize endosperm and potato tuber ADP-glucose pyrophosphorylases in the absence and presence of 3-phosphoglyceric acid" *Planta*, 2003, pp. 449-456, vol. 217.

Chang, J. "Corn yield in relation to photoperiod, night temperature, and solar radiation" *Agricul. Metero.*, 1981, pp. 253-262, vol. 24.

Cheikh, N. et al. "Heat stress effects on sink activity of developing maize kernels grown in vitro" *Physiologia. Plantarum*, 1995, pp. 59-66, vol. 95.

Clancy, M. et al. "Splicing of the maize *Sh*1 first intron is essential for enhancement of gene expression, and a T-rich motif increases expression without affecting splicing" *Plant Physiology*, Oct. 2002, pp. 918-929, vol. 130, No. 2.

Conroy, J.P. et al. "Influence of rising atmospheric $CO_2$ concentrations and temperature on growth, yield and grain quality of cereal crops" *Aust. J. Plant Physiol.*, 1994, pp. 741-758, vol. 21.

Copeland, L. et al. "Purification of spinach leaf ADPglucose pyrophosphorylase" *Plant Physiol.*, 1981, pp. 996-1001, vol. 68, No. 5.

De Boer, H. A. et al. "The *tac* promoter: a functional hybrid derived from the *trp* and *lac* promoters" *Proc. Natl. Acad. Sci.USA*, Jan. 1983, pp. 21-25, vol. 80, No. 1.

Denyer, K. et al. "The effect of high temperature on starch synthesis and the activity of starch synthase" *Aust. J. Plant Physiol.*, 1994, pp. 783-789, vol. 21, No. 6.

Dickinson, D.B. et al. "Presence of ADP-glucose pyrophosphorylase in shrunken-2 and brittle-2 mutants of maize endosperm" *Plant Physiol.*, 1969, pp. 1058-1062, vol. 44, No. 7.

Duke, E.R. et al. "Effects of heat stress on enzyme activities and transcript levels in developing maize kernels grown in culture" *Environ. Exp. Bot.*, 1996, pp. 199-208, vol. 36, No. 2.

Giroux, M.J. et al. "A single gene mutation that increases maize seed weight" *Proc. Natl. Acad. Sci.*, Jun. 1996, pp. 5824-5829, vol. 93.

Greene, T.W. et al. "Mutagenesis of the potato ADP-glucose pyrophosphorylase and characterization of an allosteric mutant defective in 3-phosphoglycerate activation" *Proc. Natl. Acad. Sci.*, Feb. 1996, pp. 1509-1513, vol. 93.

Greene, T. W. et al. "Aspartic Acid 413 is important for the normal allosteric functioning of ADP-glucose pyrophosphorylase" *Plant Physiol.*, 1996, pp. 1315-1320, vol. 112.

Greene, T.W. et al. "Enhanced stability of maize endosperm ADP-glucose pyrophosphorylase is gained through mutants that alter subunit interactions" *Proc. Natl. Acad. Sci. USA*, 1998, pp. 13342-13347, vol. 95.

Hannah, L. C. et al. "Multiple forms of maize endosperm ADP-glucose pyrophosphorylase and their control by shrunken-2 and brittle-2" *Genetics*, Aug. 1980, pp. 961-970, vol. 95.

Hannah, L.C. "Starch synthesis in the maize Seed" In *Advances in Cellular and Molecular Biology of Plants*, vol. 4, *Cellular and Molecular Biology of Plant Seed Development*, edited by B.A. Larkins and I. K. Vasil, 1997, pp. 375-405, Kluwer Academic Publishers, Dordrecht, The Netherlands.

Hannah, L.C. et al. "Characterization of adenosine diphosphate glucose pyrophosphorylases from developing maize seeds" *Plant Physiol.*, 1975, pp. 297-302, vol. 55.

Hannah, L.C. et al. "Characterization of ADP-glucose pyrophosphorylase from *Shrunken-2* and *Brittle-2* mutants of maize" *Biochem. Genet.*, 1976, pp. 547-560, vol. 14, Nos. 7/8.

Hannah, L. C. et al. "Maize genes encoding the small subunit of ADP-glucose pyrophosphorylase" *Plant Physiol.*, Sep. 2001, pp. 173-183, vol. 127.

Hawker, J.S. et al. "High temperature affects the activity of enzymes in the committed pathway of starch synthesis in developing wheat endosperm" *Aust. J. Plant Physiol.*, 1993, pp. 197-209, vol. 20.

Horton, R.M. et al. "Gene splicing by overlap extension" in *Methods of Enzymology: Recombinant DNA*, Part H, 1993, pp. 270-279, vol. 217, part H, Academic Press, New York.

Hunter, R. B. et al. "Effects of photoperiod and temperature on vegetative and reproductive growth of a maize (*Zea mays*) hybrid" *Can. J. Plant Sci.*, Oct. 1977, pp. 1127-1133, vol. 57.

Inglesias, A. et al. "Expression of the potato tuber ADP-glucose pyrophosphorylase in *Escherichia coli*" *J. Biol. Chem.*, Jan. 1993, pp. 1081-1086, vol. 268, No. 2.

Jenner, C.F. "Starch synthesis in the kernel of wheat under high temperature conditions" *Aust. J. Plant Physiol.*, 1994, pp. 791-806, vol. 21.

Jenner, C.F. et al. "Thermal characteristics of soluble starch synthase from wheat endosperm" *Aust. J. Plant Physiol.*, 1995, pp. 703-709, vol. 22.

Jones, R.J. et al. "Temperature effects on in vitro kernel development of maize" *Crop Science*, 1981, pp. 761-766, vol. 21.

Jones, R.J. et al. "Thermal environment during endosperm cell division and grain filling in maize: effects on kernel growth and development in vitro" *Crop Science*, 1984, pp. 133-137, vol. 24.

Karlin, S. et al. "Methods for assessing the statistical significance of molecular sequence features by using general scoring schemes" *Proc. Natl. Acad. Sci. USA*, Mar. 1990, pp. 2264-2268, vol. 87.

Karlin, S. et al. "Applications and statistics for multiple high-scoring segments in molecular sequences" *Proc. Natl. Acad. Sci. USA*, Jun. 1993, pp. 5873-5877, vol. 90.

Keeling, P.L. et al. "Elevated temperature reduces starch deposition in wheat endosperm by reducing the activity of soluble starch synthase" *Planta.*, 1993, pp. 342-348, vol. 191.

Kleczkowski, L.A. et al. "Insensitivity of barley endosperm ADP-glucose pyrophosphorylase to 3-phosphoglycerate and orthophosphate regulation" *Plant Physiol.*, 1993, pp. 179-186, vol. 101, No. 1.

Lin, T-P. et al. "A starch deficient mutant of *Arabidopsis thaliana* with low ADPglucose pyrophosphorylase activity lacks one of the two subunits of the enzyme" *Plant Physiol.*, 1988, pp. 1175-1181, vol. 88.

Maniatis, T. et al. "Nuclease *Bal*31" *Molecular Cloning: A Laboratory Manual*, 1982, Cold Spring Harbor Laboratory, Cold Spring Harbor, New York.

Morell, M. et al. "Affinity labeling of the allosteric activator site(s) of spinach leaf ADP-glucose pyrophosphorylase" *Journal of Biological Chemistry*, Jan. 1988, pp. 633-637, vol. 263, No. 2.

Muller-Rober, B.T. et al. "One of two different ADP-glucose pyrophosphorylase genes from potato responds strongly to elevated levels of sucrose" *Mol. Gen. Genet.*, 1990, pp. 136-146, vol. 224.

Nakata, P.A. et al. "Comparison of the primary sequences of two potato tuber ADP-glucose pyrophosphorylase subunits" *Plant Mol. Biol.*, 1991, pp. 1089-1093, vol. 17.

Okita, T.W. et al. "The subunit structure of potato tuber ADPglucose pyrophosphorylase" *Plant Physiol.*, 1990, pp. 785-790, vol. 93, No. 2.

Okita, T.W. et al. "Engineering plant starches by the generation of modified plant biosynthetic enzymes" in *Engineering Crops for Industrial End Uses*, 1996, Portland Press Ltd., London.

Olive, M.R. et al. "Isolation and Nucleotide Sequences of cDNA clones encoding ADP-glucose pyrophosphorylase polypeptides from wheat leaf and endosperm" *Plant Mol. Biol.*, 1989, pp. 525-538, vol. 12.

Ou-Lee, T-M. et al. "Effect of increased temperature in apical regions of maize ears on starch-synthesis enzymes and accumulation of sugars and starch" *Plant Physiol.*, 1985, pp. 852-855, vol. 79.

Preiss, J. "Bacterial glycogen synthesis and its regulation" *Ann. Rev. Microbiol.*, 1984, pp. 419-458, vol. 38.

(56) References Cited

OTHER PUBLICATIONS

Preiss, J. et al. "Molecular biology and regulatory aspects of glycogen biosynthesis in bacteria" *Progress in Nuc. Acid Res. and Mol. Biol.*, 1994, pp. 299-329, vol. 47.

Preiss, J. et al. "Starch synthesis in sinks and sources" in *Photoassimilate Distribution in Plants and Crops: Source-sink Relationships*, edited by Zamski, E. et al., 1996, pp. 139-168, Marcil Dekker Inc.

Rijven, A.H.G.C. "Heat inactivation of starch synthase in wheat endosperm tissue" *Plant Physiol.*, 1986, pp. 448-453, vol. 81.

Shaw, J.R. et al. "Genomic nucleotide sequence of a wild-type shrunken-2 allele of *Zea mays*" *Plant Physiology*, 1992, pp. 1214-1216, vol. 98.

Singletary, G.W. et al. "Decreased starch synthesis in heat stressed maize kernels results from reduced ADPG-pyrophosphorylase and starch synthase activities" *Plant Physiol.* 1993, vol. 102, No. 6, supplemental.

Singletary, G.W. et al. "Heat stress during grain filling in maize: effects of carbohydrate storage and metabolism" *Aust. J. Plant Physiol.*, 1994, pp. 829-841, vol. 21.

Smith-White, B.J. et al. "Comparison of proteins of ADP-glucose pyrophosphorylase from diverse sources" *J. Mol. Evol.*, 1992, pp. 449-464, vol. 34.

Sowokinos, J.R. et al. "Pyrophosphorylases in *Solanum tuberosum*" *Plant Physiol.*, 1982, pp. 1459-1466, vol. 69.

Stark et al. "Regulation of the amount of starch in plant tissues by ADP glucose purophosphorylase" *Science*, Oct. 1992, pp. 287-292, vol. 258, No. 5080.

Thompson, L.M. "Climatic change, weather variability, and corn production" *Agron. J.*, Jul./Aug. 1986, pp. 649-653, vol. 78.

Thompson, L.M. "Weather variability, climatic change, and grain production" *Science*, May 1975, pp. 535-541, vol. 188, No. 4188.

Tollenaar, M. et al. "Effects of temperature on rate and duration of kernel dry matter accumulation of maize" *Can. J. Plant Sci.*, Oct. 1988, pp. 935-940, vol. 68.

Tsai, C-Y. et al. "Starch-deficient maize mutant lacking adenosine diphosphate glucose pyrophosphorylase activity" *Science*, Jan. 1966, pp. 341-343, vol. 151, No. 3708.

Wilhelm, E.P. et al. "Heat stress during grain filling in maize: effects on kernel growth and metabolism" *Crop Science*, 1999, pp. 1733-1741, vol. 39.

Xu, D. et al. "Systemic induction of a potato pin2 promoter by wounding, methyl jasmonate, and abscisic acid in transgenic rice plants" *Plant Molecular Biology*, Jul. 1993, pp. 573-588, vol. 22, No. 4.

Yang, T.T. et al. "Optimized codon usage and chromophore mutations provide enhance sensitivity with the green fluorescent protein" *Nucleic Acids Research*, Nov. 1996, pp. 4592-4593, vol. 24, No. 22.

Friedberg, I. "Automated protein function prediction—the genomic challenge" *Briefings in Bioinformatics*, 2006, 7(3):225-242.

\* cited by examiner

```
                     1                                                  50
Mss       (1)  ------MDMALASKASPPPWNATAAEQPIPKRDKAAA------------
Pss       (1)  MAASIGALKSSPSSNNCINERRNDSTRAVSSRNLSFSSSHLAGDKLMPVS
Consensus (1)           L  A AS           A       K        AA
                    51                                                 100
Mss      (32)  -------------------------------NDSTYLNPQAHDSVLGIILGGGA
Pss      (51)  SLRSQGVRFNVRRSPMIVSPKAVSDSQNSQTCLDPDASRSVLGIILGGGA
Consensus(51)                                N   T L P A  SVLGIILGGGA
                   101                                                 150
Mss      (55)  GTRLYPLTKKRAKPAVPLGANYRLIDIPVSNCLNSNISKIYVLTQFNSAS
Pss     (101)  GTRLYPLTKKRAKPAVPLGANYRLIDIPVSNCLNSNISKIYVLTQFNSAS
Consensus(101) GTRLYPLTKKRAKPAVPLGANYRLIDIPVSNCLNSNISKIYVLTQFNSAS
                   151                                                 200
Mss     (105)  LNRHLSRAYGSNIGGYKNEGFVEVLAAQQSPDNPNWFQGTADAVRQYLWL
Pss     (151)  LNRHLSRAYASNMGGYKNEGFVEVLAAQQSPENPDWFQGTADAVRQYLWL
Consensus(151) LNRHLSRAYASNIGGYKNEGFVEVLAAQQSPDNP WFQGTADAVRQYLWL
                   201                                                 250
Mss     (155)  FEEHNVMEFLILAGDHLYRMDYEKFIQAHRETNADITVAALPMDEKRATA
Pss     (201)  FEEHTVLEYLILAGDHLYRMDYEKFIQAHRETDADITVAALPMDEKRATA
Consensus(201) FEEH VLEFLILAGDHLYRMDYEKFIQAHRET ADITVAALPMDEKRATA
                   251                                                 300
Mss     (205)  FGLMKIDEEGRIIEFAEKPKGEQLKAMMVDTTILGLDDVRAKEMPYIASM
Pss     (251)  FGLMKIDEEGRIIEFAEKPQGEQLQAMKVDTTILGLDDKRAKEMPFIASM
Consensus(251) FGLMKIDEEGRIIEFAEKP GEQL AM VDTTILGLDD RAKEMPFIASM
                   301                                                 350
Mss     (255)  GIYVFSKDVMLQLLREQFPEANDFGSEVIPGATSIGKRVQAYLYDGYWED
Pss     (301)  GIYVISKDVMLNLLRDKFPGANDFGSEVIPGATSLGMRVQAYLYDGYWED
Consensus(301) GIYV SKDVMLNLLRD FP ANDFGSEVIPGATSIG RVQAYLYDGYWED
                   351                                                 400
Mss     (305)  IGTIAAFYNANLGITKKPIPDFSFYDRFAPIYTQPRHLPPSKVLDADVTD
Pss     (351)  IGTIEAFYNANLGITKKPVPDFSFYDRSAPIYTQPRYLPPSKMLDADVTD
Consensus(351) IGTI AFYNANLGITKKPIPDFSFYDR APIYTQPRHLPPSKMLDADVTD
                   401                                                 450
Mss     (355)  SVIGEGCVIKNCKINHSVVGLRSCISEGAIIEDSLLMGADYYETEADKKL
Pss     (401)  SVIGEGCVIKNCKIHHSVVGLRSCISEGAIIEDSLLMGADYYETDADRKL
Consensus(401) SVIGEGCVIKNCKI HSVVGLRSCISEGAIIEDSLLMGADYYETDADKKL
                   451                                                 500
Mss     (405)  LAEKGGIPIGIGKNSCIRRAIIDKNARIGDNVKILNADNVQEAAMETDGY
Pss     (451)  LAAKGSVPIGIGKNCHIKRAIIDKNARIGDNVKIINKDNVQEAARETDGY
Consensus(451) LA KG IPIGIGKN  IKRAIIDKNARIGDNVKIIN DNVQEAA ETDGY
                   501            521
Mss     (455)  FIKGGIVTVIKDALLPSGTVI
Pss     (501)  FIKSGIVTVIKDALIPSGIII
Consensus(501) FIK GIVTVIKDALIPSG II
```

FIG. 1

HEAT STABLE VARIANTS OF PLANT ADENOSINE DIPHOSPHATE GLUCOSE PYROPHOSPHORYLASE SMALL SUBUNIT

CROSS-REFERENCE TO RELATED APPLICATION

This application is the U.S. national stage application of International patent application No. PCT/US2004/026965, filed Aug. 18, 2004, which claims the benefit of U.S. Provisional Application Ser. No. 60/496,188, filed Aug. 18, 2003, the disclosure of which is incorporated herein by reference in its entirety.

The subject invention was made with government support under a research project supported by the National Science Foundation Grant No. 9982626. The government has certain rights in this invention.

BACKGROUND OF THE INVENTION

The sessile nature of plant life generates a constant exposure to environmental factors that exert positive and negative effects on its growth and development. One of the major impediments facing modem agriculture is adverse environmental conditions. One important factor which causes significant crop loss is heat stress. Temperature stress greatly reduces grain yield in many cereal crops such as maize, wheat, and barley. Yield decreases due to heat stress range from 7 to 35% in the cereals of world-wide importance.

A number of studies have identified likely physiological consequences of heat stress. Early work by Hunter et al. (1977) using growth chamber conditions showed that temperature decreased the duration of grain filling in maize. Similar results in which the duration of grain filling was adversely altered by increased temperatures were identified by Tollenaar and Bruulsema (1988). Badu-Apraku et al. (1983) measured a marked reduction in the yield of maize plants grown under the day/night temperature regime of 35/15° C. compared to growth in a 25/15° C. temperature regime. Reduced yields due to increased temperatures is also supported by historical as well as climatological studies (Thompson 1986; Thompson 1975; Chang 1981; Conroy et al., 1994). That the physiological processes of the developing seed are adversely affected by heat stress is evident from studies using an in vitro kernel culture system (Jones et al., 1981; Jones et al., 1984; Cheikh et al., 1995). Maize kernels cultured at the above-optimum temperature of 35° C. exhibited a dramatic reduction in weight.

Work with wheat identified the loss of soluble starch synthase (SSS) activity as a hallmark of the wheat endosperm's response to heat stress (Hawker et al., 1993; Denyer et al., 1994; Jenner 1994). Additional studies with SSS of wheat endosperm show that it is heat labile (Rijven 1986; Keeling et al., 1993; Jenner et al., 1995).

ADP glucose pyrophosphorylase (AGP) is another important starch biosynthesis enzyme in plants. AGP catalyzes the conversion of ATP and α-glucose-1-phosphate to ADP-glucose and pyrophosphate. ADP-glucose is used as a glycosyl donor in starch biosynthesis by plants and in glycogen biosynthesis by bacteria. The importance of ADP-glucose pyrophosphorylase as a key enzyme in the regulation of starch biosynthesis was noted in the study of starch deficient mutants of maize (*Zea mays*) endosperm (Tsai et al., 1966; Dickinson et al., 1969). Biochemical and genetic evidence has identified AGP as a key enzyme in starch biosynthesis in higher plants and glycogen biosynthesis in *E. coli* (Preiss et al., 1994; Preiss et al., 1996). AGP catalyzes what is viewed as the initial step in the starch biosynthetic pathway with the product of the reaction being the activated glucosyl donor, ADP glucose. This is utilized by starch synthase for extension of the polysaccharide polymer (reviewed in Hannah 1996).

Initial studies with potato AGP showed that expression in *E. coli* yielded an enzyme with allosteric and kinetic properties very similar to the native tuber enzyme (Iglesias et al., 1993; Ballicora et al., 1995). Greene et al. (1996a, 1996b) showed the usefulness of the bacterial expression system in their structure-function studies with the potato AGP. Multiple mutations important in mapping allosteric and substrate binding sites have been identified (Okita et al., 1996).

AGP enzymes have been isolated from both bacteria and plants. Bacterial AGP consists of a homotetramer, whereas plant AGP from photosynthetic and non-photosynthetic tissues is a heterotetramer composed of two different subunits. The plant enzyme is encoded by two different genes, with one subunit being larger than the other. This feature has been noted in a number of plants. The AGP subunits in spinach leaf have molecular weights of 54 kDa and 51 kDa, as estimated by SDS-PAGE. Both subunits are immunoreactive with antibody raised against purified AGP from spinach leaves (Copeland et al., 1981; Morell et al., 1988). Immunological analysis using antiserum prepared against the small and large subunits of spinach leaf showed that potato tuber AGP is also encoded by two genes (Okita et al., 1990, supra). The cDNA clones of the two subunits of potato tuber (50 and 51 kDa) have also been isolated and sequenced (Muller-Rober et al., 1990; Nakata et al., 1991). The large subunit of potato tuber AGP is heat stable (Nakata et al., 1991, supra).

As Hannah and Nelson (1975, 1976) postulated, both Shrunken-2 (Sh2) (Bhave et al., 1990) and Brittle-2 (Bt2) (Bae et al., 1990) are structural genes of maize endosperm ADP-glucose pyrophosphorylase. Sh2 and Bt2 encode the large subunit and small subunit Of the enzyme, respectively. Based on cDNA sequencing, Sh2 and Bt2 proteins have predicted molecular weight of 57,179 Da (Shaw et al., 1992) and 52,224 Da, respectively. The endosperm is the site of most starch deposition during kernel development in maize. Sh2 and Bt2 maize endosperm mutants have greatly reduced starch levels corresponding to deficient levels of AGP activity. Mutations of either gene have been shown to reduce AGP activity by about 95% (Tsai and Nelson, 1966, supra; Dickinson and Preiss, 1969, supra). Furthermore, it has been observed that enzymatic activities increase with the dosage of functional wild type (wt) Sh2 and Bt2 alleles, whereas mutant enzymes have altered kinetic properties. AGP is the rate limiting step in starch biosynthesis in plants. Stark et al. (1992) placed a mutant form of *E. coli* AGP in potato tuber and obtained a 35% increase in starch content.

The cloning and characterization of the genes encoding the AGP enzyme subunits have been reported for various plants. These include Sh2 cDNA (Bhave et al., 1990, supra), Sh2 genomic DNA (Shaw et al., 1992, supra), and Bt2 cDNA (Bae et al., 1990, supra) from maize; small subunit cDNA (Anderson et al., 1989) and genomic DNA (Anderson et al., 1991) from rice; and small and large subunit cDNAs from spinach leaf (Morell et al., 1988, supra) and potato tuber (Muller-Rober et al., 1990, supra; Nakata et al., 1991, supra). In addition, cDNA clones have been isolated from wheat endosperm and leaf tissue (Olive et al., 1989) and *Arabidopsis thaliana* leaf (Lin et al., 1988). AGP sequences from barley have also been described in Ainsworth et al. (1995).

AGP has been found to function as an allosteric enzyme in all tissues and organisms investigated to date. The allosteric properties of AGP were first shown to be important in *E. coli*. A glycogen-overproducing *E. coli* mutant was isolated and the mutation mapped to the structural gene for AGP, designated as glyC. The mutant *E. coli*, known as glyC-16, was shown to be more sensitive to the activator, fructose 1,6 bisphosphate, and less sensitive to the inhibitor, cAMP (Preiss 1984). Although plant AGP's are also allosteric, they respond to different effector molecules than bacterial AGP's. In plants, 3-phosphoglyceric acid (3-PGA) functions as an activator while phosphate ($PO_4$) serves as an inhibitor (Dickinson and Preiss, 1969, supra).

Using an in vivo mutagenesis system created by the Ac-mediated excision of a Ds transposable element fortuitously located close to a known activator binding site, Giroux et al. (1996) were able to generate site-specific mutants in a functionally important region of maize endosperm AGP. One mutant, Rev6, contained a tyrosine-serine insert in the large subunit of AGP and conditioned a 11-18% increase in seed weight. Published international patent applications WO 99/58698 and WO 98/22601 and issued U.S. Pat. No. 6,069,300 disclose mutations in the large subunit of maize AGP enzyme that, when expressed, confer increased heat stability to the enzyme in comparison to that observed for wild type AGP enzyme. In addition, published international application WO 01/64928 teaches that various characteristics, such as seed number, plant biomass, Harvest Index etc., can be increased in plants transformed with a polynucleotide encoding a large subunit of maize AGP containing the Rev6 mutation.

Ou-Lee and Setter (1985) examined the effects of temperature on the apical or tip regions of maize ears. With elevated temperatures, AGP activity was lower in apical kernels when compared to basal kernels during the time of intense starch deposition. In contrast, in kernels developed at normal temperatures, AGP activity was similar in apical and basal kernels during this period. However, starch synthase activity during this period was not differentially affected in apical and basal kernels. Further, heat-treated apical kernels exhibited an increase in starch synthase activity over control. This was not observed with AGP activity. Singletary et al. (1993, 1994) using an in vitro culture system quantified the effect of various temperatures during the grain fill period. Seed weight decreased steadily as temperature increased from 22-36° C. A role for AGP in yield loss is also supported by work from Duke and Doehlert (1996). These researchers showed that transcript levels decreased to a varying degree, but only one enzyme, AGP, showed a marked decrease in activity with the lower transcript levels. They postulated that AGP may have a faster turnover rate than the other enzymes, and hence is more sensitive to changes in transcript levels. More recent work by Wilhelm et al. (1999) also makes a strong argument for AGP's role in yield loss during heat stress. The Wilhelm et al. authors studied seven inbreds over three replications, and through $Q_{10}$ analysis, showed that AGP was the only enzyme that exhibited lower activity than the control.

Work by Keeling et al. (1993, supra) quantified SSS activity in maize and wheat using $Q_{10}$ analysis, and showed that SSS is an important control point in the flux of carbon into starch. In vitro biochemical studies with AGP and SSS clearly show that both enzymes of maize are heat labile. Maize endosperm AGP loses 96% of its activity when heated at 57° C. for five minutes (Hannah et al., 1980). This is in contrast to potato AGP which is fully stable at 70° C. (Sowokinos et al., 1982; Okita et al., 1990). Although the small subunits of AGP are highly conserved among a variety of plant species (Hannah et al., 2001), the N-termini of potato tuber and maize endosperm small subunits exhibit sequence differences. Heat inactivation studies with SSS showed that it is also labile at higher temperatures, and kinetic studies determined that the Km value for amylopectin rose exponentially when temperature increased from 25-45° C. (Jenner et al., 1995, supra).

BRIEF SUMMARY OF THE INVENTION

The subject invention concerns polynucleotides encoding a small subunit of a plant AGP enzyme that has one or more mutations in the amino acid sequence of the subunit protein, wherein the mutation confers increased heat stability to an AGP enzyme when the mutant small subunit forms part of the enzyme. As provided herein, amino acid changes in the N-terminus of the small subunit of heat labile plant AGP results in AGP enzymes that are significantly more heat stable in that the mutant AGP retains significant levels of enzymatic activity following exposure to heat treatment compared to wild type AGP. In one embodiment, the polynucleotide encodes a mutant small subunit of maize AGP.

The subject invention also concerns mutant AGP small subunit polypeptides encoded by polynucleotides of the present invention. AGP enzymes that comprise a mutant small subunit are also contemplated by the invention.

The subject invention also concerns methods for providing a plant with increased resistance to heat conditions. Plants with heat labile AGP can be transformed with or bred to contain a polynucleotide of the present invention. The subject invention also concerns transformed plant cells, plant tissue, and plants and transgenic progeny thereof.

BRIEF DESCRIPTION OF THE FIGURES

FIG. 1 shows the alignment of the N-termini of the potato tuber (Pss) (SEQ ID NO:43) and maize endosperm (Mss) (SEQ ID NO:2) small subunits of AGP. The amino acid number is given in parentheses to the right of the subunit name. The amino acids in bold are those under evaluation in this study. The consensus sequence is shown under the Pss and Mss sequences in the figure (SEQ ID NO:44).

FIG. 3A shows results as the log of the specific activity verses time. FIGS. 3B-3C show blue native gel of time points from part A. T is the ~220 kD tetramer, D is the ~100 kD dimer and M represents the ~50 kD monomer.

BRIEF DESCRIPTION OF THE SEQUENCES

Figure 2:
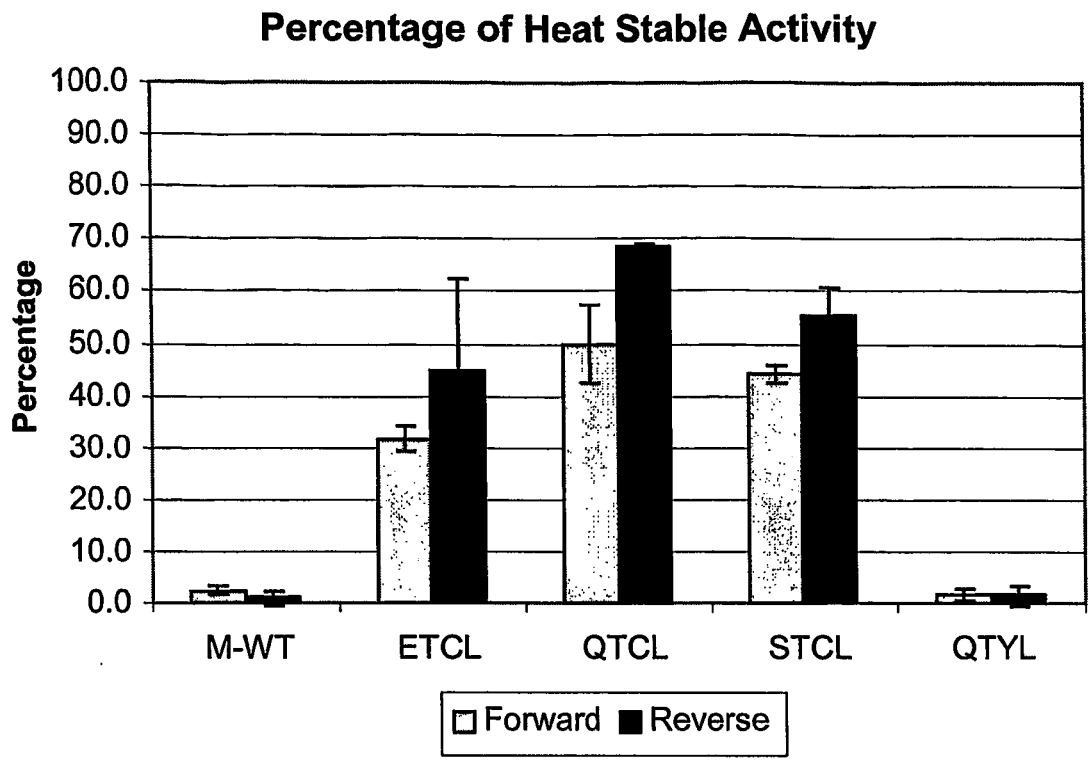
FIG. 2 shows the percent heat stability with various mutations in the maize endosperm AGP small subunit. The results are the average of at least two independent experiments. Each individual experiment contained triplicates of each sample. The percent heat stability is measured by comparing the amount of activity of each sample remaining after heat treatment with the amount of activity obtained before heating. See Table 2 and Materials and Methods for assay conditions.

SEQ ID NO:1 is a polynucleotide sequence encoding a wild type maize endosperm AGP small subunit polypeptide.

SEQ ID NO:2 is a polypeptide having the amino acid sequence encoded by the polynucleotide sequence of SEQ ID NO:1.

SEQ ID NO:3 is a polynucleotide sequence encoding a mutant maize endosperm AGP small subunit polypeptide of the present invention.

SEQ ID NO:4 is a polypeptide having the amino acid sequence encoded by the polynucleotide sequence of SEQ ID NO:3 of the present invention.

SEQ ID NO:5 is a polynucleotide sequence encoding a mutant maize endosperm AGP small subunit polypeptide of the present invention.

SEQ ID NO:6 is a polypeptide having the amino acid sequence encoded by the polynucleotide sequence of SEQ ID NO:5 of the present invention.

SEQ ID NO:7 is a polynucleotide sequence encoding a mutant maize endosperm AGP small subunit polypeptide of the present invention.

SEQ ID NO:8 is a polypeptide having the amino acid sequence encoded by the polynucleotide sequence of SEQ ID NO:7 of the present invention.

SEQ ID NO:9 is a polynucleotide sequence encoding a mutant maize endosperm AGP small subunit polypeptide of the present invention.

SEQ ID NO:10 is a polypeptide having the amino acid sequence encoded by the polynucleotide sequence of SEQ ID NO:9 of the present invention.

SEQ ID NO:11 is a polynucleotide sequence encoding a mutant maize endosperm AGP large subunit polypeptide comprising a Rev6 mutation.

SEQ ID NO:12 is a polypeptide having an amino acid sequence encoded by the polynucleotide sequence of SEQ ID NO:11.

SEQ ID NO:13 is a polynucleotide sequence encoding a mutant maize endosperm AGP large subunit polypeptide comprising a Rev6 mutation and an HS33 mutation.

SEQ ID NO:14 is a polypeptide encoded by the polynucleotide sequence of SEQ ID NO:13.

SEQ ID NO:15 is a polynucleotide sequence encoding a mutant maize endosperm AGP large subunit polypeptide of the present invention designated herein as HS33.

SEQ ID NO:16 is a polypeptide having the amino acid sequence encoded by the polynucleotide sequence of SEQ ID NO:15.

SEQ ID NO:17 is a polynucleotide sequence encoding a mutant maize endosperm AGP large subunit polypeptide of the present invention designated herein as HS13.

SEQ ID NO:18 is a polypeptide having the amino acid sequence encoded by the polynucleotide sequence of SEQ ID NO:17.

SEQ ID NO:19 is a polynucleotide sequence encoding a mutant maize endosperm AGP large subunit polypeptide of the present invention designated herein as HS14.

SEQ ID NO:20 is a polypeptide having the amino acid sequence encoded by the polynucleotide sequence of SEQ ID NO:19.

SEQ ID NO:21 is a polynucleotide sequence encoding a mutant maize endosperm AGP large subunit polypeptide of the present invention designated herein as HS16.

SEQ ID NO:22 is a polypeptide having the amino acid sequence encoded by the polynucleotide sequence of SEQ ID NO:21.

SEQ ID NO:23 is a polynucleotide sequence encoding a mutant maize endosperm AGP large subunit polypeptide of the present invention designated herein as HS40.

SEQ ID NO:24 is a polypeptide having the amino acid sequence encoded by the polynucleotide sequence of SEQ ID NO:23.

SEQ ID NO:25 is a polynucleotide sequence encoding a mutant maize endosperm AGP large subunit polypeptide of the present invention designated herein as HS47.

SEQ ID NO:26 is a polypeptide having the amino acid sequence encoded by the polynucleotide sequence of SEQ ID NO:25.

SEQ ID NO:27 is a polynucleotide sequence encoding a mutant maize endosperm AGP large subunit polypeptide of the present invention designated herein as HS RTS 48-2.

SEQ ID NO:28 is a polypeptide having the amino acid sequence encoded by the polynucleotide sequence of SEQ ID NO:27.

SEQ ID NO:29 is a polynucleotide sequence encoding a mutant maize endosperm AGP large subunit polypeptide of the present invention designated herein as HS RTS 60-1.

SEQ ID NO:30 is a polypeptide having the amino acid sequence encoded by the polynucleotide sequence of SEQ ID NO:29.

SEQ ID NO:31 is a polynucleotide sequence encoding a mutant maize endosperm AGP large subunit polypeptide of the present invention designated herein as HS 33F.

SEQ ID NO:32 is a polypeptide having the amino acid sequence encoded by the polynucleotide sequence of SEQ ID NO:31.

SEQ ID NO:33 is a polynucleotide sequence encoding a mutant maize endosperm AGP large subunit polypeptide of the present invention designated herein as HS33M.

SEQ ID NO:34 is a polypeptide having the amino acid sequence encoded by the polynucleotide sequence of SEQ ID NO:33.

SEQ ID NO:35 is a polynucleotide sequence encoding a mutant maize endosperm AGP large subunit polypeptide of the present invention designated herein as HS7+3.

SEQ ID NO:36 is a polypeptide having the amino acid sequence encoded by the polynucleotide sequence of SEQ ID NO:35.

SEQ ID NO:37 is a polynucleotide sequence encoding a mutant maize endosperm AGP large subunit polypeptide of the present invention designated herein as HS6+3.

SEQ ID NO:38 is a polypeptide having the amino acid sequence encoded by the polynucleotide sequence of SEQ ID NO:37.

SEQ ID NO:39 is a polynucleotide sequence encoding a mutant maize endosperm AGP large subunit polypeptide of the present invention designated herein as HS7+6.

SEQ ID NO:40 is a polypeptide having the amino acid sequence encoded by the polynucleotide sequence of SEQ ID NO:39.

SEQ ID NO:41 is a polynucleotide sequence encoding a mutant maize endosperm AGP large subunit polypeptide of the present invention designated herein as HS7+6+3.

SEQ ID NO:42 is a polypeptide having the amino acid sequence encoded by the polynucleotide sequence of SEQ ID NO:41.

SEQ ID NO:43 is an amino acid sequence of potato tuber small subunit (PSS) of AGP.

SEQ ID NO:44 is the amino acid consensus sequence of Pss (SEQ ID NO:43) and Mss (SEQ ID NO:2).

DETAILED DISCLOSURE OF THE INVENTION

The subject invention concerns polynucleotides encoding a small subunit of a plant AGP enzyme having one or more mutations in the amino acid sequence wherein the mutation confers increased heat stability to the expressed AGP enzyme. Mutations in the N-terminus of the small subunit of heat labile plant AGP provide for AGP enzymes that are significantly more heat stable compared to wild type AGP in that the mutant AGP retains significant levels of enzymatic activity following exposure to heat treatment.

In one embodiment, a polynucleotide of the invention encodes a mutant small subunit of maize AGP. In a further embodiment, a polynucleotide of the invention encodes a maize endosperm AGP small subunit comprising an amino acid mutation wherein the tyrosine at position 36 of the wild type sequence is changed to an amino acid that when expressed as an AGP enzyme confers increased heat stability on the enzyme. In an exemplified embodiment, a polynucleotide of the present invention encodes a maize endosperm AGP small subunit polypeptide comprising an amino acid mutation wherein the tyrosine at position 36 of the wild type sequence is changed to a cysteine. In one embodiment, the polynucleotide encodes a maize endosperm AGP small subunit polypeptide having an amino acid sequence shown in SEQ ID NO:4, or a functional fragment or variant thereof. In a specific embodiment, the polynucleotide encoding the amino acid sequence shown in SEQ ID NO:4 comprises the nucleotide sequence shown in SEQ ID NO:3, or a functional fragment or variant thereof.

In a further exemplified embodiment, a polynucleotide of the invention encodes a maize endosperm AGP small subunit polypeptide comprising an amino acid mutation wherein the tyrosine at amino acid position 36 is changed to a cysteine and, in addition, a glutamine residue is inserted between the serine at amino acid position 34 and the threonine at amino acid position 35 of the wild type AGP small subunit sequence. In one embodiment, the polynucleotide encodes a maize endosperm AGP small subunit polypeptide having an amino acid sequence shown in SEQ ID NO:8, or a functional fragment or variant thereof. In a specific embodiment, the polynucleotide encoding the amino acid sequence shown in SEQ ID NO:8 comprises the nucleotide sequence shown in SEQ ID NO:7, or a functional fragment or variant thereof.

In a still further exemplified embodiment, a polynucleotide of the invention encodes a maize endosperm AGP small subunit polypeptide comprising an amino acid mutation wherein the tyrosine at position 36 of the wild type sequence is changed to a cysteine and, in addition, a glutamic acid residue is inserted between the serine at amino acid position 34 and the threonine at amino acid position 35 of the wild type sequence. In one embodiment, the polynucleotide encodes a maize endosperm AGP small subunit polypeptide having an amino acid sequence shown in SEQ ID NO:10, or a functional fragment or variant thereof. In a specific embodiment, the polynucleotide encoding the amino acid sequence shown in SEQ ID NO:10 comprises a nucleotide sequence shown in SEQ ID NO:9, or a functional fragment or variant thereof.

Because of the homology of AGP polypeptides between various species of plants (Smith-White et al., 1992), the ordinarily skilled artisan can readily determine the position for mutations in an AGP small subunit from plants other than maize that correspond to the position of mutations in maize AGP as disclosed herein, and can prepare polynucleotides encoding mutations in the small subunits of AGP of other plants that correspond to the mutations of the present invention exemplified in maize endosperm AGP small subunit sequences. Thus, the present invention encompasses polynucleotides that encode a mutant small subunit of AGP of plants other than maize, including, but not limited to, wheat, barley, oats, and rice, that confers increased heat stability when expressed in the plant.

The subject invention also concerns polynucleotides encoding a mutant small subunit of the invention and also encoding a large subunit of a plant AGP enzyme. The subject invention also concerns nucleic acid compositions comprising i) a polynucleotide encoding a mutant small subunit of the invention, and ii) a polynucleotide encoding a large subunit of a plant AGP enzyme. The large subunit in any of the embodiments of the present invention can have a wild type sequence or the large subunit can comprise one or more mutations that confer increased heat stability to an AGP enzyme containing the mutant large subunit. Polynucleotide sequences encoding mutant large subunits of maize AGP having increased heat stability include SEQ ID NOs:15, 17, 19, 21, 23, 25, 27, 29, 31, 33, 35, 37, 39, and 41. Polynucleotides can comprise coding and non-coding regions or polynucleotides can comprise the coding only sequences, for example, nucleotides 10 through 1563 of SEQ ID NO:15. Mutant large subunits of maize AGP having increased heat stability include SEQ ID NOs:16, 18, 20, 22, 24, 26, 28, 30, 32, 34, 36, 38, 40, and 42. The large subunit can also comprise mutations that confer increased individual seed weight on a plant expressing an AGP enzyme containing the mutant large subunit. Mutations in the large subunit of a plant AGP that increase heat stability or that increase individual seed weight of a plant have been described in U.S. Pat. Nos. 6,069,300; 5,589,618; 5,650,557; 6,403,863; and 5,872,216 and in published international applications WO 99/58698; WO 98/22601; WO 03/0070901; WO 98/10082; and WO 02/072784.

The subject invention also concerns polynucleotide expression constructs comprising a polynucleotide sequence of the present invention encoding a mutant small subunit of AGP that when present in a functional AGP enzyme confers increased heat stability to the enzyme. In one embodiment, an expression construct of the invention comprises a polynucleotide sequence encoding a maize endosperm AGP small subunit polypeptide comprising an amino acid sequence selected from SEQ ID NO:4, SEQ ID NO:8, SEQ ID NO:10, or a functional fragment or variant thereof. In a specific embodiment, the polynucleotide sequence comprises a polynucleotide sequence selected from SEQ ID NO:3, SEQ ID NO:7, SEQ ID NO:9, or a functional fragment or variant thereof. Expression constructs comprising a polynucleotide sequence encoding a mutant small subunit of AGP can also optionally comprise a polynucleotide sequence encoding a wild type or mutant large subunit of AGP. Expression constructs of the invention generally include regulatory elements that are functional in the intended host cell in which the expression construct is to be expressed in. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a mutant AGP small subunit of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter can be used. Other promoters that can be used for expression constructs in plants include, for example, prolifera promoter, Ap3 promoter, heat shock promoters, T-DNA 1'- or 2'-promoter of *A. tumafaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034, 322) can also be used. Seed-specific promoters such as the promoter from a β-phaseolin gene (of kidney bean) or a glycinin gene (of soybean), and others, can also be used. Constitutive promoters (such as the CaMV, ubiquitin, actin, or NOS promoter), tissue-specific promoters (such as the E8 promoter from tomato), developmentally-regulated promoters, and inducible promoters (such as those promoters than can be induced by heat, light, hormones, or chemicals) are also contemplated for use with polynucleotide expression constructs of the invention.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

Expression constructs can also include one or more dominant selectable marker genes, including, for example, genes encoding antibiotic resistance and/or herbicide-resistance for selecting transformed cells. Antibiotic-resistance genes can provide for resistance to one or more of the following antibiotics: hygromycin, kanamycin, bleomycin, G418, streptomycin, paromomycin, neomycin, and spectinomycin. Kanamycin resistance can be provided by neomycin phosphotransferase (NPT II). Herbicide-resistance genes can provide for resistance to phosphinothricin acetyltransferase or glyphosate. Other markers used for cell transformation screening include genes encoding β-glucuronidase (GUS), β-galactosidase, luciferase, nopaline synthase, chloramphenicol acetyltransferase (CAT), green fluorescence protein (GFP), or enhanced GFP (Yang et al., 1996).

The subject invention also concerns polynucleotide vectors comprising a polynucleotide sequence of the invention that encodes a mutant plant AGP small subunit. Unique restriction enzyme sites can be included at the 5' and 9' ends of an expression construct or polynucleotide of the invention to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides of the present invention can be composed of either RNA or DNA. Preferably, the polynucleotides are composed of DNA. The subject invention also encompasses those polynucleotides that are complementary in sequence to the polynucleotides disclosed herein.

Because of the degeneracy of the genetic code, a variety of different polynucleotide sequences can encode mutant AGP small subunit polypeptides of the present invention. Therefore, all sequences that encode a mutant AGP small subunit of the invention are contemplated within the scope of the invention. In addition, it is well within the skill of a person trained in the art to create alternative polynucleotide sequences encoding the same, or essentially the same, small subunit AGP proteins of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention.

Allelic variants of the nucleotide sequences encoding a small subunit of AGP of the invention are also encompassed within the scope of the invention.

The subject invention also concerns mutant AGP small subunit polypeptides wherein the mutation(s) confers increased heat stability to an AGP enzyme that comprises the mutant small subunit relative to wild type AGP enzyme. The mutant polypeptides can be encoded by polynucleotides of the invention. In an exemplified embodiment, a maize endosperm AGP small subunit polypeptide of the present invention comprises an amino acid mutation wherein the tyrosine at position 36 of the wild type sequence is changed to a cysteine. In a specific embodiment, the maize endosperm AGP small subunit polypeptide comprises an amino acid sequence shown in SEQ ID NO:4, or a functional fragment or variant thereof. In another exemplified embodiment, a maize endosperm AGP small subunit polypeptide of the present invention comprises an amino acid mutation wherein a tyrosine at amino acid position 36 is changed to a cysteine and, in addition, a glutamine residue is inserted between the serine at amino acid position 34 and the threonine at amino acid position 35 of the wild type sequence. In a specific embodiment, the maize endosperm AGP small subunit polypeptide comprises an amino acid sequence shown in SEQ ID NO:8, or a functional fragment or variant thereof. In a further exemplified embodiment, a maize endosperm AGP small subunit polypeptide of the present invention comprises an amino acid mutation wherein the tyrosine at position 36 of the wild type sequence is changed to a cysteine and, in addition, a glutamic acid residue is inserted between the serine at amino acid position 34 and the threonine at amino acid position 35 of the wild type sequence. In a specific embodiment, the maize endosperm AGP small subunit polypeptide comprises an amino acid sequence shown in SEQ ID NO:10, or a functional fragment or variant thereof. The polypeptides of the invention can be in isolated or purified form.

Polypeptide fragments according to the subject invention typically comprise a contiguous span of about or at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, or 475 amino acids of SEQ ID NO:4 (474 amino acids would be the largest fragment size for SEQ ID NO:4 since the full-length sequence is 475 amino acids), SEQ ID NO:8, or SEQ ID NO:10.

Polypeptide fragments of the subject invention can be any integer in length from at least about 25 consecutive amino acids to 1 amino acid less than the sequence shown in SEQ ID NO:4, SEQ ID NO:8, or SEQ ID NO:10. Thus, for SEQ ID NO:4, a polypeptide fragment can be any integer of consecutive amino acids from about 25 to 474 amino acids. The term "integer" is used herein in its mathematical sense and thus representative integers include: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, and/or 475.

Each polypeptide fragment of the subject invention can also be described in terms of its N-terminal and C-terminal positions. For example, combinations of N-terminal to C-terminal fragments of about 25 contiguous amino acids in length to fragments that are one (1) amino acid less than the full length polypeptide of SEQ ID NO:4, SEQ ID NO:8, or SEQ ID NO:10 are included in the present invention. Thus, using SEQ ID NO:4 as an example, a 25 consecutive amino acid fragment could correspond to amino acids of SEQ ID NO:4 selected from the group consisting of 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, 26-50, 27-51, 28-52, 29-53, 30-54, 31-55, 32-56, 33-57, 34-58, 35-59, 36-60, 37-61, 38-62, 39-63, 40-64, 41-65, 42-66, 43-67, 44-68, 45-69, 46-70, 47-71, 48-72, 49-73, 50-74, 51-75, 52-76, 53-77, 54-78, 55-79, 56-80, 57-81, 58-82, 59-83, 60-84, 61-85, 62-86, 63-87, 64-88, 65-89, 66-90, 67-91, 68-92, 69-93, 70-94, 71-95, 72-96, 73-97, 74-98, 75-99, 76-100, 77-101, 78-102, 79-103, 80-104, 81-105, 82-106, 83-107, 84-108, 85-109, 86-110, 87-111, 88-112, 89-113, 90-114, 91-115, 92-116, 93-117, 94-118, 95-119, 96-120, 97-121, 98-122, 99-123, 100-124, 101-125, 102-126, 103-127, 104-128, 105-129, 106-130, 107-131, 108-132, 109-133, 110-134, 111-135, 112-136, 113-137, 114-138, 115-139, 116-140, 117-141, 118-142, 119-143, 120-144, 121-145, 122-146, 123-147, 124-148, 125-149, 126-150, 127-151, 128-152 and so on. Similarly, the amino acids corresponding to all other fragments of sizes between 26 consecutive amino acids and 474 consecutive amino acids of SEQ ID NO:4 (or 475 for SEQ ID NO:8 and SEQ ID NO:10) are included in the present invention and can also be immediately envisaged based on these examples. Therefore, additional examples, illustrating various fragments of the polypeptides of SEQ ID NO:4, SEQ ID NO:8, or SEQ ID NO:10 are not individually listed herein in order to avoid unnecessarily lengthening the specification.

Polypeptide fragments comprising:

a) 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, or 475 consecutive amino acids of SEQ ID NO:4, SEQ ID NO:8, or SEQ ID NO:10 may alternatively be described by the formula "n to c" (inclusive), where "n" equals the N-terminal amino acid position and "c" equals the C-terminal amino acid position of the polypeptide. In this embodiment of the invention, "n" is an integer having a lower limit of 1 and an upper limit of the total number of amino acids of the full length polypeptide minus 24 (e.g., 475-24=451 for SEQ ID NO:4). "c" is an integer between 25 and the number of amino acids of the full length polypeptide sequence (475 for SEQ ID NO:4) and "n" is an integer smaller than "c" by at least 24. Therefore, for SEQ ID NO:4, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 12, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451; and "c" is any integer selected from the group consisting of 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, and 475, provided that "n" is a value less than "c" by at least 24. Every combination of "n" and "c" positions are included as specific embodiments of polypeptide fragments of the invention. Examples illustrating the various fragments of a polypeptide contemplated under this formula are not individually listed in order to avoid unnecessarily lengthening the specification. However, all embodiments of a particular polypeptide can be immediately envisaged from the description provided herein. All ranges used to describe any polypeptide fragment embodiment of the present invention are inclusive unless specifically set forth otherwise.

Substitution of amino acids other than those specifically exemplified or naturally present in a plant AGP small subunit of the invention are also contemplated within the scope of the present invention. For example, non-natural amino acids can be substituted for the amino acids of an AGP small subunit, so long as the AGP small subunit protein having the substituted amino acids retains substantially the same biological activity as the AGP small subunit protein in which amino acids have not been substituted. Examples of non-natural amino acids include, but are not limited to, ornithine, citrulline, hydroxyproline, homoserine, homocysteine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of an AGP small subunit used in the present invention are also encompassed within the scope of the invention.

Amino acids can be generally categorized in the following classes: non-polar, uncharged polar, basic, and acidic. Conservative substitutions whereby an AGP small subunit protein of the present invention having an amino acid of one class is replaced with another amino acid of the same class fall within the scope of the subject invention so long as the AGP small subunit protein having the substitution still retains substantially the same biological activity as the AGP small subunit protein that does not have the substitution. Polynucleotides encoding an AGP small subunit protein having one or more amino acid substitutions in the sequence are contemplated within the scope of the present invention. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode biologically-active mutant AGP small subunit proteins of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of an AGP small subunit of the present invention can be generated as described herein and tested for the presence of enzymatic function using standard techniques known in the art. For example, for testing fragments and/or variants of an AGP small subunit, the small subunit can be expressed in conjunction with an AGP large subunit to form an AGP heterotetramer enzyme and the enzyme assayed by way of a "forward" assay, i.e., assaying for the conversion of ATP and α-glucose-1-phosphate to ADP-glucose and pyrophosphate, or by way of a "reverse" assay according to the present invention. AGP-enzymes comprising a fragment and/or variant of an AGP small subunit of the invention can also be subjected to heat treatment, e.g., 55-60° C. for several minutes, prior to enzymatic assay in order to test for increased heat stability of the enzyme. Thus, an ordinarily skilled artisan can readily prepare and test fragments and variants of an AGP small subunit of the invention and determine whether the fragment or variant retains functional enzymatic activity and/or confers heat stability relative to full-length or a non-variant AGP small subunit.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

Tm=81.5 C+16.6 Log [Na+]+0.41(% G+C)−0.61(% formamide)-600/length of duplex in base pairs.

Washes are typically carried out as follows:

(1) Twice at room temperature for 15 minutes in 1× SSPE, 0.1% SDS (low stringency wash).

(2) Once at Tm-20 C for 15 minutes in 0.2× SSPE, 0.1% SDS (moderate stringency wash).

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

The subject invention also concerns cells transformed with a polynucleotide of the present invention encoding a mutant AGP small subunit of the invention. The subject invention also concerns cells transformed with a nucleic acid composition of the present invention. In one embodiment, the cell is transformed with a polynucleotide sequence comprising a sequence encoding the amino acid sequence shown in any of SEQ ID NO:4, SEQ ID NO:8, SEQ ID NO:10, or a functional fragment or variant thereof. In a specific embodiment, the cell is transformed with a polynucleotide sequence shown in any of SEQ ID NO:3, SEQ ID NO:7, SEQ ID NO:9, or a functional fragment or variant thereof. Preferably, the polynucleotide sequence is provided in an expression construct of the invention. The transformed cell can be a prokaryotic cell, for example, a bacterial cell such as *E. coli* or *B. subtilis*, or the transformed cell can be a eukaryotic cell, for example, a plant cell, including protoplasts, or an animal cell. Plant cells include, but are not limited to, dicotyledonous, monocotyledonous, and conifer cells. Animal cells include human cells, mammalian cells, avian cells, and insect cells. Mammalian cells include, but are not limited to, COS, 3T3, and CHO cells.

Plants, plant tissues, and plant cells transformed with or bred to contain a polynucleotide of the invention or a nucleic acid composition of the invention are also contemplated by the present invention. Plants, plant tissues, and plant cells that contain an AGP enzyme comprising a mutant small subunit of the invention and, optionally, a mutant AGP large subunit that confers increased heat stability and/or increased seed weight for a plant is also contemplated within the scope of the invention. Plants and plant tissue expressing the mutant polynucleotides of the invention exhibit increased heat stability when subjected to heat stress during development. Increased heat stability of plants can provide for increased yields from those plants, particularly under conditions of heat stress. Plants within the scope of the present invention include monocotyledonous plants, such as, for example, rice, wheat, barley, oats, sorghum, maize, sugarcane, pineapple, onion, bananas, coconut, lilies, turfgrasses, and millet. In a particularly preferred embodiment, the plant is a cereal. Cereals to which this invention applies include, for example, maize, wheat, rice, barley, oats, rye, and millet. Preferably, the plant, plant tissue, or plant cell is *Zea mays*. Plants within the scope of the present invention also include dicotyledonous plants, such as, for example, peas, alfalfa, tomato, melon, chickpea, chicory, clover, kale, lentil, soybean, tobacco, potato, sweet potato, radish, cabbage, rape, apple trees, grape, cotton, sunflower, and lettuce; and conifers. Techniques for transforming plant cells with a gene are known in the art and include, for example, *Agrobacterium* infection, biolistic methods, electroporation, calcium chloride treatment, etc. Transformed cells can be selected, redifferentiated, and grown into plants using standard methods known in the art. The seeds and progeny of any transformed or transgenic plant cells or plants of the invention are also included within the scope of the present invention.

Plants can also be bred to contain a polynucleotide to express a mutant small subunit of the invention. In addition, a plant having a polynucleotide of the invention in its genome can be bred with a plant that expresses a mutant heat stable and/or phosphate insensitive large subunit of AGP and progeny selected that express an AGP enzyme comprising a mutant small subunit of the invention and the mutant large subunit from the parent plants. Methods for breeding and selecting for plants having the desired characteristics are known in the art.

The subject invention also concerns methods for providing a plant with increased resistance to heat stress or elevated temperatures by incorporating a polynucleotide of the present invention in the genome of the plant cells and expressing the polypeptide encoded by the polynucleotide. In one embodiment, a plant is grown from the plant cells. Preferably, the polynucleotide encodes a mutant AGP small subunit derived from the same plant species as the plant. In one embodiment, the plant is maize. In a specific embodiment, a polynucleotide encoding an amino acid sequence shown in SEQ ID NO:4, SEQ ID NO:8, SEQ ID NO:10, or a functional fragment or variant thereof, is incorporated into a maize plant genome. In a specific embodiment, the polynucleotide comprises a nucleotide sequence shown in SEQ ID NO:3, SEQ ID NO:7, SEQ ID NO:9, or a functional fragment or variant thereof. Methods of the invention also contemplate incorporating a polynucleotide that encodes a mutant large subunit of AGP that comprises a mutation conferring heat stability and/or phosphate insensitivity into the genome of a plant cell that comprises a polynucleotide of the invention and expressing the mutant large subunit encoded by the polynucleotide to provide a mutant AGP enzyme of the invention.

The subject invention also concerns AGP enzymes that comprise heat stable mutants of the small subunit of AGP of the present invention combined with large subunits of AGP, including wild type and heat stable mutants of the large subunit of AGP. The mutant subunits can be provided as fragments or variants as described herein. The AGP enzymes of the invention can be in isolated or purified form. Mutants of the large subunit of AGP that confer heat stability to an AGP enzyme can also be readily prepared and are described in U.S.

Pat. No. 6,069,300 and published international applications WO 99/58698 and WO 98/22601. Polynucleotide sequences encoding mutant large subunits of maize AGP having increased heat stability include SEQ ID NOs:15, 17, 19, 21, 23, 25, 27, 29, 31, 33, 35, 37, 39, and 41. Mutant large subunits of maize AGP having increased heat stability include SEQ ID NOs:16, 18, 20, 22, 24, 26, 28, 30, 32, 34, 36, 38, 40, and 42. Heat stable mutants of the large subunit can be co-expressed with the mutant small subunits of the present invention to further enhance the stability of an AGP enzyme. The subject invention also contemplates AGP enzymes that comprise mutant small subunits of the present invention combined with a mutant large subunit that confers increased individual seed weight when expressed in an AGP enzyme in a plant, such as the Rev6 mutation. Mutant large subunits of maize AGP that confer increased individual seed weight include polypeptides comprising the amino acid sequence shown in SEQ ID NO:12. Polynucleotides encoding mutant large subunits that confer increased individual seed weight include SEQ ID NO:11. The combination of a mutant small subunit of the invention having a heat stabilizing mutation, and a mutant large subunit having a heat stabilizing mutation such as, for example, HS 33 or HS 40, and a mutation conferring increased seed weight, e.g., Rev 6, in a large subunit of maize AGP is specifically contemplated in the present invention. Mutant large subunits of maize AGP having heat stability and conferring increased individual seed weight include polypeptides comprising the amino acid sequence shown in SEQ ID NO:14. Polynucleotides encoding mutant large subunits that have heat stability and confer increased individual seed weight include SEQ ID NO:13. U.S. Pat. Nos. 5,589,618 and 5,650,557 disclose polynucleotides (e.g., Rev6) that encode mutations in the large subunit of AGP that confer increased seed weight in plants that express the mutant polypeptide. The subject invention also concerns AGP enzymes that comprise heat stable small subunit mutants of the present invention and mutant large subunits as described in International patent Application No. PCT/US01/06622, which was published on Sep. 7, 2001 as WO 01/64928.

Materials and Methods

Site-Directed Mutagenesis.

Mutations in the maize endosperm small subunit were created essentially as described by Horton et al. (1993). The maize endosperm AGP small subunit is encoded by the gene brittle-2 (Bt2). Construct STCL (SEQ ID NO:3) encodes a maize AGP small subunit protein (SEQ ID NO:4) having a change from a tyrosine at amino acid position 36 of the wild type sequence to a cysteine. Construct QTYL (SEQ ID NO:5) encodes a maize AGP small subunit protein (SEQ ID NO:6) having an insertion of a glutamine between the serine at amino acid position 34 and the threonine at amino acid position 35 of the wild type sequence. The QTCL construct (SEQ ID NO:7) encodes a maize AGP small subunit protein (SEQ ID NO:8) having a change from a tyrosine at amino acid position 36 to a cysteine and an insertion of a glutamine between the serine at amino acid position 34 and the threonine at amino acid position 35. Another construct, ETCL (SEQ ID NO:9), encodes a maize AGP small subunit protein (SEQ ID NO:10) having a glutamic acid insertion between the serine at amino acid position 34 and the threonine at amino acid position 35, and the change from a tyrosine to a cysteine at position 36. The mutations were verified by sequence analysis.

Plasmids and Bacterial Strains.

DNA fragments created from mutagenic PCR of the maize endosperm small subunit were digested with Nco I and Kpn I. These digested fragments were used to replace the equivalent wild type region of Bt2 in an expression vector. The vector was transformed into the *Escherichia coli* strain AC70R1-504 which also contained the wild type shrunken-2 (Sh2) coding region on a compatible expression vector (Giroux et al., 1996). Sh2 encodes the large subunit of AGP. The SH2 and BT2 proteins can polymerize to form active heterotetrameric AGP. The AC70RI-504 cell line contains a mutation which renders the strain incapable of producing bacterial AGP (Iglesias et al., 1993).

Growth and Purification of Maize AGP from *E. coli*.

Protein inductions were as described by Greene and Hannah (1998) with a few modifications. *E. coli* strain AC70R1-504, which lacks the functional AGP gene and cannot synthesize glycogen, was transformed with both pMoncSh2 and pMoncBt2 (plasmids containing the large and small subunit of wt-AGP respectively). An overnight culture was grown with constant shaking at 225 rpm at 37° C. in LB media containing 75 ug/ml spectinomycin and 50 µg/ml kanamycin. An aliquot of the overnight culture (12.5 ml) was used to inoculate a 1 L flask containing the same media. The 1 L flask was grown until the $OD_{600}$ reached 0.5-0.6. The cultures were cooled to room temperature and protein expression was induced by the addition of 0.2 mM isopropyl-beta-D-thiogalactoside (IPTG) and 0.02 mg/ml nalidixic acid. Expression continued for 3 hours at room temperature with constant shaking. Cells were centrifuged at 8000×g supernatant removed and stored as pellets at −80° C.

Preparation of Extracts.

For crude extracts, the bacterial pellets were resuspended in 1.0 ml of extraction buffer (50 mM HEPES, pH 7.5, 200 mM KCl, 10 mM $MgCl_2$, 2.5 mM EDTA and 5% Sucrose) with 20% ammonium sulfate, 50 µg/ml lysozyme, 1 µg/ml pepstatin, 1 µg/ml leupeptin, 1 mM PMSF, 10 µg/ml chymostatin, and 1 mM benzamidine added. The lysate was maintained on ice and sonicated three times for ten seconds each. The sample was centrifuged for five minutes at 12,500 rpm at 4° C. and the supernatant was transferred to a new tube on ice. Solid ammonium sulfate was added to 45% saturation and the sample was centrifuged for five minutes at 12,500 rpm at 4° C. The pellet was resuspended in extraction buffer containing protease inhibitors and stored on ice. The concentration of the crude protein extract was determined using the Bio-Rad Protein Assay Using BSA as a standard.

Assay A (Forward Direction, Radioactive).

AGP activity of the crude extracts were determined in the direction of ADP-glucose synthesis as described in Burger et al. (2003) with the only modifications being a decrease in the reaction time to five minutes. AGP activity in the direction of Glucose-1-Phosphate (G-1-P) synthesis is essentially as described in Kleczkowski et al. (1993) with a reduction in scale. Nanomoles of product are calculated by generating a standard curve with G-1-P. Both the forward and reverse reactions were started by the addition of the enzyme. For heat treatments of the crude extract, the enzymes were diluted to 1.0 µg/µl and divided into two tubes. A single tube remained on ice while the second tube was placed at 58° C. for 6 minutes with occasional gentle agitation. The value reported within an experiment is the average from triplicate samples.

Assay B (Reverse Direction, Radioactive).

A non-radioactive endpoint assay was used to determine the amount of glucose-1-phosphate produced by coupling it to NADH production using phosphoglucomutase and glucose-6-phosphate dehydrogenase. The temperature of all the assays was 37° C. unless otherwise specified. Standard reaction mixtures contained 100 m M MOPS HCl pH 7.4, 0.4 mg/ml BSA, 5 mM $MgCl_2$, 1 mM ADP-Glucose, 20 mM 3-P Phosphoglyceric Acid, 1 mM Sodium Pyrophosphate and enzyme in 100 µl reaction volume. Reactions were incubated at 37° C. for 5 minutes and terminated by boiling in a water bath for 1 minute. After reaction termination, 330 µl of water was added to the reaction mixture followed by 70 µl of a development mix containing a final concentration of 100 m M MOPS HCl pH 7.4, 0.1 mg/ml BSA, 7 mM $MgCl_2$, 0.6 mM NAD, 1U Glucose-6-Phosphate dehydrogenase, and 1U Phosphoglucomutase. Reactions were centrifuged for 5 minutes and then the absorbance read at 340 mm The amount of G-1-P produced in each assay was calculated based on a standard curve using freshly prepared G-1-P instead of enzyme. All assay tubes were pre-warmed to 37° C. prior to assaying. All assays were initiated by the addition of enzyme. Specific activity is defined as a unit/mg protein. Purification was always monitored using the reverse assay.

Assay C (Forward Reaction, Nonradioactive).

A non-radioactive endpoint assay was used to determine the amount of PPi produced by coupling it to a decrease in NADH using pyrophosphate reagent (Sigma P-7275). Standard reaction mixtures contained 50 mM HEPES pH 7.0, 15 mM MgCl2, 4.0 mM ATP, and 4.0 mM Glucose-1-Phosphate in a total volume of 200 µl. The 3-Phosphoglyceric acid (3-PGA) was added at varying amounts, as specified. When varied, the substrates ranged from 0-5 mM. Reactions were terminated after 5 minutes by boiling in a water bath for 1 minute. The reactions were developed by adding 300 µl of Pyrophosphate reagent (1 bottle diluted to 22.5 ml with water) to each assay and then the absorbance read at 340 nm. The change in absorbance between the blank and the reaction was used to calculate the amount to PPi produced for each sample. All reactions were linear with time and enzyme concentration. All assay tubes were pre-warmed to 37° C. prior to assaying and were initiated by the addition of enzyme.

Enzyme Kinetics.

To determine the extent of activation with or with out 3-PGA, 0.1 or 2.0 µg respectively, of purified maize wt-AGP was incubated for 12.5 minutes in the forward assay. To determine the activation constant for the maize wt AGP, 0.2 µg of purified maize wt-AGP was incubated for 12.5 minutes in the forward assay. 3-PGA concentrations ranged from 0-5.0 mM. Curves were fit using Graph Pad Prism using non-linear regression. At this enzyme concentration no activity can be detected in the absence of 3-PGA.

Native Protein Gels.

The ½ life of wt and QTCL at 42° C. was determined by desalting enzyme in 50 mM HEPES, pH 6.5, 5.0 mM $MgCl_2$, 0.5 mM EDTA. Heat was applied to desalted enzyme (0.15 mg/ml) and at the appropriate time, enzyme was withdrawn from the tube and placed on ice. This enzyme was then divided for use in activity assays and blue native gels. All reactions were carried out using Assay B with 10 mM 3-PGA. The blue native gels were prepared as outlined on World Wide Website: amershambiosciences.com under the heading of gradient gels. The gradient used was 5-18%. Two types of cathode buffer were prepared, one contained 0.002% coomassie and the other without coomassie. Aminocaproic acid was not used in the gel buffer. The gels were run at 4° C. for 20 minutes at 100V in cathode buffer containing coomassie then the voltage was increased to 200V for an additional 20 minutes. Finally, the gel was transferred to cathode buffer without coomassie and run at 200V until the dye front was off the gel. The gel was equilibrated in cold 1× Transfer Buffer (25 mM Tris Base, 192 mM Glycine, and 20% Methanol)+ 1% SDS.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Enzymatic Activity and Heat Stability of Mutant AGP

Point mutations were created in the N-terminus of the maize endosperm small subunit, brittle 2 (Bt2) and expressed with wild type large subunit, Shrunken 2, to form a mutant maize AGP enzyme. The mutant enzyme was assayed for increased heat stability relative to wild type maize endosperm AGP. All the modified BT2 proteins tested exhibit activity levels comparable to the wild type maize endosperm before heat treatment; however, the QTCL mutant has a slight increase. Since the specific activity is consistent among the preparations (Table 2), there is no change in enzyme turnover or expression levels caused by the mutations. The most dramatic increases in activity over wild type maize endosperm are observed after heat treatments of 58° C. for six minutes. The change of tyrosine to a cysteine results in a dramatic increase in heat stability (see FIG. 2, Table 3). In the case of QTCL, greater than 50% of the enzyme remains active after heat treatment while only 2% of the wild type is active. The addition of glutamine by itself does not confer heat stability to the protein; however, it contributes to an increase in overall activity of the protein.

TABLE 2

Percentage of specific activity of small subunit mutations compared to the wild type maize endosperm AGP

| Sample | | Forward Assay | Reverse Assay |
|---|---|---|---|
| WT-STYL | (SEQ ID NO: 2) | 100 | 100 |
| ETCL | (SEQ ID NO: 10) | 123 ± 25 | 130 ± 0 |
| QTCL | (SEQ ID NO: 8) | 170 ± 18 | 165 ± 7 |
| STCL | (SEQ ID NO: 4) | 135 ± 5 | 150 ± 5 |
| QTYL | (SEQ ID NO: 6) | 120 ± 5 | 135 ± 21 |

Table 2: The results are the averages of at least two experiments. All experiments contained triplicates of each sample. The forward activity was measured in the direction of ADP-glucose synthesis in the presence of 10 mM 3-PGA. The reverse assay measures the amount of glucose-1-phosphate produced by conversion to NADH through a series of secondary reactions. The amount of NADH present was quantified using a spectrophotometer. All assays were done from crude extracts of E. coli expressed proteins.

TABLE 3

Percent Heat Stability of small subunit mutations

| Sample | | Forward Assay | Reverse Assay |
|---|---|---|---|
| WT Maize | (SEQ ID NO: 2) | 2.4% ± 0.8 | 0.9% ± 1.2 |
| ETCL | (SEQ ID NO: 10) | 31.7% ± 2.5 | 44.5% ± 17.7 |
| QTCL | (SEQ ID NO: 8) | 50.0% ± 7.2 | 68.5% ± 0.7 |
| STCL | (SEQ ID NO: 4) | 44.3% ± 1.5 | 55.0% ± 5.7 |
| QTYL | (SEQ ID NO: 6) | 1.7% ± 1.1 | 1.4% ± 2.0 |

Table 3: The results are the average of at least two independent experiments. Each individual experiment contained triplicates of each sample. The percent heat stability is measured by comparing the amount of activity of each sample remaining after heat treatment with the amount of activity obtained before heating. See Table 2 and Materials and Methods for assay conditions.

Example 2

Kinetic Analysis

Due to the increased activity levels and greater heat stability, the QTCL mutant was chosen for further kinetic analysis. The QTCL mutant and wild type enzymes were purified from E. coli as described in the materials and methods. The kinetic constants, Km and Vmax for ATP and Glucose-1-Phosphate (G-1-P) were determined for both the wild type and the QTCL enzyme (Table 4). The kinetic constants for wild type, 0.066 mM for ATP and 0.036 mM for G-1-P, are similar to those reported in the literature. The Km values for the QTCL mutant are also similar to those obtained for the wild type enzyme. The kinetic constants determined for the forward reaction show that the mutation is not interfering with the binding of substrates. Only slight changes are seen in the Km for both ATP and G-1-P. The catalytic efficiency (Kcat/Km) is also similar for both enzymes.

Maize endosperm AGP can be activated by the presence of 3-PGA and inactivated in the presence of Pi. The activation rate has been measured from E. coli expressed AGP and several genotypes of corn. The 3-PGA activation rate tends to vary between 3- to 20-fold, which may be a reflection of different genotypes, pH of the assay or purity levels of the extracted enzyme. Since 3-PGA and Pi have an antagonistic relationship, the ratio of the two determines the rate of activation or inhibition. The rate of activation and de-activation of the QTCL mutant enzyme was compared to wild type enzyme grown in E. coli. The results are presented in Table 5.

The Ka for the QTCL enzyme is approximately 2-fold higher than that of wild type AGP. This data shows that the QTCL mutant enzyme is slightly less sensitive to 3-PGA levels. The extent of phosphate de-activation was determined by varying the phosphate concentration while the 3-PGA concentration remained fixed at 2.5 mM. A comparison of the Ki's reveals that the QTCL enzyme is more susceptible to phosphate inhibition than wild type. This data is consistent with $PO_4-$ being a deactivator of the enzyme. It has been recognized by many groups that there is a direct correlation between 3-PGA activation and $PO_4-$ de-activation. It is easier for the $PO_4-$ to inhibit the QTCL enzyme since the experiment has only approximately 2.5× the saturating amount of 3-PGA. However, the wild type AGP is approximately 5× saturated with 3-PGA so the $PO_4-$ is less likely to de-activate the enzyme at this 3-PGA concentration.

TABLE 4

Kinetic Values for purified QTCL and WT

| | ATP | | | Glucose-1-Phosphate | | |
|---|---|---|---|---|---|---|
| | Km (mM) | Vmax (μmol/min/mg) | Kcat/Km | Km (mM) | Vmax (μmol/min/mg) | Kcat/Km |
| WT (SEQ ID NO: 2) | 0.066 ± 0.01 | 9.25 ± 0.32 | 1.2 × 106 | 0.036 ± 0.008 | 5.5 ± 0.29 | 1.3 × 106 |
| QTCL (SEQ ID NO: 8) | 0.14 ± 0.01 | 23.4 ± 0.53 | 1.4 × 106 | 0.041 ± 0.008 | 16.45 ± 0.82 | 3.4 × 106 |

Table 4: The enzymes were purified as described in materials and methods. All reactions were performed in the presence of 10 mM 3-PGA. The reactions were performed in triplicate and started by the addition of 0.15 μg of purified enzyme. The reactions were incubated for 10 minutes at 37° C. then terminated by boiling for two minutes.

TABLE 5

Activation and Inhibition of QTCL and WT

| | | 3-PGA $K_a$ | Pi $K_i$ |
|---|---|---|---|
| WT | (SEQ ID NO: 2) | 0.57 ± 0.055 | 1.67 |
| QTCL | (SEQ ID NO: 8) | 1.08 ± 0.13 | 0.4 |

Table 5: All assays were performed in the forward direction (Assay C) using standard reaction conditions. The $K_a$ for 3-PGA was determined by adding varying amounts of the effector from 0-3 mM. The value of the Ki for Pi was calculated in the presence of 2.5 mM 3-PGA. The reactions were incubated for 10 minutes at 37° C. then terminated by boiling for two minutes. The reactions were performed in triplicate and started by the addition of 0.15 μg of purified enzyme. The curves were created using Graph Pad Prism with non-linear regression.

Example 3

Analysis of Purified AGP Enzyme

Figure 3A:
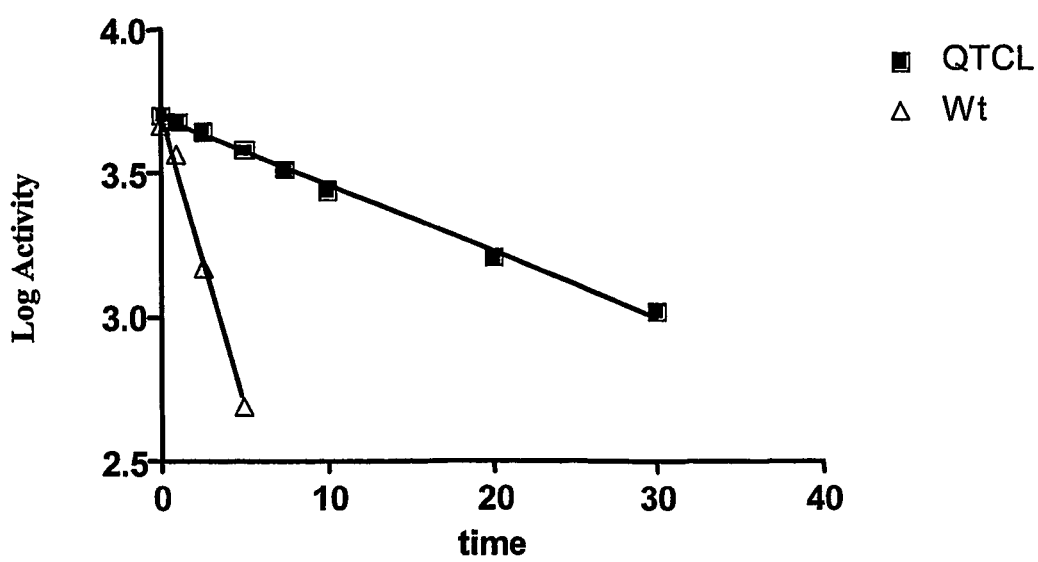
FIGS. 3A-3C show reactions carried out at pH 7.0. Reactions were performed in duplicate and were started with 0.15 µg of purified enzyme. Reactions proceeded for 15 minutes and were denatured in a boiling water bath for 2 minutes.
Figure 3B:
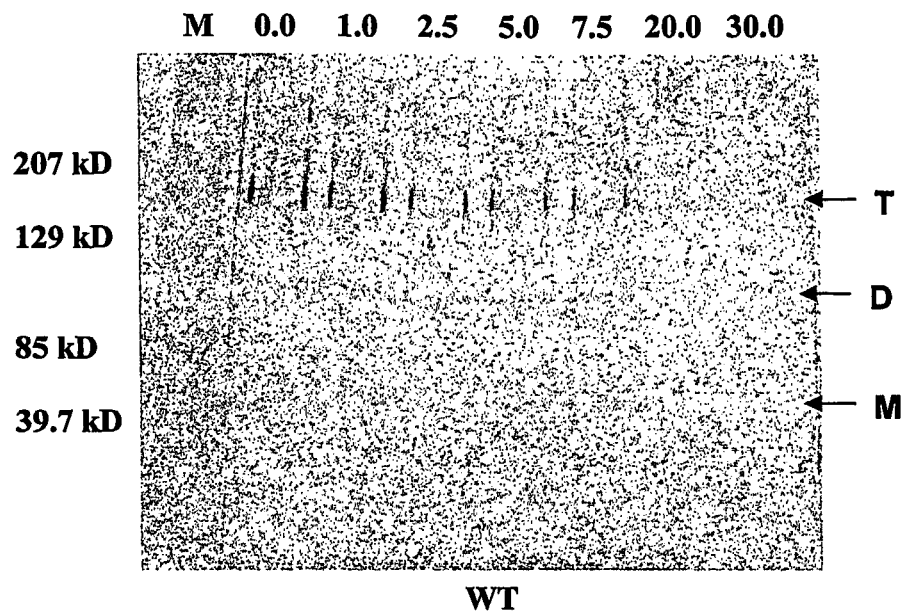
Figure 3C:
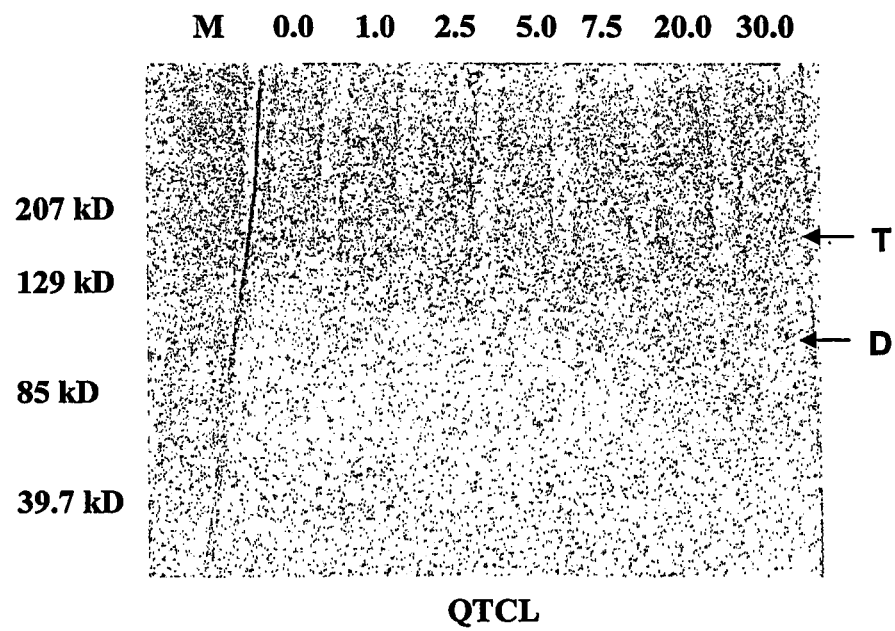

The data from the crude extracts shows that the QTCL mutant conferred more heat stability than the wild type enzyme. However, to obtain a more detailed view of the inactivation kinetics, the $t_{1/2}$ was calculated from a graph of log % activity versus time for both the wild type AGP and the QTCL mutant (FIGS. 3A-3C). Purified wild type and mutant AGP enzymes were incubated at 42° C. for varying amounts of time then evaluated for AGP activity and protein structure. Although the purified QTCL enzyme conferred some degree of heat stability at much higher temperatures (data not shown), 42° C. was chosen because the wild type enzyme dies rapidly at elevated temperatures. At various time points, a fraction of the enzyme was withdrawn and placed on ice. The sample was divided and a portion was used for both enzymatic and structural analysis. The enzymatic data show a linear response with time (FIG. 3A). The half-life of the QTCL variant and wt AGP were shown to be 12.0 min and 1.25 min respectively. The half-life of the enzyme is increased approximately 10-fold over wt AGP at this temperature. Blue native gels were then used to indicate the multi-meric state of the enzyme at the given time points (FIGS. 3B-3C). Initially, both wild type and QTCL have a high percentage of heterotetramers. The QTCL protein is almost exclusively in the heterotetrameric state. However, following a five-minute heat treatment the wild type heterotetramer has a higher percentage of dimers and monomers. By 20 minutes, activity cannot be detected for the wild type enzyme and the protein has completely formed an un-resolved aggregate. In contrast, the enzyme containing the QTCL mutant subunit remains predominantly as a heterotetramer, even after a 30-minute heat treatment.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Pat. No. 5,625,136
U.S. Pat. No. 6,069,300
U.S. Pat. No. 5,034,322
U.S. Pat. No. 5,106,739
U.S. Pat. No. 5,589,618
U.S. Pat. No. 5,650,557
U.S. Pat. No. 6,403,863
U.S. Pat. No. 5,872,216
WO 98/10082
WO 98/22601
WO 99/58698
WO 01/64928
WO 02/072784
WO 03/0070901
Ainsworth, C., Hosein, F., Tarvis, M., Weir, F., Burrell, M., Devos, K. M., Gale, M. D. (1995) "Adenosine Diphosphate Glucose Pyrophosphorylase Genes in Wheat: Differential Expression and Gene Mapping" *Planta* 197:1-10.
Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
Anderson, J. M., J. Hnilo, R. Larson, T. W. Okita, M. Morell, J. Preiss (1989) "The Encoded Primary Sequence of a Rice Seed ADP-glucose Pyrophosphorylase Subunit and its Homology to the Bacterial Enzyme" *J. Biol. Chem.* 264: 12238-12242.
Anderson, J. M., R. Larson, D. Landencia, W. T. Kim, D. Morrow, T. W. Okita, J. Preiss (1991) "Molecular Characterization of the Gene Encoding a Rice Endosperm-Specific ADP glucose Pyrophosphorylase Subunit and its Developmental Pattern of Transcription" *Gene* 97:199-205
Badu-Apraku, B., Hunter, R. B., Tollenaar, M. (1983) "Effect Of Temperature During Grain Filling On Whole Plant And Grain Yield In Maize (*Zea mays* L.)" *Can. J. Plant. Sci.* 63:357-363.
Bae, J. M., M. Giroux, L. C. Hannah (1990) "Cloning And Characterization Of The Brittle-2 Gene Of Maize" *Maydica* 35:317-322.
Ballicora, M. A., Laughlin, M. J., Fu, Y., Okita, T. W., Barry, G. F., Preiss, J. (1995) "Adenosine 5'-Diphosphate-Glucose Pyrophosphorylase from Potato Tuber" *Plant Physiol.* 109:245-251.
Ballicora, M. A., Fu, Y., Frueauf, J. B., Preiss, J. (1999) "Heat Stability of the Potato Tuber ADP-Glucose Pyrophosphorylase: Role of Cys Residue 12 in the Small Subunit" *Biochem. Biophys. Res. Comm.* 257:782-786.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.
Bhave, M. R., S. Lawrence, C. Barton, L. C. Hannah (1990) "Identification and Molecular Characterization of Shrunken-2 cDNA Clones of Maize" *Plant Cell* 2:581-588.
Burger, B. T., Cross J. M., Shaw, J. R., Caren, J. R., Greene, T. W., Okita, T. W., Hannah, L. C. (2003) "Relative turnover numbers of maize endosperm and potato tuber ADP-glucose pyrophosphorylases in the absence and presence of 3-PGA" *Planta* 217:449-456.
Chang, J. (1981) "Corn Yield In Relation To Photoperiod, Night Temperature, And Solar Radiation" *Agricul. Metero.* 24:253-262.
Cheikh, N., Jones, R. J. (1995) "Heat Stress Effects on Sink Activity of Developing Maize Kernels Grown In Vitro" *Physiol. Plant.* 95:59-66.
Clancy, M. and Hannah, L. C. (2002) "Splicing of the maize Sh1 first intron is essential for enhancement of gene expression, and a T-rich motif increases expression without affecting splicing," *Plant Physiol.* 130(2):918-29.
Conroy, J. P., Seneweera, S., Basra, A. S., Rogers, G., and Nissen-Wooller, B. (1994) "Influence of Rising Atmospheric $CO_2$ Concentrations and Temperature on Growth, Yield and Grain Quality of Cereal Crops" *Aust. J. Plant Physiol.* 21:741-758.
Copeland, L., J. Preiss (1981) "Purification of Spinach Leaf ADP glucose Pyrophosphorylase" *Plant Physiol.* 68:996-1001.
de Boer, H. A., Comstock, L. J., Vasser, M. (1983) "The tac promoter: a functional hybrid derived from the trp and lac promoters" *Proc. Natl. Acad. Sci. USA* 80(1):21-25.
Denyer, K., Hylton, C. M., Smith, A. M. (1994) "The Effect of High Temperature on Starch Synthesis and the Activity of Starch Synthase" *Aust. J. Plant Physiol.* 21:783-789.
Dickinson, D. B., J. Preiss (1969) "Presence of ADP-Glucose Pyrophosphorylase in Shrunken-2 and Brittle-2 Mutants of Maize Endosperm" *Plant Physiol.* 44:1058-1062.
Duke, E. R. Doehlert, D. C. (1996) "Effects of heat stress on enzyme activities and transcript levels in developing maize kernels grown in culture" *Environ. Exp. Botany.* 36:199-208.
Giroux, M. J., Shaw, J., Barry, G., Cobb, G. B., Greene, T., Okita, T. W., Hannah, L. C. (1996) "A Single Gene Mutation That Increases Maize Seed Weight" *Proc. Natl. Acad. Sci.* 93:5824-5829.

Greene, T. W., Chantler, S. E., Kahn, M. L., Barry, G. F., Preiss, J., Okita, T. W. (1996a) "Mutagenesis of the Potato ADP glucose Pyrophosphorylase and Characterization of an Allosteric Mutant Defective in 3-phosphoglycerate Activation" *Proc. Natl. Acad. Sci.* 93:1509-1513.

Greene, T. W., Woodbury, R. L., Okita, T. W. (1996b) "Aspartic Acid 413 Is Important for the Normal Allosteric Functioning of ADP-Glucose Pyrophosphorylase" *Plant Physiol.* 112:1315-1320.

Greene, T. W., Hannah, L. C. (1998) "Enhanced stability of maize endosperm ADP-glucose pyrophosphorylase is gained through mutants that alter subunit interactions" *Proc. Natl. Acad. Sci. USA* 95: 13342-13347.

Hannah, L. C., Tuschall, D. M., Mans, R. J. (1980) "Multiple forms of maize endosperm ADP-glucose pyrophosphorylase and their control of shrunken-2 and brittle-2" *Genetics* 95:961-970.

Hannah, L. Curtis (1996) "Starch synthesis in the maize endosperm," In: *Advances in Cellular and Molecular Biology of Plants*, Vol. 4. B. A. Larkins and I. K. Vasil (eds.). Cellular and Molecular Biology of Plant Seed Development. Kluwer Academic Publishers, Dordrecht, The Netherlands.

Hannah, L. C., O. E. Nelson (1975) "Characterization of Adenosine Diphosphate Glucose Pyrophosphorylases from Developing Maize Seeds" *Plant Physiol.* 55:297-302.

Hannah, L. C., Nelson, Jr., O. E. (1976) "Characterization of ADP-Glucose Pyrophosphorylase from Shrunken-2 and Brittle-2 Mutants of Maize" *Biochem. Genet.* 14:547-560.

Hannah, L. C., Shaw, J. R., Giroux, M., Reyss, A., Prioul, J.-L. Bae, J.-M., Lee, J.-Y. (2001) "Maize genes encoding the small subunit of ADP-glucose pyrophosphorylase" *Plant Physiol.* 127:173-183.

Hawker, J. S. and Jenner, C. F. (1993) "High Temperature Affects the Activity of Enzymes in the Committed Pathway of Starch Synthesis in Developing Wheat Endosperm" *Aust. J. Plant Physiol.* 20:197-209.

Horton, Robert M., Ho, Steffan H., Pullen, Jeffery K., Hunt, Henry D., Cai, Zeling, Pease, Larry R. (1993) "Gene Splicing by Overlap Extension" In Wu, Ray ed, Methods of Enzymology: Recombinant DNA, part H, volume 217. Academic Press, New York, pp 270-279.

Hunter, R. B., Tollenaar, M., Breuer, C. M. (1977) *Can. J. Plant Sci.* 57:1127-1133.

Iglesias, A., Barry, G. F., Meyer, C., Bloksberg, L., Nakata, P., Greene, T., Laughlin, M. J., Okita, T. W., Kishore, G. M., Preiss, J. (1993) "Expression of the Potato Tuber ADP-glucose Pyrophosphorylase in *Escherichia coli*" *J. Biol Chem.* 268:1081-86

Jenner, C. F. (1994) "Starch Synthesis in the Kernel of Wheat Under High Temperature Conditions" *Aust. J. Plant Physiol.* 21:791-806.

Jenner, C. F., Denyer, K., Guerin, J. (1995) "Thermal Characteristics of Soluble Starch Synthase from Wheat Endosperm" *Aust. J. Plant Physiol.* 22:703-709.

Jones, R. J., Gengenbach, B. G., and Cardwell, V. B. (1981) "Temperature Effects On In Vitro Kernel Development of Maize" *Crop Science* 21:761-766.

Jones, R. J., Ouattar, S., and Crookston, R. K. (1984) "Thermal Environment During Endosperm Cell Division And Grain Filling In Maize: Effects On Kernel Growth And Development In Vitro" *Crop Science* 24:133-137.

Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.

Karlin S. and Altschul, S. F. (1993) "Applications and Statistics for Multiple High-Scoring Segments in Molecular Sequences" *Proc. Natl. Acad. Sci. USA* 90:5873-5877.

Keeling, P. L., Bacon, P. J., Holt, D. C. (1993) "Elevated Temperature Reduces Starch Deposition in Wheat Endosperm by Reducing the Activity of Soluble Starch Synthase" *Planta.* 191:342-348.

Kleczhowski, L. A., Villand, P., Luthi E., Olsen, O. A., Preiss, J. (1993) "Insensitivity of barley endosperm ADP-glucose pyrophosphorylase to 3-phosphoglycerate and orthophosphate regulation" *Plant Physiol.* 101(1):179-86.

Lin, T., Caspar, T., Sommerville, C. R., Preiss, J. (1988) "A Starch Deficient Mutant of *Arabidopsis thaliana* with Low ADP glucose Pyrophosphorylase Activity Lacks One of the Two Subunits of the Enzyme" *Plant Physiol.* 88:1175-1181.

Maniatis, T., E. F. Fritsch, J. Sambrook (1982) "Nuclease Bal31" *Molecular Cloning: A Laboratory Manual*, Cold Spring Harbor Laboratory, Cold Spring Harbor, N.Y.

Morell, M., M. Bloon, V. Knowles, J. Preiss (1988) "Affinity Labeling of the Allosteric Activator Site(s) of Spinach Leaf ADP-glucose Pyrophosphorylase" *J. Bio. Chem.* 263:633.

Muller-Rober, B. T., J. Kossmann, L. C. Hannah, L. Willmitzer, U. Sounewald (1990) "One of Two Different ADP-glucose Pyrophosphorylase Genes From Potato Responds Strongly to Elevated Levels of Sucrose" *Mol. Gen. Genet.* 224:136-146.

Nakata, P. A., T. W. Greene, J. M. Anderson, B. J. Smith-White, T. W. Okita, J. Preiss (1991) "Comparison of the Primary Sequences of Two Potato Tuber ADP-glucose Pyrophosphorylase Subunits" *Plant Mol. Biol.* 17:1089-1093.

Okita, T. W., Nakata, P. A., Anderson, J. M., Sowokinos, J., Morell, J., Preiss, J. (1990) "The Subunit Structure of Potato Tuber ADP glucose Pyrophosphorylase" *Plant Physiol.* 93:785-90.

Okita, T. W., Greene, T. W., Laughlin, M. J., Salamone, P., Woodbury, R., Choi, S., Ito, H., Kavakli, H., Stephens, K. (1996) "Engineering Plant Starches by the Generation of Modified Plant Biosynthetic Enzymes," In *Engineering Crops for Industrial End Uses*, Shewry, P. R., Napier, J. A., and Davis, P., eds., Portland Press Ltd., London.

Olive, M. R., R. J. Ellis, W. W. Schuch (1989) "Isolation and Nucleotide Sequences of cDNA Clones Encoding ADP-glucose Pyrophosphorylase Polypeptides from Wheat Leaf and Endosperm" *Plant Physiol. Mol. Biol.* 12:525-538.

Ou-Lee, T. and Setter, T. L. (1985) "Effect of Increased Temperature in Apical Regions of Maize Ears on Starch-Synthesis Enzymes and Accumulation of Sugars and Starch" *Plant Physiol.* 79:852-855.

Preiss, J. (1984) "Bacterial Glycogen Synthesis and Its Regulation" *Ann. Rev. Microbiol.* 38:419-458.

Preiss, J. and Romeo, T. (1994) "Molecular Biology and Regulatory Aspects of Glycogen Biosynthesis in Bacteria" *Progress in Nuc. Acid Res. and Mol Biol.* 47:299-29.

Preiss, J. and Sivak, M. (1996) "Starch synthesis in sinks and sources," In *Photoassimilate distribution in plants and crops: source-sink relationships*. Zamski, E., ed., Marcil Dekker Inc. pp. 139-168.

Rijven, A. H. G. C. (1986) "Heat Inactivation of Starch Synthase in Wheat Endosperm Tissue" *Plant Physiol.* 81:448-453.

Shaw, J. R., Hannah, L. C. (1992) "Genomic Nucleotide Sequence of a Wild-Type Shrunken-2 Allele of *Zea mays*" *Plant Physiology* 98:1214-1216.

Singletary, G. W., Banisadr, R., Keeling, P. L. (1993) "Decreased starch synthesis in heat stressed maize kernels results from reduced ADPG-pyrophosphorylase and starch synthase activities" *Plant Physiol.* 102: 6 (suppl).

Singletary, G. W., Banisadra, R., Keeling, P. L. (1994) "Heat stress during grain filling in maize: effects of carbohydrate storage and metabolism" *Aust. J. Plant Physiol.* 21:829-841.

Smith-White, B. J. et al. (1992) "Comparison of Proteins of ADP-Glucose Pyrophosphorylase from Diverse Sources" *J. Mol. Evol.* 34:449-464.

Sowokinos, J. R., Preiss, J. (1982) "Pyrophosphorylases in *Solanum tuberosum*" *Plant Physiol.* 69:1459-1466.

Stark et al. (1992) "Regulation of the Amount of Starch in Plant Tissues by ADP Glucose Pyrophosphorylase" *Science* 258:287-292.

Thompson, L. M. (1986) "Climatic Change, Weather Variability, and Corn Production" *Agron. J.* 78:649-653.

Thompson, L. M. (1975) "Weather Variability, Climatic Change, and Grain Production" *Science* 188:535-541.

Tollenaar, M., Bruulsema, T. W. (1988) "Effects Of Temperature On Rate And Duration Of Kernel Dry Matter Accumulation Of Maize" *Can. J. Plant Sci.* 68:935-940.

Tsai, C. Y., Nelson, Jr., O. E. (1966) "Starch-Deficient Maize Mutant Lacking Adenosine Diphosphate Glucose Pyrophosphorylase Activity" *Science* 151:341-343.

Wilhelm, E. P., Mullen, R. E., Keeling, P. L., Singletary, G. W. (1999) "Heat stress during grain filling in maize: Effects on kernel growth and metabolism" *Crop Science* 39:1733-1741.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

Yang, T. T. et al. (1996) "Optimized Codon Usage and Chromophore Mutations Provide Enhanced Sensitivity with the Green Fluorescent Protein" *Nucleic Acid Research* 24(22): 4592-4593.

We claim:

1. A polynucleotide comprising a polynucleotide sequence encoding a mutant small subunit of a heat labile plant ADP glucose pyrophosphorylase (AGP) enzyme, or a fragment thereof, wherein said small subunit, or said fragment thereof, comprises a mutation in the N-terminal portion thereof wherein the amino acid corresponding to tyrosine at position 36 of wild type maize endosperm small subunit sequence is replaced by a cysteine, and wherein when said mutant small subunit, or said fragment thereof, is expressed with a large subunit of a plant AGP enzyme to form a mutant enzyme, said mutant enzyme exhibits increased heat stability when compared to a wild type form of maize endosperm AGP enzyme.

2. The polynucleotide according to claim 1, wherein said mutant small subunit, or said fragment thereof, is a maize endosperm AGP subunit.

3. The polynucleotide according to claim 2, wherein said mutant small subunit comprises the amino acid sequence shown in SEQ ID NO:4.

4. The polynucleotide according to claim 3, wherein said polynucleotide comprises the nucleotide sequence shown in SEQ ID NO:3.

5. The polynucleotide according to claim 2, wherein said mutant small subunit, or said fragment thereof, comprises a further mutation wherein an amino acid is inserted between the serine amino acid at position 34 and the threonine amino acid at position 35 of the wild type maize endosperm AGP small subunit sequence.

6. The polynucleotide according to claim 5, wherein the inserted amino acid is a glutamine.

7. The polynucleotide according to claim 6, wherein said mutant small subunit comprises the amino acid sequence shown in SEQ ID NO:8.

8. The polynucleotide according to claim 7, wherein said polynucleotide comprises the nucleotide sequence shown in SEQ ID NO:7.

9. The polynucleotide according to claim 5, wherein the inserted amino acid is a glutamic acid.

10. The polynucleotide according to claim 9, wherein said mutant small subunit comprises the amino acid sequence shown in SEQ ID NO:10.

11. The polynucleotide according to claim 10, wherein said polynucleotide comprises the nucleotide sequence shown in SEQ ID NO:9.

12. The polynucleotide according to claim 1, wherein said polynucleotide comprises a polynucleotide sequence encoding a large subunit of a plant AGP enzyme.

13. The polynucleotide according to claim 12, wherein said large subunit comprises a mutation that confers increased heat stability on an AGP enzyme or increased individual seed weight on a plant that comprises said large subunit.

14. The polynucleotide according to claim 13, wherein said large subunit comprises a heat stability (HS) mutation selected from the group consisting of HS13, HS14, HS16, HS33, HS40, HS47, HS RTS 48-2, HS RTS 60-1, HS33F, HS33M, HS7+3, HS6+3, HS7+6, and HS7+6+3.

15. A method for increasing resistance of a plant to heat stress conditions, said method comprising incorporating the polynucleotide of claim 1 into the genome of a plant and expressing the mutant small subunit AGP enzyme encoded by said polynucleotide, thereby increasing resistance of the plant to heat stress conditions.

16. The method according to claim 15, wherein said plant is a monocotyledonous plant.

17. The method according to claim 16, wherein said monocotyledonous plant is selected from the group consisting of rice, wheat, barley, oats, sorghum, maize, lily, and millet.

18. The method according to claim 16, wherein said plant is *Zea mays*.

19. The method according to claim 15, wherein said plant is a dicotyledonous plant.

20. The method according to claim 19, wherein said dicotyledonous plant is selected from the group consisting of pea, alfalfa, chickpea, chicory, clover, kale, lentil, soybean, tobacco, potato, sweet potato, radish, cabbage, rape, apple tree, and lettuce.

21. The method according to claim 15, wherein said plant comprises or expresses a large subunit of a plant AGP enzyme, wherein said large subunit comprises an amino acid mutation that confers increased heat stability or increased individual seed weight to a plant comprising or expressing said large subunit.

22. A plant, plant tissue or cell comprising a polynucleotide comprising a polynucleotide sequence encoding a mutant small subunit of a heat labile plant ADP glucose pyrophosphorylase (AGP) enzyme, or a fragment thereof, wherein said small subunit, or said fragment thereof, comprises a mutation in the N-terminal portion thereof wherein the amino acid corresponding to tyrosine at position 36 of wild type maize endosperm small subunit sequence is replaced by a cysteine, and wherein when said mutant small subunit, or said fragment thereof, is expressed with a large subunit of a plant AGP enzyme to form a mutant enzyme, said mutant enzyme exhibits increased heat stability when compared to a wild type form of maize endosperm AGP enzyme.

23. The plant, plant tissue or cell according to claim 22, wherein said plant, plant tissue or cell is monocotyledonous.

24. The plant, plant tissue or cell according to claim 23, wherein said monocotyledonous plant, plant tissue or cell is selected from the group consisting of rice, wheat, barley, oats, sorghum, maize, lily, and millet.

25. The plant, plant tissue or cell according to claim 22, wherein said plant is *Zea mays* or said plant tissue or cell is from *Zea mays*.

26. The plant, plant tissue or cell according to claim 22, wherein said plant, plant tissue or cell is dicotyledonous.

27. The plant, plant tissue or cell according to claim 26, wherein said dicotyledonous plant, plant tissue or cell is selected from the group consisting of pea, alfalfa, chickpea, chicory, clover, kale, lentil, soybean, tobacco, potato, sweet potato, radish, cabbage, rape, apple tree, and lettuce.

28. The plant, plant tissue or cell according to claim 22, wherein said plant tissue is a seed.

29. The plant, plant tissue or cell according to claim 22, wherein said plant, plant tissue or cell comprises or expresses a large subunit of a plant AGP enzyme, wherein said large subunit comprises an amino acid mutation that confers increased heat stability or increased individual seed weight to a plant comprising or expressing said large subunit.

30. A composition comprising:
i) a polynucleotide comprising a polynucleotide sequence encoding a mutant small subunit of a heat labile plant ADP glucose pyrophosphorylase (AGP) enzyme, or a fragment thereof, wherein said small subunit, or said fragment thereof, comprises a mutation in the N-terminal portion thereof wherein the amino acid corresponding to tyrosine at position 36 of wild type maize endosperm small subunit sequence is replaced by a cysteine, and wherein when said mutant small subunit, or said fragment thereof, is expressed with a large subunit of a plant AGP enzyme to form a mutant enzyme, said mutant enzyme exhibits increased heat stability when compared to a wild type form of maize endosperm AGP enzyme; and
ii) a polynucleotide comprising a polynucleotide sequence that encodes a large subunit of a plant AGP enzyme.

31. The composition according to claim 30, wherein said large subunit comprises a mutation that confers increased heat stability on an AGP enzyme or increased individual seed weight on a plant that comprises said large subunit.

32. The composition according to claim 31, wherein said large subunit comprises a heat stability (HS) mutation selected from the group consisting of HS13, HS14, HS16, HS33, HS40, HS47, HS RTS 48-2, HS RTS 60-1, HS33F, HS33M, HS7+3, HS6+3, HS7+6, and HS7+6+3.

33. A method for preparing a plant having an AGP enzyme that exhibits increased stability relative to a wild type AGP enzyme said method comprising introducing a polynucleotide as defined in claim 1 into a plant cell and growing a plant from said plant cell; or breeding a plant comprising a polynucleotide as defined in claim 1 with another plant of the same species and obtaining progeny that comprise said polynucleotide.

34. The method according to claim 33, wherein said plant grown from said plant cell is selected for expression of said polynucleotide.

35. The method according to claim 33, wherein said plant is a monocotyledonous plant.

36. The method according to claim 17, wherein said monocotyledonous plant is selected from the group consisting of rice, wheat, barley, oats, sorghum, maize, lily, and millet.

37. The method according to claim 33, wherein said plant is *Zea mays*.

38. The method according to claim 33, wherein said plant is a dicotyledonous plant.

39. The method according to claim 38, wherein said dicotyledonous plant is selected from the group consisting of pea, alfalfa, chickpea, chicory, clover, kale, lentil, soybean, tobacco, potato, sweet potato, radish, cabbage, rape, apple tree, and lettuce.

40. The method according to claim 33, wherein said plant comprises or expresses a large subunit of a plant AGP enzyme, wherein said large subunit comprises an amino acid mutation that confers increased heat stability or increased individual seed weight to a plant comprising or expressing said large subunit.

41. An expression construct comprising a polynucleotide comprising a polynucleotide sequence encoding a mutant small subunit of a heat labile plant ADP glucose pyrophosphorylase (AGP) enzyme, or a fragment thereof, wherein said small subunit, or said fragment thereof, comprises a mutation in the N-terminal portion thereof wherein the amino acid corresponding to tyrosine at position 36 of wild type maize endosperm small subunit sequence is replaced by a cysteine, and wherein when said mutant small subunit, or said fragment thereof, is expressed with a large subunit of a plant AGP enzyme to form a mutant enzyme, said mutant enzyme exhibits increased heat stability when compared to a wild type form of maize endosperm AGP enzyme.

42. The composition according to claim 30, wherein said mutant small subunit, or said fragment thereof, is a maize endosperm AGP subunit.

43. The composition according to claim 42, wherein said mutant small subunit comprises the amino acid sequence shown in SEQ ID NO:4.

44. The composition according to claim 43, wherein said polynucleotide comprises the nucleotide sequence shown in SEQ ID NO:3.

45. The composition according to claim 42, wherein said mutant small subunit, or said fragment thereof, comprises a further mutation wherein an amino acid is inserted between the serine amino acid at position 34 and the threonine amino acid at position 35 of the wild type maize endosperm AGP small subunit sequence.

46. The composition according to claim 45, wherein the inserted amino acid is a glutamine.

47. The composition according to claim 46, wherein said mutant small subunit comprises the amino acid sequence shown in SEQ ID NO:8.

48. The composition according to claim 47, wherein said polynucleotide comprises the nucleotide sequence shown in SEQ ID NO:7.

49. The composition according to claim 45, wherein the inserted amino acid is a glutamic acid.

50. The composition according to claim 49, wherein said mutant small subunit comprises the amino acid sequence shown in SEQ ID NO:10.

51. The composition according to claim 50, wherein said polynucleotide comprises the nucleotide sequence shown in SEQ ID NO:9.

52. The polynucleotide according to claim 1, wherein said polynucleotide comprises complementary deoxyribonucleic acid (cDNA).

53. The method according to claim 15, wherein said polynucleotide comprises complementary deoxyribonucleic acid (cDNA).

54. The plant, plant tissue or cell according to claim 22, wherein said polynucleotide comprises complementary deoxyribonucleic acid (cDNA).

55. The composition according claim 30, wherein said polynucleotide comprises complementary deoxyribonucleic acid (cDNA).

56. The method according claim 33, wherein said polynucleotide comprises complementary deoxyribonucleic acid (cDNA).

57. The expression construct according claim 41, wherein said polynucleotide comprises complementary deoxyribonucleic acid (cDNA).

* * * * *

UNITED STATES PATENT AND TRADEMARK OFFICE
CERTIFICATE OF CORRECTION

PATENT NO. : 8,710,298 B2
APPLICATION NO. : 10/569000
DATED : April 29, 2014
INVENTOR(S) : L. Curtis Hannah and Carla R. Linebarger It is certified that error appears in the above-identified patent and that said Letters Patent is hereby corrected as shown below:

In the Specification

Column 14,
Lines 18-19, "151, 12," should read --151, 152,--

Column 24,
Line 31, "1.2 × 106" should read --1.2 × $10^6$--
Line 31, "1.3 × 106" should read --1.3 × $10^6$--
Line 37, "1.4 × 106" should read --1.4 × $10^6$--
Line 37, "3.4 × 106" should read --3.4 × $10^6$--

Column 28,
Line 55, "47:299-29" should read --47:299-329--

In the Claims

Column 167,
Claim 18, Line 24, "claim 16" should read --claim 15--

Signed and Sealed this
Seventh Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,710,298 B2  Page 1 of 1
APPLICATION NO. : 10/569000
DATED : April 29, 2014
INVENTOR(S) : Hannah et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1023 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 44

<210> SEQ ID NO 1
<211> LENGTH: 1425
<212> TYPE: DNA
<213> ORGANISM: zea mays

<400> SEQUENCE: 1
atggacatgg ctttggcgtc taaagcctcc cctccgccat ggaatgccac cgccgccgag      60
cagccaattc aaagcgtga caaagccgct gcaaatgatt caacatacct caatcctcaa     120
gctcatgata gtgttcttgg aatcattctg ggaggtggtg ctgggactag attgtacccc     180
ttgacaaaga agcgtgccaa gcctgcagtg ccattgggtg ccaactatag actgattgat     240
attcctgtca gcaattgtct caacagcaac atatccaaga tctatgtgct aacgcaatt     300 aactctgctt ccctcaaccg tcacctctca agagcctacg ggagcaacat tggagggtac     360
aagaatgaag ggtttgttga agtcttagct gcacagcaga gcccagataa tccaaactgg     420
tttcagggta ctgcagatgc tgtaaggcag tacttgtggt tgtttgagga gcataatgtg     480
atggaatttc taattcttgc tggcgatcac ctgtaccgga tggactatga aaagttcatt     540
caggcacaca gagaaacaaa tgctgatatt accgttgctg ccctaccgat ggatgagaaa     600
cgtgcaactg catttggcct catgaaaatt gatgaagaag ggaggatcat tgagtttgct     660
gagaaaccga aaggagagca gttgaaagca atgatggtta caccaccat acttggcctt     720 gatgacgtga gggcaaagga aatgccttat attgctagca tgggtatcta tgtttttcagc     780 aaagatgtaa tgcttcagct cctccgtgaa caatttcctg aagccaatga ctttggaagt     840
gaggttattc caggtgcaac cagcattgga aagagggttc aggcttatct gtatgatggt     900
tactgggaag atatcggtac cattgcggca ttttataatg caaacttggg aataaccaag     960
aagccaatac cagatttcag cttctatgac cgtttgctc caatttatac acaacctcga    1020
cacctgccac cttcaaaggt tcttgatgct gatgtgacac agtgttat tggtgaagga    1080 tgtgttatta aaaactgcaa gataaaccat tctgtagttg gactccgatc ttgcatatct    1140
gaaggtgcta tcatagagga cagtttacta atgggtgcgg actactatga gacagaagct    1200
gataaaaaac tccttgccga aaaggtggc attcctattg gtattgggaa aaattcatgc    1260
atcaggagag caatcattga caagaatgct cgaattggag acaatgttaa gatactcaat    1320
gctgacaatg ttcaagaagc tgcaatggag acagacgggt acttcatcaa aggtggaatt    1380
```

```
gtcacagtga tcaaggatgc tttactccct agtggaacag ttata              1425
```

<210> SEQ ID NO 2
<211> LENGTH: 475
<212> TYPE: PRT
<213> ORGANISM: zea mays

<400> SEQUENCE: 2

| Met | Asp | Met | Ala | Leu | Ala | Ser | Lys | Ala | Ser | Pro | Pro | Trp | Asn | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Thr Ala Ala Glu Gln Pro Ile Pro Lys Arg Asp Lys Ala Ala Asn
                20                  25                  30

Asp Ser Thr Tyr Leu Asn Pro Gln Ala His Asp Ser Val Leu Gly Ile
            35                  40                  45

Ile Leu Gly Gly Gly Ala Gly Thr Arg Leu Tyr Pro Leu Thr Lys Lys
 50                  55                  60

Arg Ala Lys Pro Ala Val Pro Leu Gly Ala Asn Tyr Arg Leu Ile Asp
 65                  70                  75                  80

Ile Pro Val Ser Asn Cys Leu Asn Ser Asn Ile Ser Lys Ile Tyr Val
                 85                  90                  95

Leu Thr Gln Phe Asn Ser Ala Ser Leu Asn Arg His Leu Ser Arg Ala
            100                 105                 110

Tyr Gly Ser Asn Ile Gly Gly Tyr Lys Asn Glu Gly Phe Val Glu Val
                115                 120                 125

Leu Ala Ala Gln Gln Ser Pro Asp Asn Pro Asn Trp Phe Gln Gly Thr
    130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
            180                 185                 190

Ala Ala Leu Pro Met Asp Glu Lys Arg Ala Thr Ala Phe Gly Leu Met
        195                 200                 205

Lys Ile Asp Glu Glu Gly Arg Ile Ile Glu Phe Ala Glu Lys Pro Lys
210                 215                 220

Gly Glu Gln Leu Lys Ala Met Met Val Asp Thr Thr Ile Leu Gly Leu
225                 230                 235                 240

Asp Asp Val Arg Ala Lys Glu Met Pro Tyr Ile Ala Ser Met Gly Ile
                245                 250                 255

Tyr Val Phe Ser Lys Asp Val Met Leu Gln Leu Leu Arg Glu Gln Phe
            260                 265                 270

Pro Glu Ala Asn Asp Phe Gly Ser Glu Val Ile Pro Gly Ala Thr Ser
        275                 280                 285

Ile Gly Lys Arg Val Gln Ala Tyr Leu Tyr Asp Gly Tyr Trp Glu Asp
    290                 295                 300

Ile Gly Thr Ile Ala Ala Phe Tyr Asn Ala Asn Leu Gly Ile Thr Lys
305                 310                 315                 320

Lys Pro Ile Pro Asp Phe Ser Phe Tyr Asp Arg Phe Ala Pro Ile Tyr
                325                 330                 335

Thr Gln Pro Arg His Leu Pro Pro Ser Lys Val Leu Asp Ala Asp Val
            340                 345                 350

Thr Asp Ser Val Ile Gly Glu Gly Cys Val Ile Lys Asn Cys Lys Ile
        355                 360                 365

```
Asn His Ser Val Val Gly Leu Arg Ser Cys Ile Ser Glu Gly Ala Ile
        370                 375                 380

Ile Glu Asp Ser Leu Leu Met Gly Ala Asp Tyr Tyr Glu Thr Glu Ala
385                 390                 395                 400

Asp Lys Lys Leu Leu Ala Glu Lys Gly Gly Ile Pro Ile Gly Ile Gly
                405                 410                 415

Lys Asn Ser Cys Ile Arg Arg Ala Ile Ile Asp Lys Asn Ala Arg Ile
                420                 425                 430

Gly Asp Asn Val Lys Ile Leu Asn Ala Asp Asn Val Gln Glu Ala Ala
            435                 440                 445

Met Glu Thr Asp Gly Tyr Phe Ile Lys Gly Gly Ile Val Thr Val Ile
        450                 455                 460

Lys Asp Ala Leu Leu Pro Ser Gly Thr Val Ile
465                 470                 475

<210> SEQ ID NO 3
<211> LENGTH: 1425
<212> TYPE: DNA
<213> ORGANISM: zea mays

<400> SEQUENCE: 3
atggacatgg ctttggcgtc taaagcctcc cctccgccat ggaatgccac cgccgccgag      60
cagccaattc aaagcgtga caaagccgct gcaaatgatt caacatgyct caatcctcaa     120
gctcatgata gtgttcttgg aatcattctg ggaggtggtg ctgggactag attgtacccc     180
ttgacaaaga agcgtgccaa gcctgcagtg ccattgggtg ccaactatag actgattgat     240
attcctgtca gcaattgtct caacagcaac atatccaaga tctatgtgct aacgcaattt     300
aactctgctt ccctcaaccg tcacctctca agagcctacg ggagcaacat tggagggtac     360
aagaatgaag ggtttgttga agtcttagct gcacagcaga gcccagataa tccaaactgg     420
tttcagggta ctgcagatgc tgtaaggcag tacttgtggt tgtttgagga gcataatgtg     480
atggaatttc taattcttgc tggcgatcac ctgtaccgga tggactatga aaagttcatt     540
caggcacaca gagaaacaaa tgctgatatt accgttgctg ccctaccgat ggatgagaaa     600
cgtgcaactg catttggcct catgaaaatt gatgaagaag ggaggatcat tgagtttgct     660
gagaaaccga aggagagca gttgaaagca atgatggttg acaccaccat acttggcctt     720
gatgacgtga gggcaaagga aatgccttat attgctagca tgggtatcta tgttttcagc     780
aaagatgtaa tgcttcagct cctccgtgaa caatttcctg aagccaatga ctttggaagt     840
gaggttattc caggtgcaac cagcattgga aagagggttc aggcttatct gtatgatggt     900
tactgggaag atatcggtac cattgcggca ttttataatg caaacttggg aataaccaag     960
aagccaatac cagatttcag cttctatgac cgttttgctc aatttataca caacctcga    1020
cacctgccac cttcaaaggt tcttgatgct gatgtgacag acagtgttat tggtgaagga    1080
tgtgttatta aaaactgcaa gataaaccat tctgtagttg gactccgatc ttgcatatct    1140
gaaggtgcta tcatagagga cagtttacta atgggtgcgg actactatga gacagaagct    1200
gataaaaac tccttgccga aaaggtggc attcctattg gtattgggaa aaattcatgc    1260
atcaggagag caatcattga caagaatgct cgaattggag acaatgttaa gatactcaat    1320
gctgacaatg ttcaagaagc tgcaatggag acagacgggt acttcatcaa aggtggaatt    1380
gtcacagtga tcaaggatgc tttactccct agtggaacag ttata            1425

<210> SEQ ID NO 4
<211> LENGTH: 475
```

```
<212> TYPE: PRT
<213> ORGANISM: zea mays

<400> SEQUENCE: 4

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Asn
                20                  25                  30

Asp Ser Thr Cys Leu Asn Pro Gln Ala His Asp Ser Val Leu Gly Ile
            35                  40                  45

Ile Leu Gly Gly Gly Ala Gly Thr Arg Leu Tyr Pro Leu Thr Lys Lys
    50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
            100                 105                 110

Tyr Gly Ser Asn Ile Gly Gly Tyr Lys Asn Glu Gly Phe Val Glu Val
        115                 120                 125

Leu Ala Ala Gln Gln Ser Pro Asp Asn Pro Asn Trp Phe Gln Gly Thr
130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
            180                 185                 190

Ala Ala Leu Pro Met Asp Glu Lys Arg Ala Thr Ala Phe Gly Leu Met
        195                 200                 205

Lys Ile Asp Glu Glu Gly Arg Ile Ile Glu Phe Ala Glu Lys Pro Lys
210                 215                 220

Gly Glu Gln Leu Lys Ala Met Met Val Asp Thr Thr Ile Leu Gly Leu
225                 230                 235                 240

Asp Asp Val Arg Ala Lys Glu Met Pro Tyr Ile Ala Ser Met Gly Ile
                245                 250                 255

Tyr Val Phe Ser Lys Asp Val Met Leu Gln Leu Leu Arg Glu Gln Phe
            260                 265                 270

Pro Glu Ala Asn Asp Phe Gly Ser Glu Val Ile Pro Gly Ala Thr Ser
        275                 280                 285

Ile Gly Lys Arg Val Gln Ala Tyr Leu Tyr Asp Gly Tyr Trp Glu Asp
290                 295                 300

Ile Gly Thr Ile Ala Ala Phe Tyr Asn Ala Asn Leu Gly Ile Thr Lys
305                 310                 315                 320

Lys Pro Ile Pro Asp Phe Ser Phe Tyr Asp Arg Phe Ala Pro Ile Tyr
                325                 330                 335

Thr Gln Pro Arg His Leu Pro Pro Ser Lys Val Leu Asp Ala Asp Val
            340                 345                 350

Thr Asp Ser Val Ile Gly Glu Gly Cys Val Ile Lys Asn Cys Lys Ile
        355                 360                 365

Asn His Ser Val Val Gly Leu Arg Ser Cys Ile Ser Glu Gly Ala Ile
370                 375                 380

Ile Glu Asp Ser Leu Leu Met Gly Ala Asp Tyr Tyr Glu Thr Glu Ala
385                 390                 395                 400
```

```
Asp Lys Lys Leu Leu Ala Glu Lys Gly Gly Ile Pro Ile Gly Ile Gly
            405                 410                 415

Lys Asn Ser Cys Ile Arg Arg Ala Ile Ile Asp Lys Asn Ala Arg Ile
            420                 425                 430

Gly Asp Asn Val Lys Ile Leu Asn Ala Asp Asn Val Gln Glu Ala Ala
            435                 440                 445

Met Glu Thr Asp Gly Tyr Phe Ile Lys Gly Gly Ile Val Thr Val Ile
    450                 455                 460

Lys Asp Ala Leu Leu Pro Ser Gly Thr Val Ile
465             470                 475

<210> SEQ ID NO 5
<211> LENGTH: 1428
<212> TYPE: DNA
<213> ORGANISM: zea mays

<400> SEQUENCE: 5
atggacatgg ctttggcgtc taaagcctcc cctccgccat ggaatgccac cgccgccgag      60
cagccaattc caaagcgtga caaagccgct gcaaatgatt caacarcata cctcaatcct     120
caagctcatg atagtgttct tggaatcatt ctgggaggtg gtgctgggac tagattgtac     180
cccttgacaa gaagcgtgc caagcctgca gtgccattgg gtgccaacta tagactgatt     240
gatattcctg tcagcaattg tctcaacagc aacatatcca agatctatgt gctaacgcaa     300
tttaactctg cttccctcaa ccgtcacctc tcaagagcct acgggagcaa cattggaggg     360
tacaagaatg aagggtttgt tgaagtctta gctgcacagc agagcccaga taatccaaac     420
tggtttcagg gtactgcaga tgctgtaagg cagtacttgt ggttgtttga ggagcataat     480
gtgatggaat ttctaattct tgctggcgat cacctgtacc ggatggacta tgaaaagttc     540
attcaggcac acagagaaac aaatgctgat attaccgttg ctgccctacc gatggatgag     600
aaacgtgcaa ctgcatttgg cctcatgaaa attgatgaag aagggaggat cattgagttt     660
gctgagaaac cgaaaggaga gcagttgaaa gcaatgatgg ttgacaccac catacttggc     720
cttgatgacg tgagggcaaa ggaaatgcct tatattgcta gcatgggtat ctatgttttc     780
agcaaagatg taatgcttca gctcctccgt gaacaatttc ctgaagccaa tgactttgga     840
agtgaggtta ttccaggtgc aaccagcatt ggaaagaggg ttcaggctta tctgtatgat     900
ggttactggg aagatatcgg taccattgcg gcattttata tgcaaacttt gggaataacc     960
aagaagccaa taccagattt cagcttctat gaccgttttg ctccaattta cacacaacct    1020
cgacacctgc caccttcaaa ggttcttgat gctgatgtga cagacagtgt tattggtgaa    1080
ggatgtgtta ttaaaaactg caagataaac cattctgtag ttggactccg atcttgcata    1140
tctgaaggtg ctatcataga ggacagttta ctaatgggtg cggactacta tgagacagaa    1200
gctgataaaa aactccttgc cgaaaaaggt ggcattccta ttggtattgg gaaaaattca    1260
tgcatcagga gagcaatcat tgacaagaat gctcgaattg gagacaatgt taagatactc    1320
aatgctgaca atgttcaaga agctgcaatg gagacagacg gtacttcat caaaggtgga    1380 attgtcacag tgatcaagga tgctttactc cctagtggaa cagttata                1428

<210> SEQ ID NO 6
<211> LENGTH: 476
<212> TYPE: PRT
<213> ORGANISM: zea mays

<400> SEQUENCE: 6

Met Asp Met Ala Leu Ala Ser Lys Ala Ser Pro Pro Trp Asn Ala
```

```
1               5                   10                  15
Thr Ala Ala Glu Gln Pro Ile Pro Lys Arg Asp Lys Ala Ala Asn
                20                  25                  30

Asp Ser Gln Thr Tyr Leu Asn Pro Gln Ala His Asp Ser Val Leu Gly
        35                  40                  45

Ile Ile Leu Gly Gly Gly Ala Gly Thr Arg Leu Tyr Pro Leu Thr Lys
50                  55                  60

Lys Arg Ala Lys Pro Ala Val Pro Leu Gly Ala Asn Tyr Arg Leu Ile
65                  70                  75                  80

Asp Ile Pro Val Ser Asn Cys Leu Asn Ser Asn Ile Ser Lys Ile Tyr
                85                  90                  95

Val Leu Thr Gln Phe Asn Ser Ala Ser Leu Asn Arg His Leu Ser Arg
                100                 105                 110

Ala Tyr Gly Ser Asn Ile Gly Gly Tyr Lys Asn Glu Gly Phe Val Glu
                115                 120                 125

Val Leu Ala Ala Gln Gln Ser Pro Asp Asn Pro Asn Trp Phe Gln Gly
                130                 135                 140

Thr Ala Asp Ala Val Arg Gln Tyr Leu Trp Leu Phe Glu Glu His Asn
145                 150                 155                 160

Val Met Glu Phe Leu Ile Leu Ala Gly Asp His Leu Tyr Arg Met Asp
                165                 170                 175

Tyr Glu Lys Phe Ile Gln Ala His Arg Glu Thr Asn Ala Asp Ile Thr
                180                 185                 190

Val Ala Ala Leu Pro Met Asp Glu Lys Arg Ala Thr Ala Phe Gly Leu
                195                 200                 205

Met Lys Ile Asp Glu Glu Gly Arg Ile Ile Glu Phe Ala Glu Lys Pro
210                 215                 220

Lys Gly Glu Gln Leu Lys Ala Met Met Val Asp Thr Thr Ile Leu Gly
225                 230                 235                 240

Leu Asp Asp Val Arg Ala Lys Glu Met Pro Tyr Ile Ala Ser Met Gly
                245                 250                 255

Ile Tyr Val Phe Ser Lys Asp Val Met Leu Gln Leu Leu Arg Glu Gln
                260                 265                 270

Phe Pro Glu Ala Asn Asp Phe Gly Ser Glu Val Ile Pro Gly Ala Thr
                275                 280                 285

Ser Ile Gly Lys Arg Val Gln Ala Tyr Leu Tyr Asp Gly Tyr Trp Glu
                290                 295                 300

Asp Ile Gly Thr Ile Ala Ala Phe Tyr Asn Ala Asn Leu Gly Ile Thr
305                 310                 315                 320

Lys Lys Pro Ile Pro Asp Phe Ser Phe Tyr Asp Arg Phe Ala Pro Ile
                325                 330                 335

Tyr Thr Gln Pro Arg His Leu Pro Pro Ser Lys Val Leu Asp Ala Asp
                340                 345                 350

Val Thr Asp Ser Val Ile Gly Glu Gly Cys Val Ile Lys Asn Cys Lys
                355                 360                 365

Ile Asn His Ser Val Val Gly Leu Arg Ser Cys Ile Ser Glu Gly Ala
                370                 375                 380

Ile Ile Glu Asp Ser Leu Leu Met Gly Ala Asp Tyr Tyr Glu Thr Glu
385                 390                 395                 400

Ala Asp Lys Lys Leu Leu Ala Glu Lys Gly Ile Pro Ile Gly Ile
                405                 410                 415

Gly Lys Asn Ser Cys Ile Arg Arg Ala Ile Ile Asp Lys Asn Ala Arg
                420                 425                 430
```

```
Ile Gly Asp Asn Val Lys Ile Leu Asn Ala Asp Asn Val Gln Glu Ala
        435                 440                 445

Ala Met Glu Thr Asp Gly Tyr Phe Ile Lys Gly Ile Val Thr Val
        450                 455                 460

Ile Lys Asp Ala Leu Leu Pro Ser Gly Thr Val Ile
465                 470                 475

<210> SEQ ID NO 7
<211> LENGTH: 1428
<212> TYPE: DNA
<213> ORGANISM: zea mays

<400> SEQUENCE: 7
atggacatgg ctttggcgtc taaagcctcc cctccgccat ggaatgccac cgccgccgag      60
cagccaattc caaagcgtga caaagccgct gcaaatgatt caacarcatg yctcaatcct     120
caagctcatg atagtgttct tggaatcatt ctgggaggtg gtgctgggac tagattgtac     180
cccttgacaa agaagcgtgc caagcctgca gtgccattgg gtgccaacta tagactgatt     240
gatattcctg tcagcaattg tctcaacagc aacatatcca agatctatgt gctaacgcaa     300
tttaactctg cttccctcaa ccgtcacctc tcaagagcct acgggagcaa cattggaggg     360
tacaagaatg aagggtttgt tgaagtctta gctgcacagc agagcccaga taatccaaac     420
tggtttcagg gtactgcaga tgctgtaagg cagtacttgt ggttgtttga ggagcataat     480
gtgatggaat ttctaattct tgctggcgat cacctgtacc ggatggacta tgaaaagttc     540
attcaggcac acagagaaac aaatgctgat attaccgttg ctgccctacc gatgaatgag     600
aaacgtgcaa ctgcatttgg cctcatgaaa attgatgaag aagggaggat cattgagttt     660
gctgagaaac cgaaaggaga gcagttgaaa gcaatgatgg ttgacaccac catacttggc     720
cttgatgacg tgagggcaaa ggaaatgcct tatattgcta gcatgggtat ctatgttttc     780
agcaaagatg taatgcttca gctcctccgt gaacaatttc ctgaagccaa tgactttgga     840
agtgaggtta ttccaggtgc aaccagcatt ggaaagaggg ttcaggctta tctgtatgat     900
ggttactggg aagatatcgg taccattgcg gcatttttata atgcaaactt gggaataacc     960
aagaagccaa taccagattt cagcttctat gaccgttttg ctccaattta tacacaacct    1020
cgacacctgc caccttcaaa ggttcttgat gctgatgtga cagacagtgt tattggtgaa    1080
ggatgtgtta ttaaaaactg caagataaac cattctgtag ttggactccg atcttgcata    1140
tctgaaggtg ctatcataga ggacagttta ctaatgggtg cggactacta tgagacagaa    1200
gctgataaaa aactccttgc cgaaaaaggt ggcattccta ttggtattgg gaaaaattca    1260
tgcatcagga gagcaatcat tgacaagaat gctcgaattg agacaatgt taagatactc    1320
aatgctgaca atgttcaaga agctgcaatg gagacagacg ggtacttcat caaaggtgga    1380
attgtcacag tgatcaagga tgctttactc cctagtggaa cagttata              1428

<210> SEQ ID NO 8
<211> LENGTH: 476
<212> TYPE: PRT
<213> ORGANISM: zea mays

<400> SEQUENCE: 8

Met Asp Met Ala Leu Ala Ser Lys Ala Ser Pro Pro Trp Asn Ala
1               5                  10                  15

Thr Ala Ala Glu Gln Pro Ile Pro Lys Arg Asp Lys Ala Ala Asn
            20                  25                  30

Asp Ser Gln Thr Cys Leu Asn Pro Gln Ala His Asp Ser Val Leu Gly
```

-continued

```
                35                  40                  45
Ile Ile Leu Gly Gly Gly Ala Gly Thr Arg Leu Tyr Pro Leu Thr Lys
 50                  55                  60

Lys Arg Ala Lys Pro Ala Val Pro Leu Gly Ala Asn Tyr Arg Leu Ile
 65                  70                  75                  80

Asp Ile Pro Val Ser Asn Cys Leu Asn Ser Asn Ile Ser Lys Ile Tyr
                 85                  90                  95

Val Leu Thr Gln Phe Asn Ser Ala Ser Leu Asn Arg His Leu Ser Arg
                100                 105                 110

Ala Tyr Gly Ser Asn Ile Gly Gly Tyr Lys Asn Glu Gly Phe Val Glu
                115                 120                 125

Val Leu Ala Ala Gln Gln Ser Pro Asp Asn Pro Asn Trp Phe Gln Gly
130                 135                 140

Thr Ala Asp Ala Val Arg Gln Tyr Leu Trp Leu Phe Glu Glu His Asn
145                 150                 155                 160

Val Met Glu Phe Leu Ile Leu Ala Gly Asp His Leu Tyr Arg Met Asp
                165                 170                 175

Tyr Glu Lys Phe Ile Gln Ala His Arg Glu Thr Asn Ala Asp Ile Thr
                180                 185                 190

Val Ala Ala Leu Pro Met Asp Glu Lys Arg Ala Thr Ala Phe Gly Leu
                195                 200                 205

Met Lys Ile Asp Glu Glu Gly Arg Ile Ile Glu Phe Ala Glu Lys Pro
210                 215                 220

Lys Gly Glu Gln Leu Lys Ala Met Met Val Asp Thr Thr Ile Leu Gly
225                 230                 235                 240

Leu Asp Asp Val Arg Ala Lys Glu Met Pro Tyr Ile Ala Ser Met Gly
                245                 250                 255

Ile Tyr Val Phe Ser Lys Asp Val Met Leu Gln Leu Leu Arg Glu Gln
                260                 265                 270

Phe Pro Glu Ala Asn Asp Phe Gly Ser Glu Val Ile Pro Gly Ala Thr
                275                 280                 285

Ser Ile Gly Lys Arg Val Gln Ala Tyr Leu Tyr Asp Gly Tyr Trp Glu
290                 295                 300

Asp Ile Gly Thr Ile Ala Ala Phe Tyr Asn Ala Asn Leu Gly Ile Thr
305                 310                 315                 320

Lys Lys Pro Ile Pro Asp Phe Ser Phe Tyr Asp Arg Phe Ala Pro Ile
                325                 330                 335

Tyr Thr Gln Pro Arg His Leu Pro Pro Ser Lys Val Leu Asp Ala Asp
                340                 345                 350

Val Thr Asp Ser Val Ile Gly Glu Gly Cys Val Ile Lys Asn Cys Lys
                355                 360                 365

Ile Asn His Ser Val Val Gly Leu Arg Ser Cys Ile Ser Glu Gly Ala
                370                 375                 380

Ile Ile Glu Asp Ser Leu Leu Met Gly Ala Asp Tyr Tyr Glu Thr Glu
385                 390                 395                 400

Ala Asp Lys Lys Leu Leu Ala Glu Lys Gly Gly Ile Pro Ile Gly Ile
                405                 410                 415

Gly Lys Asn Ser Cys Ile Arg Arg Ala Ile Ile Asp Lys Asn Ala Arg
                420                 425                 430

Ile Gly Asp Asn Val Lys Ile Leu Asn Ala Asp Asn Val Gln Glu Ala
                435                 440                 445

Ala Met Glu Thr Asp Gly Tyr Phe Ile Lys Gly Gly Ile Val Thr Val
450                 455                 460
```

Ile Lys Asp Ala Leu Leu Pro Ser Gly Thr Val Ile
465                 470                 475

<210> SEQ ID NO 9
<211> LENGTH: 1428
<212> TYPE: DNA
<213> ORGANISM: zea mays

<400> SEQUENCE: 9

```
atggacatgg ctttggcgtc taaagcctcc cctccgccat ggaatgccac cgccgccgag    60
cagccaattc aaagcgtga caaagccgct gcaaatgatt caagarcatg yctcaatcct   120
caagctcatg atagtgttct tggaatcatt ctgggaggtg gtgctgggac tagattgtac   180
cccttgacaa gaagcgtgc caagcctgca gtgccattgg gtgccaacta tagactgatt   240
gatattcctg tcagcaattg tctcaacagc aacatatcca agatctatgt gctaacgcaa   300
tttaactctg cttccctcaa ccgtcacctc tcaagagcct acgggagcaa cattggaggg   360
tacaagaatg aagggtttgt tgaagtctta gctgcacagc agagcccaga taatccaaac   420
tggtttcagg gtactgcaga tgctgtaagg cagtacttgt ggttgtttga ggagcataat   480
gtgatggaat ttctaattct tgctggcgat cacctgtacc ggatggacta tgaaaagttc   540
attcaggcac acagagaaac aaatgctgat attaccgttg ctgccctacc gatggatgag   600
aaacgtgcaa ctgcatttgg cctcatgaaa attgatgaag aagggaggat cattgagttt   660
gctgagaaac cgaaaggaga gcagttgaaa gcaatgatgg ttgacaccac catacttggc   720
cttgatgacg tgagggcaaa ggaaatgcct tatattgcta gcatgggtat ctatgttttc   780
agcaaagatg taatgcttca gctcctccgt gaacaatttc ctgaagccaa tgactttgga   840
agtgaggtta ttccaggtgc aaccagcatt ggaaagaggg ttcaggctta tctgtatgat   900
ggttactggg aagatatcgg taccattgcg gcattttata atgcaaactt gggaataacc   960
aagaagccaa taccagattt cagcttctat gaccgttttg ctccaattta tacacaacct  1020
cgacacctgc caccttcaaa ggttcttgat gctgatgtga cagacagtgt tattggtgaa  1080
ggatgtgtta ttaaaaactg caagataaac cattctgtag ttggactccg atcttgcata  1140
tctgaaggtg ctatcataga ggacagttta ctaatgggtg cggactacta tgagacagaa  1200
gctgataaaa aactccttgc cgaaaaaggt ggcattccta ttggtattgg gaaaaattca  1260
tgcatcagga gagcaatcat tgacaagaat gctcgaattg gagacaatgt taagatactc  1320
aatgctgaca atgttcaaga agctgcaatg gagacagacg ggtacttcat caaaggtgga  1380
attgtcacag tgatcaagga tgctttactc cctagtggaa cagttata                1428
```

<210> SEQ ID NO 10
<211> LENGTH: 476
<212> TYPE: PRT
<213> ORGANISM: zea mays

<400> SEQUENCE: 10

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Ala Asn
                20                  25                  30

Asp Ser Glu Thr Cys Leu Asn Pro Gln Ala His Asp Ser Val Leu Gly
            35                  40                  45

Ile Ile Leu Gly Gly Gly Ala Gly Thr Arg Leu Tyr Pro Leu Thr Lys
        50                  55                  60

Lys Arg Ala Lys Pro Ala Val Pro Leu Gly Ala Asn Tyr Arg Leu Ile

```
              65                  70                  75                  80
Asp Ile Pro Val Ser Asn Cys Leu Asn Ser Asn Ile Ser Lys Ile Tyr
                        85                  90                  95
Val Leu Thr Gln Phe Asn Ser Ala Ser Leu Asn Arg His Leu Ser Arg
                    100                 105                 110
Ala Tyr Gly Ser Asn Ile Gly Gly Tyr Lys Asn Glu Gly Phe Val Glu
                115                 120                 125
Val Leu Ala Ala Gln Gln Ser Pro Asp Asn Pro Asn Trp Phe Gln Gly
            130                 135                 140
Thr Ala Asp Ala Val Arg Gln Tyr Leu Trp Leu Phe Glu Glu His Asn
145                 150                 155                 160
Val Met Glu Phe Leu Ile Leu Ala Gly Asp His Leu Tyr Arg Met Asp
                    165                 170                 175
Tyr Glu Lys Phe Ile Gln Ala His Arg Glu Thr Asn Ala Asp Ile Thr
                180                 185                 190
Val Ala Ala Leu Pro Met Asp Glu Lys Arg Ala Thr Ala Phe Gly Leu
            195                 200                 205
Met Lys Ile Asp Glu Glu Gly Arg Ile Ile Glu Phe Ala Glu Lys Pro
        210                 215                 220
Lys Gly Glu Gln Leu Lys Ala Met Met Val Asp Thr Thr Ile Leu Gly
225                 230                 235                 240
Leu Asp Asp Val Arg Ala Lys Glu Met Pro Tyr Ile Ala Ser Met Gly
                    245                 250                 255
Ile Tyr Val Phe Ser Lys Asp Val Met Leu Gln Leu Leu Arg Glu Gln
                260                 265                 270
Phe Pro Glu Ala Asn Asp Phe Gly Ser Glu Val Ile Pro Gly Ala Thr
            275                 280                 285
Ser Ile Gly Lys Arg Val Gln Ala Tyr Leu Tyr Asp Gly Tyr Trp Glu
        290                 295                 300
Asp Ile Gly Thr Ile Ala Ala Phe Tyr Asn Ala Asn Leu Gly Ile Thr
305                 310                 315                 320
Lys Lys Pro Ile Pro Asp Phe Ser Phe Tyr Asp Arg Phe Ala Pro Ile
                    325                 330                 335
Tyr Thr Gln Pro Arg His Leu Pro Pro Ser Lys Val Leu Asp Ala Asp
                340                 345                 350
Val Thr Asp Ser Val Ile Gly Glu Gly Cys Val Ile Lys Asn Cys Lys
            355                 360                 365
Ile Asn His Ser Val Val Gly Leu Arg Ser Cys Ile Ser Glu Gly Ala
        370                 375                 380
Ile Ile Glu Asp Ser Leu Leu Met Gly Ala Asp Tyr Tyr Glu Thr Glu
385                 390                 395                 400
Ala Asp Lys Lys Leu Leu Ala Glu Lys Gly Ile Pro Ile Gly Ile
                405                 410                 415
Gly Lys Asn Ser Cys Ile Arg Arg Ala Ile Ile Asp Lys Asn Ala Arg
                420                 425                 430
Ile Gly Asp Asn Val Lys Ile Leu Asn Ala Asp Asn Val Gln Glu Ala
            435                 440                 445
Ala Met Glu Thr Asp Gly Tyr Phe Ile Lys Gly Gly Ile Val Thr Val
        450                 455                 460
Ile Lys Asp Ala Leu Leu Pro Ser Gly Thr Val Ile
465                 470                 475

<210> SEQ ID NO 11
<211> LENGTH: 1582
```

```
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1578)
<223> OTHER INFORMATION: k = g or t.

<400> SEQUENCE: 11 ggaggagat atg cag ttt gca ctt gca ttg gac acg aac tca ggt cct cac      51
          Met Gln Phe Ala Leu Ala Leu Asp Thr Asn Ser Gly Pro His
          1               5                   10 cag ata aga tct tgt gag ggt gat ggg att gac agg ttg gaa aaa tta        99
Gln Ile Arg Ser Cys Glu Gly Asp Gly Ile Asp Arg Leu Glu Lys Leu
15                  20                  25                  30 agt att ggg ggc aga aag cag gag aaa gct ttg aga aat agg tgc ttt       147
Ser Ile Gly Gly Arg Lys Gln Glu Lys Ala Leu Arg Asn Arg Cys Phe
                35                  40                  45 ggt ggt aga gtt gct gca act aca caa tgt att ctt acc tca gat gct       195
Gly Gly Arg Val Ala Ala Thr Thr Gln Cys Ile Leu Thr Ser Asp Ala
            50                  55                  60 tgt cct gaa act ctt cat tct caa aca cag tcc tct agg aaa aat tat       243
Cys Pro Glu Thr Leu His Ser Gln Thr Gln Ser Ser Arg Lys Asn Tyr
65                  70                  75 gct gat gca aac cgt gta tct gck atc att ttg ggc gga ggc act gga       291
Ala Asp Ala Asn Arg Val Ser Ala Ile Ile Leu Gly Gly Gly Thr Gly
            80                  85                  90 tct cag ctc ttt cct ctg aca agc aca aga gct acg cct gct gta cct       339
Ser Gln Leu Phe Pro Leu Thr Ser Thr Arg Ala Thr Pro Ala Val Pro
95                  100                 105                 110 gtt gga gga tgt tac agg ctt att gat atc cct atg agt aac tgc ttc       387
Val Gly Gly Cys Tyr Arg Leu Ile Asp Ile Pro Met Ser Asn Cys Phe
                115                 120                 125 aac agt ggt ata aat aag ata ttt gtg atg agt cag ttc aat tct act       435
Asn Ser Gly Ile Asn Lys Ile Phe Val Met Ser Gln Phe Asn Ser Thr
            130                 135                 140 tcg ctt aac cgc cat att cat cgt aca tac ctt gaa ggc ggg atc aac       483
Ser Leu Asn Arg His Ile His Arg Thr Tyr Leu Glu Gly Gly Ile Asn
145                 150                 155 ttt gct gat gga tct gta cag gta tta gcg gct aca caa atg cct gaa       531
Phe Ala Asp Gly Ser Val Gln Val Leu Ala Ala Thr Gln Met Pro Glu
            160                 165                 170 gag cca gct gga tgg ttc cag ggt aca gca gac tct atc aga aaa ttt       579
Glu Pro Ala Gly Trp Phe Gln Gly Thr Ala Asp Ser Ile Arg Lys Phe
175                 180                 185                 190 atc tgg gta ctc gag gat tat tac agt cac aaa tcc att gac aac att       627
Ile Trp Val Leu Glu Asp Tyr Tyr Ser His Lys Ser Ile Asp Asn Ile
                195                 200                 205 gta atc ttg agt ggc gat cag ctt tat cgg atg aat tac atg gaa ctt       675
Val Ile Leu Ser Gly Asp Gln Leu Tyr Arg Met Asn Tyr Met Glu Leu
            210                 215                 220 gtg cag aaa cat gtc gag gac gat gct gat atc act ata tca tgt gct       723
Val Gln Lys His Val Glu Asp Asp Ala Asp Ile Thr Ile Ser Cys Ala
225                 230                 235
```

```
cct gtt gat gag agc cga gct tct aaa aat ggg cta gtg aag att gat      771
Pro Val Asp Glu Ser Arg Ala Ser Lys Asn Gly Leu Val Lys Ile Asp
    240                 245                 250 cat act gga cgt gta ctt caa ttc ttt gaa aaa cca aag ggt gct gat      819
His Thr Gly Arg Val Leu Gln Phe Phe Glu Lys Pro Lys Gly Ala Asp
255                 260                 265                 270 ttg aat tct atg aga gtt gag acc aac ttc ctg agc tat gct ata gat      867
Leu Asn Ser Met Arg Val Glu Thr Asn Phe Leu Ser Tyr Ala Ile Asp
                275                 280                 285 gat gca cag aaa tat cca tac ctt gca tca atg ggc att tat gtc ttc      915
Asp Ala Gln Lys Tyr Pro Tyr Leu Ala Ser Met Gly Ile Tyr Val Phe
        290                 295                 300 aag aaa gat gca ctt tta gac ctt ctc aag tca aaa tat act caa tta      963
Lys Lys Asp Ala Leu Leu Asp Leu Leu Lys Ser Lys Tyr Thr Gln Leu
            305                 310                 315 cat gac ttt gga tct gaa atc ctc cca aga gct gta cta gat cat agt     1011
His Asp Phe Gly Ser Glu Ile Leu Pro Arg Ala Val Leu Asp His Ser
320                 325                 330 gtg cag gca tgc att ttt acg ggc tat tgg gag gat gtt gga aca atc     1059
Val Gln Ala Cys Ile Phe Thr Gly Tyr Trp Glu Asp Val Gly Thr Ile
335                 340                 345                 350 aaa tca ttc ttt gat gca aac ttg gcc ctc act gag cag cct tcc aag     1107
Lys Ser Phe Phe Asp Ala Asn Leu Ala Leu Thr Glu Gln Pro Ser Lys
                355                 360                 365 ttt gat ttt tac gat cca aaa aca cct ttc ttc act gca ccc cga tgc     1155
Phe Asp Phe Tyr Asp Pro Lys Thr Pro Phe Phe Thr Ala Pro Arg Cys
        370                 375                 380 ttg cct ccg acg caa ttg gac aag tgc aag atg aaa tat gca ttt atc     1203
Leu Pro Pro Thr Gln Leu Asp Lys Cys Lys Met Lys Tyr Ala Phe Ile
            385                 390                 395 tca gat ggt tgc tta ctg aga gaa tgc aac atc gag cat tct gtg att     1251
Ser Asp Gly Cys Leu Leu Arg Glu Cys Asn Ile Glu His Ser Val Ile
400                 405                 410 gga gtc tgc tca cgt gtc agc tct gga tgt gaa ctc aag gac tcc gtg     1299
Gly Val Cys Ser Arg Val Ser Ser Gly Cys Glu Leu Lys Asp Ser Val
415                 420                 425                 430 atg atg gga gcg gac atc tat gaa act gaa gaa gaa gct tca aag cta     1347
Met Met Gly Ala Asp Ile Tyr Glu Thr Glu Glu Glu Ala Ser Lys Leu
                435                 440                 445 ctg tta gct ggg aag gtc ccr gtt gga ata gga agg aac aca aag ata     1395
Leu Leu Ala Gly Lys Val Pro Val Gly Ile Gly Arg Asn Thr Lys Ile
        450                 455                 460 agg aac tgt atc att gac atg aat gct agg att ggg aag aac gtg gtg     1443
Arg Asn Cys Ile Ile Asp Met Asn Ala Arg Ile Gly Lys Asn Val Val
            465                 470                 475 atc aca aac agt aag ggc atc caa gag gct gat cac ccg gaa gaa ggg     1491
Ile Thr Asn Ser Lys Gly Ile Gln Glu Ala Asp His Pro Glu Glu Gly
480                 485                 490 tac tcg tac tac ata agg tct gga atc gtg gtg atc ctg aag aat gca     1539
Tyr Ser Tyr Tyr Ile Arg Ser Gly Ile Val Val Ile Leu Lys Asn Ala
495                 500                 505                 510 acc atc aac gat ggg tct gtc ata tagatcggct gcgtktgcg                1582
Thr Ile Asn Asp Gly Ser Val Ile
                515

<210> SEQ ID NO 12
<211> LENGTH: 518
<212> TYPE: PRT
<213> ORGANISM: Zea mays

<400> SEQUENCE: 12
```

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
            35                  40                  45

Arg Val Ala Ala Thr Thr Gln Cys Ile Leu Thr Ser Asp Ala Cys Pro
50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
            115                 120                 125

Gly Ile Asn Lys Ile Phe Val Met Ser Gln Phe Asn Ser Thr Ser Leu
130                 135                 140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
            195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
            275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
            355                 360                 365

Phe Tyr Asp Pro Lys Thr Pro Phe Phe Thr Ala Pro Arg Cys Leu Pro
370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
```

-continued

```
                   420                 425                 430
Gly Ala Asp Ile Tyr Glu Thr Glu Glu Ala Ser Lys Leu Leu Leu
            435                 440                 445

Ala Gly Lys Val Pro Val Gly Ile Gly Arg Asn Thr Lys Ile Arg Asn
        450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Ser
                485                 490                 495

Tyr Tyr Ile Arg Ser Gly Ile Val Val Ile Leu Lys Asn Ala Thr Ile
            500                 505                 510

Asn Asp Gly Ser Val Ile
        515

<210> SEQ ID NO 13
<211> LENGTH: 1582
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1578)
<223> OTHER INFORMATION: k = g or t.

<400> SEQUENCE: 13 ggaggagat atg cag ttt gca ctt gca ttg gac acg aac tca ggt cct cac     51
          Met Gln Phe Ala Leu Ala Leu Asp Thr Asn Ser Gly Pro His
          1               5                   10 cag ata aga tct tgt gag ggt gat ggg att gac agg ttg gaa aaa tta      99
Gln Ile Arg Ser Cys Glu Gly Asp Gly Ile Asp Arg Leu Glu Lys Leu
15              20                  25                  30 agt att ggg ggc aga aag cag gag aaa gct ttg aga aat agg tgc ttt     147
Ser Ile Gly Gly Arg Lys Gln Glu Lys Ala Leu Arg Asn Arg Cys Phe
                35                  40                  45 ggt ggt aga gtt gct gca act aca caa tgt att ctt acc tca gat gct     195
Gly Gly Arg Val Ala Ala Thr Thr Gln Cys Ile Leu Thr Ser Asp Ala
            50                  55                  60 tgt cct gaa act ctt cat tct caa aca cag tcc tct agg aaa aat tat     243
Cys Pro Glu Thr Leu His Ser Gln Thr Gln Ser Ser Arg Lys Asn Tyr
65              70                  75 gct gat gca aac cgt gta tct gck atc att ttg ggc gga ggc act gga     291
Ala Asp Ala Asn Arg Val Ser Ala Ile Ile Leu Gly Gly Gly Thr Gly
        80                  85                  90 tct cag ctc ttt cct ctg aca agc aca aga gct acg cct gct gta cct     339
Ser Gln Leu Phe Pro Leu Thr Ser Thr Arg Ala Thr Pro Ala Val Pro
95                  100                 105                 110 gtt gga gga tgt tac agg ctt att gat atc cct atg agt aac tgc ttc     387
Val Gly Gly Cys Tyr Arg Leu Ile Asp Ile Pro Met Ser Asn Cys Phe
                115                 120                 125
```

| | | | | | | | | | | | | | | | | |
|---|---|---|---|---|---|---|---|---|---|---|---|---|---|---|---|---|
| aac | agt | ggt | ata | aat | aag | ata | ttt | gtg | atg | agt | cag | ttc | aat | tct | act | 435 |
| Asn | Ser | Gly | Ile | Asn | Lys | Ile | Phe | Val | Met | Ser | Gln | Phe | Asn | Ser | Thr | |
| | | | 130 | | | | 135 | | | | 140 | | | | | |
| tcg | ctt | aac | cgc | cat | att | cat | cgt | aca | tac | ctt | gaa | ggc | ggg | atc | aac | 483 |
| Ser | Leu | Asn | Arg | His | Ile | His | Arg | Thr | Tyr | Leu | Glu | Gly | Gly | Ile | Asn | |
| | | 145 | | | | | 150 | | | | | 155 | | | | |
| ttt | gct | gat | gga | tct | gta | cag | gta | tta | gcg | gct | aca | caa | atg | cct | gaa | 531 |
| Phe | Ala | Asp | Gly | Ser | Val | Gln | Val | Leu | Ala | Ala | Thr | Gln | Met | Pro | Glu | |
| | 160 | | | | | 165 | | | | | 170 | | | | | |
| gag | cca | gct | gga | tgg | ttc | cag | ggt | aca | gca | gac | tct | atc | aga | aaa | ttt | 579 |
| Glu | Pro | Ala | Gly | Trp | Phe | Gln | Gly | Thr | Ala | Asp | Ser | Ile | Arg | Lys | Phe | |
| 175 | | | | | 180 | | | | | 185 | | | | | 190 | |
| atc | tgg | gta | ctc | gag | gat | tat | tac | agt | cac | aaa | tcc | att | gac | aac | att | 627 |
| Ile | Trp | Val | Leu | Glu | Asp | Tyr | Tyr | Ser | His | Lys | Ser | Ile | Asp | Asn | Ile | |
| | | | | 195 | | | | | 200 | | | | | 205 | | |
| gta | atc | ttg | agt | ggc | gat | cag | ctt | tat | cgg | atg | aat | tac | atg | gaa | ctt | 675 |
| Val | Ile | Leu | Ser | Gly | Asp | Gln | Leu | Tyr | Arg | Met | Asn | Tyr | Met | Glu | Leu | |
| | | | 210 | | | | | 215 | | | | | 220 | | | |
| gtg | cag | aaa | cat | gtc | gag | gac | gat | gct | gat | atc | act | ata | tca | tgt | gct | 723 |
| Val | Gln | Lys | His | Val | Glu | Asp | Asp | Ala | Asp | Ile | Thr | Ile | Ser | Cys | Ala | |
| | | 225 | | | | | 230 | | | | | 235 | | | | |
| cct | gtt | gat | gag | agc | cga | gct | tct | aaa | aat | ggg | cta | gtg | aag | att | gat | 771 |
| Pro | Val | Asp | Glu | Ser | Arg | Ala | Ser | Lys | Asn | Gly | Leu | Val | Lys | Ile | Asp | |
| | 240 | | | | | 245 | | | | | 250 | | | | | |
| cat | act | gga | cgt | gta | ctt | caa | ttc | ttt | gaa | aaa | cca | aag | ggt | gct | gat | 819 |
| His | Thr | Gly | Arg | Val | Leu | Gln | Phe | Phe | Glu | Lys | Pro | Lys | Gly | Ala | Asp | |
| 255 | | | | | 260 | | | | | 265 | | | | | 270 | |
| ttg | aat | tct | atg | aga | gtt | gag | acc | aac | ttc | ctg | agc | tat | gct | ata | gat | 867 |
| Leu | Asn | Ser | Met | Arg | Val | Glu | Thr | Asn | Phe | Leu | Ser | Tyr | Ala | Ile | Asp | |
| | | | | 275 | | | | | 280 | | | | | 285 | | |
| gat | gca | cag | aaa | tat | cca | tac | ctt | gca | tca | atg | ggc | att | tat | gtc | ttc | 915 |
| Asp | Ala | Gln | Lys | Tyr | Pro | Tyr | Leu | Ala | Ser | Met | Gly | Ile | Tyr | Val | Phe | |
| | | | 290 | | | | | 295 | | | | | 300 | | | |
| aag | aaa | gat | gca | ctt | tta | gac | ctt | ctc | aag | tca | aaa | tat | act | caa | tta | 963 |
| Lys | Lys | Asp | Ala | Leu | Leu | Asp | Leu | Leu | Lys | Ser | Lys | Tyr | Thr | Gln | Leu | |
| | | 305 | | | | | 310 | | | | | 315 | | | | |
| cat | gac | ttt | gga | tct | gaa | atc | ctc | cca | aga | gct | gta | cta | gat | tay | agt | 1011 |
| His | Asp | Phe | Gly | Ser | Glu | Ile | Leu | Pro | Arg | Ala | Val | Leu | Asp | Tyr | Ser | |
| | 320 | | | | | 325 | | | | | 330 | | | | | |
| gtg | cag | gca | tgc | att | ttt | acg | ggc | tat | tgg | gag | gat | gtt | gga | aca | atc | 1059 |
| Val | Gln | Ala | Cys | Ile | Phe | Thr | Gly | Tyr | Trp | Glu | Asp | Val | Gly | Thr | Ile | |
| 335 | | | | | 340 | | | | | 345 | | | | | 350 | |
| aaa | tca | ttc | ttt | gat | gca | aac | ttg | gcc | ctc | act | gag | cag | cct | tcc | aag | 1107 |
| Lys | Ser | Phe | Phe | Asp | Ala | Asn | Leu | Ala | Leu | Thr | Glu | Gln | Pro | Ser | Lys | |
| | | | | 355 | | | | | 360 | | | | | 365 | | |
| ttt | gat | ttt | tac | gat | cca | aaa | aca | cct | ttc | ttc | act | gca | ccc | cga | tgc | 1155 |
| Phe | Asp | Phe | Tyr | Asp | Pro | Lys | Thr | Pro | Phe | Phe | Thr | Ala | Pro | Arg | Cys | |
| | | | 370 | | | | | 375 | | | | | 380 | | | |
| ttg | cct | ccg | acg | caa | ttg | gac | aag | tgc | aag | atg | aaa | tat | gca | ttt | atc | 1203 |
| Leu | Pro | Pro | Thr | Gln | Leu | Asp | Lys | Cys | Lys | Met | Lys | Tyr | Ala | Phe | Ile | |
| | | 385 | | | | | 390 | | | | | 395 | | | | |
| tca | gat | ggt | tgc | tta | ctg | aga | gaa | tgc | aac | atc | gag | cat | tct | gtg | att | 1251 |
| Ser | Asp | Gly | Cys | Leu | Leu | Arg | Glu | Cys | Asn | Ile | Glu | His | Ser | Val | Ile | |
| | 400 | | | | | 405 | | | | | 410 | | | | | |
| gga | gtc | tgc | tca | cgt | gtc | agc | tct | gga | tgt | gaa | ctc | aag | gac | tcc | gtg | 1299 |
| Gly | Val | Cys | Ser | Arg | Val | Ser | Ser | Gly | Cys | Glu | Leu | Lys | Asp | Ser | Val | |
| 415 | | | | | 420 | | | | | 425 | | | | | 430 | |
| atg | atg | gga | gcg | gac | atc | tat | gaa | act | gaa | gaa | gaa | gct | tca | aag | cta | 1347 |
| Met | Met | Gly | Ala | Asp | Ile | Tyr | Glu | Thr | Glu | Glu | Glu | Ala | Ser | Lys | Leu | |
| | | | | 435 | | | | | 440 | | | | | 445 | | |

```
ctg tta gct ggg aag gtc ccr gtt gga ata gga agg aac aca aag ata    1395
Leu Leu Ala Gly Lys Val Pro Val Gly Ile Gly Arg Asn Thr Lys Ile
            450                 455                 460 agg aac tgt atc att gac atg aat gct agg att ggg aag aac gtg gtg    1443
Arg Asn Cys Ile Ile Asp Met Asn Ala Arg Ile Gly Lys Asn Val Val
        465                 470                 475 atc aca aac agt aag ggc atc caa gag gct gat cac ccg gaa gaa ggg    1491
Ile Thr Asn Ser Lys Gly Ile Gln Glu Ala Asp His Pro Glu Glu Gly
    480                 485                 490 tac tcg tac tac ata agg tct gga atc gtg gtg atc ctg aag aat gca    1539
Tyr Ser Tyr Tyr Ile Arg Ser Gly Ile Val Val Ile Leu Lys Asn Ala
495                 500                 505                 510 acc atc aac gat ggg tct gtc ata tagatcggct gcgtktgcg               1582
Thr Ile Asn Asp Gly Ser Val Ile
                515

<210> SEQ ID NO 14
<211> LENGTH: 518
<212> TYPE: PRT
<213> ORGANISM: Zea mays

<400> SEQUENCE: 14

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
            85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
            165                 170                 175

Ala Gly Trp Phe Gln Gly Thr Ala Asp Ser Ile Arg Lys Phe Ile Trp
        180                 185                 190

Val Leu Glu Asp Tyr Tyr Ser His Lys Ser Ile Asp Asn Ile Val Ile
    195                 200                 205

Leu Ser Gly Asp Gln Leu Tyr Arg Met Asn Tyr Met Glu Leu Val Gln
    210                 215                 220

Lys His Val Glu Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
            245                 250                 255

Gly Arg Val Leu Gln Phe Phe Glu Lys Pro Lys Gly Ala Asp Leu Asn
        260                 265                 270
```

```
Ser Met Arg Val Glu Thr Asn Phe Leu Ser Tyr Ala Ile Asp Asp Ala
    275                 280                 285

Gln Lys Tyr Pro Tyr Leu Ala Ser Met Gly Ile Tyr Val Phe Lys Lys
290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Tyr Ser Val Gln
                325                 330                 335

Ala Cys Ile Phe Thr Gly Tyr Trp Glu Asp Val Gly Thr Ile Lys Ser
                340                 345                 350

Phe Phe Asp Ala Asn Leu Ala Leu Thr Glu Gln Pro Ser Lys Phe Asp
            355                 360                 365

Phe Tyr Asp Pro Lys Thr Pro Phe Phe Thr Ala Pro Arg Cys Leu Pro
370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
            420                 425                 430

Gly Ala Asp Ile Tyr Glu Thr Glu Glu Glu Ala Ser Lys Leu Leu Leu
435                 440                 445

Ala Gly Lys Val Pro Val Gly Ile Gly Arg Asn Thr Lys Ile Arg Asn
450                 455                 460

Cys Ile Ile Asp Met Asn Ala Arg Ile Gly Lys Asn Val Ile Ile Thr
465                 470                 475                 480

Asn Ser Lys Gly Ile Gln Glu Ala Asp His Pro Glu Glu Gly Tyr Ser
                485                 490                 495

Tyr Tyr Ile Arg Ser Gly Ile Val Val Ile Leu Lys Asn Ala Thr Ile
                500                 505                 510

Asn Asp Gly Ser Val Ile
                515

<210> SEQ ID NO 15
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 15 ggaggagat atg cag ttt gca ctt gca ttg gac acg aac tca ggt cct cac    51
          Met Gln Phe Ala Leu Ala Leu Asp Thr Asn Ser Gly Pro His
            1               5                  10
```

| | |
|---|---|
| cag ata aga tct tgt gag ggt gat ggg att gac agg ttg gaa aaa tta<br>Gln Ile Arg Ser Cys Glu Gly Asp Gly Ile Asp Arg Leu Glu Lys Leu<br>15                              20                         25                         30 | 99 |
| agt att ggg ggc aga aag cag gag aaa gct ttg aga aat agg tgc ttt<br>Ser Ile Gly Gly Arg Lys Gln Glu Lys Ala Leu Arg Asn Arg Cys Phe<br>                     35                       40                       45 | 147 |
| ggt gga aga gtt gct gca act aca caa tgt att ctt acc tca gat gct<br>Gly Gly Arg Val Ala Ala Thr Thr Gln Cys Ile Leu Thr Ser Asp Ala<br>        50                        55                       60 | 195 |
| tgt cct gaa act ctt cat tct caa aca cag tcc tct agg aaa aat tat<br>Cys Pro Glu Thr Leu His Ser Gln Thr Gln Ser Ser Arg Lys Asn Tyr<br>              65                     70                     75 | 243 |
| gct gat gca aac cgt gta tct gck atc att ttg ggc gga ggc act gga<br>Ala Asp Ala Asn Arg Val Ser Ala Ile Ile Leu Gly Gly Gly Thr Gly<br>80                            85                         90 | 291 |
| tct cag ctc ttt cct ctg aca agc aca aga gct acg cct gct gta cct<br>Ser Gln Leu Phe Pro Leu Thr Ser Thr Arg Ala Thr Pro Ala Val Pro<br>95                           100                    105                   110 | 339 |
| gtt gga gga tgt tac agg ctt att gat atc cct atg agt aac tgc ttc<br>Val Gly Gly Cys Tyr Arg Leu Ile Asp Ile Pro Met Ser Asn Cys Phe<br>                 115                    120                   125 | 387 |
| aac agt ggt ata aat aag ata ttt gtg atg agt cag ttc aat tct act<br>Asn Ser Gly Ile Asn Lys Ile Phe Val Met Ser Gln Phe Asn Ser Thr<br>        130                    135                   140 | 435 |
| tcg ctt aac cgc cat att cat cgt aca tac ctt gaa ggc ggg atc aac<br>Ser Leu Asn Arg His Ile His Arg Thr Tyr Leu Glu Gly Gly Ile Asn<br>             145                    150                   155 | 483 |
| ttt gct gat gga tct gta cag gta tta gcg gct aca caa atg cct gaa<br>Phe Ala Asp Gly Ser Val Gln Val Leu Ala Ala Thr Gln Met Pro Glu<br>160                         165                   170 | 531 |
| gag cca gct gga tgg ttc cag ggt aca gca gac tct atc aga aaa ttt<br>Glu Pro Ala Gly Trp Phe Gln Gly Thr Ala Asp Ser Ile Arg Lys Phe<br>175                       180                   185               190 | 579 |
| atc tgg gta ctc gag gat tat tac agt cac aaa tcc att gac aac att<br>Ile Trp Val Leu Glu Asp Tyr Tyr Ser His Lys Ser Ile Asp Asn Ile<br>                 195                    200                   205 | 627 |
| gta atc ttg agt ggc gat cag ctt tat cgg atg aat tac atg gaa ctt<br>Val Ile Leu Ser Gly Asp Gln Leu Tyr Arg Met Asn Tyr Met Glu Leu<br>        210                    215                   220 | 675 |
| gtg cag aaa cat gtc gag gac gat gct gat atc act ata tca tgt gct<br>Val Gln Lys His Val Glu Asp Asp Ala Asp Ile Thr Ile Ser Cys Ala<br>             225                    230                   235 | 723 |
| cct gtt gat gag agc cga gct tct aaa aat ggg cta gtg aag att gat<br>Pro Val Asp Glu Ser Arg Ala Ser Lys Asn Gly Leu Val Lys Ile Asp<br>240                         245                   250 | 771 |
| cat act gga cgt gta ctt caa ttc ttt gaa aaa cca aag ggt gct gat<br>His Thr Gly Arg Val Leu Gln Phe Phe Glu Lys Pro Lys Gly Ala Asp<br>255                       260                   265               270 | 819 |
| ttg aat tct atg aga gtt gag acc aac ttc ctg agc tat gct ata gat<br>Leu Asn Ser Met Arg Val Glu Thr Asn Phe Leu Ser Tyr Ala Ile Asp<br>                 275                    280                   285 | 867 |
| gat gca cag aaa tat cca tac ctt gca tca atg ggc att tat gtc ttc<br>Asp Ala Gln Lys Tyr Pro Tyr Leu Ala Ser Met Gly Ile Tyr Val Phe<br>        290                    295                   300 | 915 |
| aag aaa gat gca ctt tta gac ctt ctc aag tca aaa tat act caa tta<br>Lys Lys Asp Ala Leu Leu Asp Leu Leu Lys Ser Lys Tyr Thr Gln Leu<br>             305                    310                   315 | 963 |
| cat gac ttt gga tct gaa atc ctc cca aga gct gta cta gat tay agt<br>His Asp Phe Gly Ser Glu Ile Leu Pro Arg Ala Val Leu Asp Tyr Ser<br>320                         325                   330 | 1011 |

| | | | | | | | | | | | |
|---|---|---|---|---|---|---|---|---|---|---|---|
| gtg | cag | gca | tgc | att | ttt | acg | ggc | tat | tgg | gag | gat | gtt | gga | aca | atc | 1059 |
| Val | Gln | Ala | Cys | Ile | Phe | Thr | Gly | Tyr | Trp | Glu | Asp | Val | Gly | Thr | Ile | |
| 335 | | | | 340 | | | | | 345 | | | | | 350 | | |

```
gtg cag gca tgc att ttt acg ggc tat tgg gag gat gtt gga aca atc    1059
Val Gln Ala Cys Ile Phe Thr Gly Tyr Trp Glu Asp Val Gly Thr Ile
335             340             345             350 aaa tca ttc ttt gat gca aac ttg gcc ctc act gag cag cct tcc aag    1107
Lys Ser Phe Phe Asp Ala Asn Leu Ala Leu Thr Glu Gln Pro Ser Lys
        355             360             365 ttt gat ttt tac gat cca aaa aca cct ttc ttc act gca ccc cga tgc    1155
Phe Asp Phe Tyr Asp Pro Lys Thr Pro Phe Phe Thr Ala Pro Arg Cys
370             375             380 ttg cct ccg acg caa ttg gac aag tgc aag atg aaa tat gca ttt atc    1203
Leu Pro Pro Thr Gln Leu Asp Lys Cys Lys Met Lys Tyr Ala Phe Ile
        385             390             395 tca gat ggt tgc tta ctg aga gaa tgc aac atc gag cat tct gtg att    1251
Ser Asp Gly Cys Leu Leu Arg Glu Cys Asn Ile Glu His Ser Val Ile
400             405             410 gga gtc tgc tca cgt gtc agc tct gga tgt gaa ctc aag gac tcc gtg    1299
Gly Val Cys Ser Arg Val Ser Ser Gly Cys Glu Leu Lys Asp Ser Val
415             420             425             430 atg atg gga gcg gac atc tat gaa act gaa gaa gaa gct tca aag cta    1347
Met Met Gly Ala Asp Ile Tyr Glu Thr Glu Glu Glu Ala Ser Lys Leu
            435             440             445 ctg tta gct ggg aag gtc ccr gtt gga ata gga agg aac aca aag ata    1395
Leu Leu Ala Gly Lys Val Pro Val Gly Ile Gly Arg Asn Thr Lys Ile
        450             455             460 agg aac tgt atc att gac atg aat gct agg att ggg aag aac gtg gtg    1443
Arg Asn Cys Ile Ile Asp Met Asn Ala Arg Ile Gly Lys Asn Val Val
465             470             475 atc aca aac agt aag ggc atc caa gag gct gat cac ccg gaa gaa ggg    1491
Ile Thr Asn Ser Lys Gly Ile Gln Glu Ala Asp His Pro Glu Glu Gly
480             485             490 tac tac ata agg tct gga atc gtg gtg atc ctg aag aat gca acc atc    1539
Tyr Tyr Ile Arg Ser Gly Ile Val Val Ile Leu Lys Asn Ala Thr Ile
495             500             505             510 aac gat ggg tct gtc ata tagatcggct gcgtktgcg                        1576
Asn Asp Gly Ser Val Ile
            515
```

<210> SEQ ID NO 16
<211> LENGTH: 516
<212> TYPE: PRT
<213> ORGANISM: Zea mays

<400> SEQUENCE: 16

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125
```

Gly Ile Asn Lys Ile Phe Val Met Ser Gln Phe Asn Ser Thr Ser Leu
            130                 135                 140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
                180                 185                 190

Val Leu Glu Asp Tyr Tyr Ser His Lys Ser Ile Asp Asn Ile Val Ile
            195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
                260                 265                 270

Ser Met Arg Val Glu Thr Asn Phe Leu Ser Tyr Ala Ile Asp Asp Ala
            275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Tyr Ser Val Gln
                325                 330                 335

Ala Cys Ile Phe Thr Gly Tyr Trp Glu Asp Val Gly Thr Ile Lys Ser
                340                 345                 350

Phe Phe Asp Ala Asn Leu Ala Leu Thr Glu Gln Pro Ser Lys Phe Asp
            355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
                420                 425                 430

Gly Ala Asp Ile Tyr Glu Thr Glu Glu Ala Ser Lys Leu Leu Leu
            435                 440                 445

Ala Gly Lys Val Pro Val Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
                500                 505                 510

Gly Ser Val Ile
            515

<210> SEQ ID NO 17
<211> LENGTH: 1576
<212> TYPE: DNA

```
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (540)
<223> OTHER INFORMATION: n = a or g or c or t/u, unknown, or other.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 17
```

| | | | | | | | | | | | | | | |
|---|---|---|---|---|---|---|---|---|---|---|---|---|---|---|
| ggaggagat | atg | cag | ttt | gca | ctt | gca | ttg | gac | acg | aac | tca | ggt | cct | cac | 51 |
| | Met | Gln | Phe | Ala | Leu | Ala | Leu | Asp | Thr | Asn | Ser | Gly | Pro | His | |
| | 1 | | | 5 | | | | | 10 | | | | | | |

| cag | ata | aga | tct | tgt | gag | ggt | gat | ggg | att | gac | agg | ttg | gaa | aaa | tta | 99 |
|---|---|---|---|---|---|---|---|---|---|---|---|---|---|---|---|---|
| Gln | Ile | Arg | Ser | Cys | Glu | Gly | Asp | Gly | Ile | Asp | Arg | Leu | Glu | Lys | Leu | |
| 15 | | | | | 20 | | | | | 25 | | | | | 30 | |

| agt | att | ggg | ggc | aga | aag | cag | gag | aaa | gct | ttg | aga | aat | agg | tgc | ttt | 147 |
|---|---|---|---|---|---|---|---|---|---|---|---|---|---|---|---|---|
| Ser | Ile | Gly | Gly | Arg | Lys | Gln | Glu | Lys | Ala | Leu | Arg | Asn | Arg | Cys | Phe | |
| | | | 35 | | | | | 40 | | | | | 45 | | | |

| ggt | ggt | aga | gtt | gct | gca | act | aca | caa | tgt | att | ctt | acc | tca | gat | gct | 195 |
|---|---|---|---|---|---|---|---|---|---|---|---|---|---|---|---|---|
| Gly | Gly | Arg | Val | Ala | Ala | Thr | Thr | Gln | Cys | Ile | Leu | Thr | Ser | Asp | Ala | |
| | | 50 | | | | | 55 | | | | | 60 | | | | |

| tgt | cct | gaa | act | ctt | cat | tct | caa | aca | cag | tcc | tct | agg | aaa | aat | tat | 243 |
|---|---|---|---|---|---|---|---|---|---|---|---|---|---|---|---|---|
| Cys | Pro | Glu | Thr | Leu | His | Ser | Gln | Thr | Gln | Ser | Ser | Arg | Lys | Asn | Tyr | |
| | | 65 | | | | | 70 | | | | | 75 | | | | |

| gct | gat | gca | aac | cgt | gta | tct | gck | atc | att | ttg | ggc | gga | ggc | act | gga | 291 |
|---|---|---|---|---|---|---|---|---|---|---|---|---|---|---|---|---|
| Ala | Asp | Ala | Asn | Arg | Val | Ser | Ala | Ile | Ile | Leu | Gly | Gly | Gly | Thr | Gly | |
| 80 | | | | | 85 | | | | | 90 | | | | | | |

| tct | cag | ctc | ttt | cct | ctg | aca | agc | aca | aga | gct | acg | cct | gct | gta | cct | 339 |
|---|---|---|---|---|---|---|---|---|---|---|---|---|---|---|---|---|
| Ser | Gln | Leu | Phe | Pro | Leu | Thr | Ser | Thr | Arg | Ala | Thr | Pro | Ala | Val | Pro | |
| 95 | | | | | 100 | | | | | 105 | | | | | 110 | |

| gtt | gga | gga | tgt | tac | agg | ctt | att | gat | atc | cct | atg | agt | aac | tgc | ttc | 387 |
|---|---|---|---|---|---|---|---|---|---|---|---|---|---|---|---|---|
| Val | Gly | Gly | Cys | Tyr | Arg | Leu | Ile | Asp | Ile | Pro | Met | Ser | Asn | Cys | Phe | |
| | | | | 115 | | | | | 120 | | | | | 125 | | |

| aac | agt | ggt | ata | aat | aag | ata | ttt | gtg | atg | agt | cag | ttc | aat | tct | act | 435 |
|---|---|---|---|---|---|---|---|---|---|---|---|---|---|---|---|---|
| Asn | Ser | Gly | Ile | Asn | Lys | Ile | Phe | Val | Met | Ser | Gln | Phe | Asn | Ser | Thr | |
| | | 130 | | | | | 135 | | | | | 140 | | | | |

| tcg | ctt | aac | cgc | cat | att | cat | cgt | aca | tac | ctt | gaa | ggc | ggg | atc | aac | 483 |
|---|---|---|---|---|---|---|---|---|---|---|---|---|---|---|---|---|
| Ser | Leu | Asn | Arg | His | Ile | His | Arg | Thr | Tyr | Leu | Glu | Gly | Gly | Ile | Asn | |
| | 145 | | | | | 150 | | | | | 155 | | | | | |

| ttt | gct | gat | gga | tct | gta | cag | gta | tta | gcg | gct | aca | caa | atg | cct | gaa | 531 |
|---|---|---|---|---|---|---|---|---|---|---|---|---|---|---|---|---|
| Phe | Ala | Asp | Gly | Ser | Val | Gln | Val | Leu | Ala | Ala | Thr | Gln | Met | Pro | Glu | |
| | 160 | | | | | 165 | | | | | 170 | | | | | |

| gag | cca | ccn | gga | tgg | ttc | cag | ggt | aca | gca | gac | tct | atc | aga | aaa | ttt | 579 |
|---|---|---|---|---|---|---|---|---|---|---|---|---|---|---|---|---|
| Glu | Pro | Pro | Gly | Trp | Phe | Gln | Gly | Thr | Ala | Asp | Ser | Ile | Arg | Lys | Phe | |
| 175 | | | | | 180 | | | | | 185 | | | | | 190 | |

| atc | tgg | gta | ctc | gag | gat | tat | tac | agt | cac | aaa | tcc | att | gac | aac | att | 627 |
|---|---|---|---|---|---|---|---|---|---|---|---|---|---|---|---|---|
| Ile | Trp | Val | Leu | Glu | Asp | Tyr | Tyr | Ser | His | Lys | Ser | Ile | Asp | Asn | Ile | |
| | | | 195 | | | | | 200 | | | | | 205 | | | |

```
gta atc ttg agt ggc gat cag ctt tat cgg atg aat tac atg gaa ctt      675
Val Ile Leu Ser Gly Asp Gln Leu Tyr Arg Met Asn Tyr Met Glu Leu
        210                 215                 220 gtg cag aaa cat gtc gag gac gat gct gat atc act ata tca tgt gct      723
Val Gln Lys His Val Glu Asp Asp Ala Asp Ile Thr Ile Ser Cys Ala
            225                 230                 235 cct gtt gat gag agc cga gct tct aaa aat ggg cta gtg aag att gat      771
Pro Val Asp Glu Ser Arg Ala Ser Lys Asn Gly Leu Val Lys Ile Asp
    240                 245                 250 cat act gga cgt gta ctt caa ttc ttt gaa aaa cca aag ggt gct gat      819
His Thr Gly Arg Val Leu Gln Phe Phe Glu Lys Pro Lys Gly Ala Asp
255                 260                 265                 270 ttg aat tct atg aga gtt gag acc aac ttc ctg agc tat gct ata gat      867
Leu Asn Ser Met Arg Val Glu Thr Asn Phe Leu Ser Tyr Ala Ile Asp
                275                 280                 285 gat gca cag aaa tat cca tac ctt gca tca atg ggc att tat gtc ttc      915
Asp Ala Gln Lys Tyr Pro Tyr Leu Ala Ser Met Gly Ile Tyr Val Phe
            290                 295                 300 aag aaa gat gca ctt tta gac ctt ctc aag tca aaa tat act caa tta      963
Lys Lys Asp Ala Leu Leu Asp Leu Leu Lys Ser Lys Tyr Thr Gln Leu
    305                 310                 315 cat gac ttt gga tct gaa atc ctc cca aga gct gta cta gat cay agt     1011
His Asp Phe Gly Ser Glu Ile Leu Pro Arg Ala Val Leu Asp His Ser
320                 325                 330 gtg cag gca tgc att ttt acg ggc tat tgg gag gat gtt gga aca atc     1059
Val Gln Ala Cys Ile Phe Thr Gly Tyr Trp Glu Asp Val Gly Thr Ile
335                 340                 345                 350 aaa tca ttc ttt gat gca aac ttg gcc ctc act gag cag cct tcc aag     1107
Lys Ser Phe Phe Asp Ala Asn Leu Ala Leu Thr Glu Gln Pro Ser Lys
                355                 360                 365 ttt gat ttt tac gat cca aaa aca cct ttc ttc act gca ccc cga tgc     1155
Phe Asp Phe Tyr Asp Pro Lys Thr Pro Phe Phe Thr Ala Pro Arg Cys
            370                 375                 380 ttg cct ccg acg caa ttg gac aag tgc aag atg aaa tat gca ttt atc     1203
Leu Pro Pro Thr Gln Leu Asp Lys Cys Lys Met Lys Tyr Ala Phe Ile
    385                 390                 395 tca gat ggt tgc tta ctg aga gaa tgc aac atc gag cat tct gtg att     1251
Ser Asp Gly Cys Leu Leu Arg Glu Cys Asn Ile Glu His Ser Val Ile
400                 405                 410 gga gtc tgc tca cgt gtc agc tct gga tgt gaa ctc aag gac tcc gtg     1299
Gly Val Cys Ser Arg Val Ser Ser Gly Cys Glu Leu Lys Asp Ser Val
415                 420                 425                 430 atg atg gga gcg gac atc tat gaa act gaa gaa gaa gct tca aag cta     1347
Met Met Gly Ala Asp Ile Tyr Glu Thr Glu Glu Glu Ala Ser Lys Leu
                435                 440                 445 ctg tta gct ggg aag gtc ccr gtt gga ata gga agg aac aca aag ata     1395
Leu Leu Ala Gly Lys Val Pro Val Gly Ile Gly Arg Asn Thr Lys Ile
            450                 455                 460 agg aac tgt atc att gac atg aat gct agg att ggg aag aac gtg gtg     1443
Arg Asn Cys Ile Ile Asp Met Asn Ala Arg Ile Gly Lys Asn Val Val
    465                 470                 475 atc aca aac agt aag ggc atc caa gag gct gat cac ccg gaa gaa ggg     1491
Ile Thr Asn Ser Lys Gly Ile Gln Glu Ala Asp His Pro Glu Glu Gly
480                 485                 490 tac tac ata agg tct gga atc gtg gtg atc ctg aag aat gca acc atc     1539
Tyr Tyr Ile Arg Ser Gly Ile Val Val Ile Leu Lys Asn Ala Thr Ile
495                 500                 505                 510 aac gat ggg tct gtc ata tagatcggct gcgtktgcg                        1576
Asn Asp Gly Ser Val Ile
                515
```

```
<210> SEQ ID NO 18
<211> LENGTH: 516
<212> TYPE: PRT
<213> ORGANISM: Zea mays

<400> SEQUENCE: 18
```

| | | | | | | | | | | | | | | |
|---|---|---|---|---|---|---|---|---|---|---|---|---|---|---|
| Met | Gln | Phe | Ala | Leu | Ala | Leu | Asp | Thr | Asn | Ser | Gly | Pro | His | Gln | Ile |
| 1 | | | | 5 | | | | | 10 | | | | | 15 | |

Arg Ser Cys Glu Gly Asp Gly Ile Asp Arg Leu Glu Lys Leu Ser Ile
              20                  25                  30

Gly Gly Arg Lys Gln Glu Lys Ala Leu Arg Asn Arg Cys Phe Gly Gly
          35                  40                  45

Arg Val Ala Ala Thr Thr Gln Cys Ile Leu Thr Ser Asp Ala Cys Pro
 50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
              85                  90                  95

Leu Phe Pro Leu Thr Ser Thr Arg Ala Thr Pro Ala Val Pro Val Gly
              100                 105                 110

Gly Cys Tyr Arg Leu Ile Asp Ile Pro Met Ser Asn Cys Phe Asn Ser
          115                 120                 125

Gly Ile Asn Lys Ile Phe Val Met Ser Gln Phe Asn Ser Thr Ser Leu
130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
              165                 170                 175

Pro Gly Trp Phe Gln Gly Thr Ala Asp Ser Ile Arg Lys Phe Ile Trp
          180                 185                 190

Val Leu Glu Asp Tyr Tyr Ser His Lys Ser Ile Asp Asn Ile Val Ile
          195                 200                 205

Leu Ser Gly Asp Gln Leu Tyr Arg Met Asn Tyr Met Glu Leu Val Gln
      210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
              245                 250                 255

Gly Arg Val Leu Gln Phe Phe Glu Lys Pro Lys Gly Ala Asp Leu Asn
          260                 265                 270

Ser Met Arg Val Glu Thr Asn Phe Leu Ser Tyr Ala Ile Asp Asp Ala
      275                 280                 285

Gln Lys Tyr Pro Tyr Leu Ala Ser Met Gly Ile Tyr Val Phe Lys Lys
  290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
              325                 330                 335

Ala Cys Ile Phe Thr Gly Tyr Trp Glu Asp Val Gly Thr Ile Lys Ser
          340                 345                 350

Phe Phe Asp Ala Asn Leu Ala Leu Thr Glu Gln Pro Ser Lys Phe Asp
      355                 360                 365

Phe Tyr Asp Pro Lys Thr Pro Phe Phe Thr Ala Pro Arg Cys Leu Pro
  370                 375                 380

```
Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
            405                 410                 415

Cys Ser Arg Val Ser Ser Gly Cys Glu Leu Lys Asp Ser Val Met Met
        420                 425                 430

Gly Ala Asp Ile Tyr Glu Thr Glu Glu Ala Ser Lys Leu Leu Leu
    435                 440                 445

Ala Gly Lys Val Pro Val Gly Ile Gly Arg Asn Thr Lys Ile Arg Asn
450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
            485                 490                 495

Ile Arg Ser Gly Ile Val Val Ile Leu Lys Asn Ala Thr Ile Asn Asp
        500                 505                 510

Gly Ser Val Ile
        515

<210> SEQ ID NO 19
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1209)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1371)
<223> OTHER INFORMATION: h = a or c or t/u.
<220> FEATURE:
<221> NAME/KEY: variation
<222> LOCATION: (1572)
<223> OTHER INFORMATION: k = g or t.

<400> SEQUENCE: 19 ggaggagat atg cag ttt gca ctt gca ttg gac acg aac tca ggt cct cac      51
          Met Gln Phe Ala Leu Ala Leu Asp Thr Asn Ser Gly Pro His
          1               5                   10 cag ata aga tct tgt gag ggt gat ggg att gac agg ttg gaa aaa tta       99
Gln Ile Arg Ser Cys Glu Gly Asp Gly Ile Asp Arg Leu Glu Lys Leu
15                  20                  25                  30 agt att ggg ggc aga aag cag gag aaa gct ttg aga aat agg tgc ttt      147
Ser Ile Gly Gly Arg Lys Gln Glu Lys Ala Leu Arg Asn Arg Cys Phe
                35                  40                  45 ggt ggt aga gtt gct gca act aca caa tgt att ctt acc tca gat gct      195
Gly Gly Arg Val Ala Ala Thr Thr Gln Cys Ile Leu Thr Ser Asp Ala
        50                  55                  60
```

| | | |
|---|---|---|
| tgt cct gaa act ctt cat tct caa aca cag tcc tct agg aaa aat tat<br>Cys Pro Glu Thr Leu His Ser Gln Thr Gln Ser Ser Arg Lys Asn Tyr<br>         65                     70                   75 | 243 |
| gct gat gca aac cgt gta tct gck atc att ttg ggc gga ggc act gga<br>Ala Asp Ala Asn Arg Val Ser Ala Ile Ile Leu Gly Gly Gly Thr Gly<br>     80                   85                   90 | 291 |
| tct cag ctc ttt cct ctg aca agc aca aga gct acg cct gct gta cct<br>Ser Gln Leu Phe Pro Leu Thr Ser Thr Arg Ala Thr Pro Ala Val Pro<br>95                 100                 105               110 | 339 |
| gtt gga gga tgt tac agg ctt att gat atc cct atg agt aac tgc ttc<br>Val Gly Gly Cys Tyr Arg Leu Ile Asp Ile Pro Met Ser Asn Cys Phe<br>               115                 120               125 | 387 |
| aac agt ggt ata aat aag ata ttt gtg atg agt cag ttc aat tct act<br>Asn Ser Gly Ile Asn Lys Ile Phe Val Met Ser Gln Phe Asn Ser Thr<br>         130                 135               140 | 435 |
| tcg ctt aac cgc cat att cat cgt aca tac ctt gaa ggc ggg atc aac<br>Ser Leu Asn Arg His Ile His Arg Thr Tyr Leu Glu Gly Gly Ile Asn<br>         145                 150               155 | 483 |
| ttt gct gat gga tct gta cag gta tta gcg gct aca caa atg cct gaa<br>Phe Ala Asp Gly Ser Val Gln Val Leu Ala Ala Thr Gln Met Pro Glu<br>160                165                 170 | 531 |
| gag cca gct gga tgg ttc cag ggt aca gca gac tct atc aga aaa ttt<br>Glu Pro Ala Gly Trp Phe Gln Gly Thr Ala Asp Ser Ile Arg Lys Phe<br>175                180                 185               190 | 579 |
| atc tgg gta ctc gag gat tat tac agt cac aaa tcc att gac aac att<br>Ile Trp Val Leu Glu Asp Tyr Tyr Ser His Lys Ser Ile Asp Asn Ile<br>               195                 200               205 | 627 |
| gta atc ttg agt ggc gat cag ctt tat cgg atg aat tac atg gaa ctt<br>Val Ile Leu Ser Gly Asp Gln Leu Tyr Arg Met Asn Tyr Met Glu Leu<br>         210                 215               220 | 675 |
| gtg cag aaa cat gtc gag gac gat gct gat atc act ata tca tgt gct<br>Val Gln Lys His Val Glu Asp Asp Ala Asp Ile Thr Ile Ser Cys Ala<br>               225                 230               235 | 723 |
| cct gtt gat gag agc cga gct tct aaa aat ggg cta gtg aag att gat<br>Pro Val Asp Glu Ser Arg Ala Ser Lys Asn Gly Leu Val Lys Ile Asp<br>         240                 245               250 | 771 |
| cat act gga cgt gta ctt caa ttc ttt gaa aaa cca aag ggt gct gat<br>His Thr Gly Arg Val Leu Gln Phe Phe Glu Lys Pro Lys Gly Ala Asp<br>255                260                 265               270 | 819 |
| ttg aat tct atg aga gtt gag acc aac ttc ctg agc tat gct ata gat<br>Leu Asn Ser Met Arg Val Glu Thr Asn Phe Leu Ser Tyr Ala Ile Asp<br>               275                 280               285 | 867 |
| gat gca cag aaa tat cca tac ctt gca tca atg ggc att tat gtc ttc<br>Asp Ala Gln Lys Tyr Pro Tyr Leu Ala Ser Met Gly Ile Tyr Val Phe<br>         290                 295               300 | 915 |
| aag aaa gat gca ctt tta gac ctt ctc aag tca aaa tat act caa tta<br>Lys Lys Asp Ala Leu Leu Asp Leu Leu Lys Ser Lys Tyr Thr Gln Leu<br>305                310                 315 | 963 |
| cat gac ttt gga tct gaa atc ctc cca aga gct gta cta gat cay agt<br>His Asp Phe Gly Ser Glu Ile Leu Pro Arg Ala Val Leu Asp His Ser<br>         320                 325               330 | 1011 |
| gtg cag gca tgc att ttt acg ggc tat tgg gag gat gtt gga aca atc<br>Val Gln Ala Cys Ile Phe Thr Gly Tyr Trp Glu Asp Val Gly Thr Ile<br>335                340                 345               350 | 1059 |
| aaa tca ttc ttt gat gca aac ttg gcc ctc act gag cag cct tcc aag<br>Lys Ser Phe Phe Asp Ala Asn Leu Ala Leu Thr Glu Gln Pro Ser Lys<br>               355                 360               365 | 1107 |
| ttt gat ttt tac gat cca aaa aca cct ttc ttc act gca ccc cga tgc<br>Phe Asp Phe Tyr Asp Pro Lys Thr Pro Phe Phe Thr Ala Pro Arg Cys<br>         370                 375               380 | 1155 |

```
ttg cct ccg acg caa ttg gac aag tgc aag atg aaa tat gca ttt atc   1203
Leu Pro Pro Thr Gln Leu Asp Lys Cys Lys Met Lys Tyr Ala Phe Ile
        385                 390                 395 tca cay ggt tgc tta ctg aga gaa tgc aac atc gag cat tct gtg att   1251
Ser His Gly Cys Leu Leu Arg Glu Cys Asn Ile Glu His Ser Val Ile
400                 405                 410 gga gtc tgc tca cgt gtc agc tct gga tgt gaa ctc aag gac tcc gtg   1299
Gly Val Cys Ser Arg Val Ser Ser Gly Cys Glu Leu Lys Asp Ser Val
415                 420                 425                 430 atg atg gga gcg gac atc tat gaa act gaa gaa gaa gct tca aag cta   1347
Met Met Gly Ala Asp Ile Tyr Glu Thr Glu Glu Glu Ala Ser Lys Leu
                435                 440                 445 ctg tta gct ggg aag gtc ccr ath gga ata gga agg aac aca aag ata   1395
Leu Leu Ala Gly Lys Val Pro Ile Gly Ile Gly Arg Asn Thr Lys Ile
            450                 455                 460 agg aac tgt atc att gac atg aat gct agg att ggg aag aac gtg gtg   1443
Arg Asn Cys Ile Ile Asp Met Asn Ala Arg Ile Gly Lys Asn Val Val
465                 470                 475 atc aca aac agt aag ggc atc caa gag gct gat cac ccg gaa gaa ggg   1491
Ile Thr Asn Ser Lys Gly Ile Gln Glu Ala Asp His Pro Glu Glu Gly
480                 485                 490 tac tac ata agg tct gga atc gtg gtg atc ctg aag aat gca acc atc   1539
Tyr Tyr Ile Arg Ser Gly Ile Val Val Ile Leu Lys Asn Ala Thr Ile
495                 500                 505                 510 aac gat ggg tct gtc ata tagatcggct gcgtktgcg                      1576
Asn Asp Gly Ser Val Ile
                515

<210> SEQ ID NO 20
<211> LENGTH: 516
<212> TYPE: PRT
<213> ORGANISM: Zea mays

<400> SEQUENCE: 20

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
            85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190
```

Val Leu Glu Asp Tyr Tyr Ser His Lys Ser Ile Asp Asn Ile Val Ile
            195                 200                 205

Leu Ser Gly Asp Gln Leu Tyr Arg Met Asn Tyr Met Glu Leu Val Gln
        210                 215                 220

Lys His Val Glu Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser His
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
            420                 425                 430

Gly Ala Asp Ile Tyr Glu Thr Glu Glu Glu Ala Ser Lys Leu Leu Leu
        435                 440                 445

Ala Gly Lys Val Pro Ile Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515

<210> SEQ ID NO 21
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation -continued

```
<222> LOCATION: (321)
<223> OTHER INFORMATION: n = a or g or c or t/u, unknown, or other.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 21 ggaggagat atg cag ttt gca ctt gca ttg gac acg aac tca ggt cct cac      51
          Met Gln Phe Ala Leu Ala Leu Asp Thr Asn Ser Gly Pro His
          1               5                   10 cag ata aga tct tgt gag ggt gat ggg att gac agg ttg gaa aaa tta        99
Gln Ile Arg Ser Cys Glu Gly Asp Gly Ile Asp Arg Leu Glu Lys Leu
 15              20                  25                  30 agt att ggg ggc aga aag cag gag aaa gct ttg aga aat agg tgc ttt       147
Ser Ile Gly Gly Arg Lys Gln Glu Lys Ala Leu Arg Asn Arg Cys Phe
             35                  40                  45 ggt ggt aga gtt gct gca act aca caa tgt att ctt acc tca gat gct       195
Gly Gly Arg Val Ala Ala Thr Thr Gln Cys Ile Leu Thr Ser Asp Ala
         50                  55                  60 tgt cct gaa act ctt cat tct caa aca cag tcc tct agg aaa aat tat       243
Cys Pro Glu Thr Leu His Ser Gln Thr Gln Ser Ser Arg Lys Asn Tyr
     65                  70                  75 gct gat gca aac cgt gta tct gck atc att ttg ggc gga ggc act gga       291
Ala Asp Ala Asn Arg Val Ser Ala Ile Ile Leu Gly Gly Gly Thr Gly
 80                  85                  90 tct cag ctc ttt cct ctg aca agc aca acn gct acg cct gct gta cct       339
Ser Gln Leu Phe Pro Leu Thr Ser Thr Thr Ala Thr Pro Ala Val Pro
 95                 100                 105                 110 gtt gga gga tgt tac agg ctt att gat atc cct atg agt aac tgc ttc       387
Val Gly Gly Cys Tyr Arg Leu Ile Asp Ile Pro Met Ser Asn Cys Phe
                115                 120                 125 aac agt ggt ata aat aag ata ttt gtg atg agt cag ttc aat tct act       435
Asn Ser Gly Ile Asn Lys Ile Phe Val Met Ser Gln Phe Asn Ser Thr
            130                 135                 140 tcg ctt aac cgc cat att cat cgt aca tac ctt gaa ggc ggg atc aac       483
Ser Leu Asn Arg His Ile His Arg Thr Tyr Leu Glu Gly Gly Ile Asn
        145                 150                 155 ttt gct gat gga tct gta cag gta tta gcg gct aca caa atg cct gaa       531
Phe Ala Asp Gly Ser Val Gln Val Leu Ala Ala Thr Gln Met Pro Glu
    160                 165                 170 gag cca gct gga tgg ttc cag ggt aca gca gac tct atc aga aaa ttt       579
Glu Pro Ala Gly Trp Phe Gln Gly Thr Ala Asp Ser Ile Arg Lys Phe
175                 180                 185                 190 atc tgg gta ctc gag gat tat tac agt cac aaa tcc att gac aac att       627
Ile Trp Val Leu Glu Asp Tyr Tyr Ser His Lys Ser Ile Asp Asn Ile
                195                 200                 205 gta atc ttg agt ggc gat cag ctt tat cgg atg aat tac atg gaa ctt       675
Val Ile Leu Ser Gly Asp Gln Leu Tyr Arg Met Asn Tyr Met Glu Leu
            210                 215                 220 gtg cag aaa cat gtc gag gac gat gct gat atc act ata tca tgt gct       723
Val Gln Lys His Val Glu Asp Asp Ala Asp Ile Thr Ile Ser Cys Ala
        225                 230                 235 cct gtt gat gag agc cga gct tct aaa aat ggg cta gtg aag att gat       771
Pro Val Asp Glu Ser Arg Ala Ser Lys Asn Gly Leu Val Lys Ile Asp
    240                 245                 250
```

```
cat act gga cgt gta ctt caa ttc ttt gaa aaa cca aag ggt gct gat        819
His Thr Gly Arg Val Leu Gln Phe Phe Glu Lys Pro Lys Gly Ala Asp
255                 260                 265                 270 ttg aat tct atg aga gtt gag acc aac ttc ctg agc tat gct ata gat        867
Leu Asn Ser Met Arg Val Glu Thr Asn Phe Leu Ser Tyr Ala Ile Asp
                275                 280                 285 gat gca cag aaa tat cca tac ctt gca tca atg ggc att tat gtc ttc        915
Asp Ala Gln Lys Tyr Pro Tyr Leu Ala Ser Met Gly Ile Tyr Val Phe
            290                 295                 300 aag aaa gat gca ctt tta gac ctt ctc aag tca aaa tat act caa tta        963
Lys Lys Asp Ala Leu Leu Asp Leu Leu Lys Ser Lys Tyr Thr Gln Leu
        305                 310                 315 cat gac ttt gga tct gaa atc ctc cca aga gct gta cta gat cay agt       1011
His Asp Phe Gly Ser Glu Ile Leu Pro Arg Ala Val Leu Asp His Ser
    320                 325                 330 gtg cag gca tgc att ttt acg ggc tat tgg gag gat gtt gga aca atc       1059
Val Gln Ala Cys Ile Phe Thr Gly Tyr Trp Glu Asp Val Gly Thr Ile
335                 340                 345                 350 aaa tca ttc ttt gat gca aac ttg gcc ctc act gag cag cct tcc aag       1107
Lys Ser Phe Phe Asp Ala Asn Leu Ala Leu Thr Glu Gln Pro Ser Lys
                355                 360                 365 ttt gat ttt tac gat cca aaa aca cct ttc ttc act gca ccc cga tgc       1155
Phe Asp Phe Tyr Asp Pro Lys Thr Pro Phe Phe Thr Ala Pro Arg Cys
            370                 375                 380 ttg cct ccg acg caa ttg gac aag tgc aag atg aaa tat gca ttt atc       1203
Leu Pro Pro Thr Gln Leu Asp Lys Cys Lys Met Lys Tyr Ala Phe Ile
        385                 390                 395 tca gat ggt tgc tta ctg aga gaa tgc aac atc gag cat tct gtg att       1251
Ser Asp Gly Cys Leu Leu Arg Glu Cys Asn Ile Glu His Ser Val Ile
    400                 405                 410 gga gtc tgc tca cgt gtc agc tct gga tgt gaa ctc aag gac tcc gtg       1299
Gly Val Cys Ser Arg Val Ser Ser Gly Cys Glu Leu Lys Asp Ser Val
415                 420                 425                 430 atg atg gga gcg gac atc tat gaa act gaa gaa gct tca aag cta           1347
Met Met Gly Ala Asp Ile Tyr Glu Thr Glu Glu Ala Ser Lys Leu
                435                 440                 445 ctg tta gct ggg aag gtc ccr gtt gga ata gga agg aac aca aag ata       1395
Leu Leu Ala Gly Lys Val Pro Val Gly Ile Gly Arg Asn Thr Lys Ile
            450                 455                 460 agg aac tgt atc att gac atg aat gct agg att ggg aag aac gtg gtg       1443
Arg Asn Cys Ile Ile Asp Met Asn Ala Arg Ile Gly Lys Asn Val Val
        465                 470                 475 atc aca aac agt aag ggc atc caa gag gct gat cac ccg gaa gaa ggg       1491
Ile Thr Asn Ser Lys Gly Ile Gln Glu Ala Asp His Pro Glu Glu Gly
    480                 485                 490 tac tac ata agg tct gga atc gtg gtg atc ctg aag aat gca acc atc       1539
Tyr Tyr Ile Arg Ser Gly Ile Val Val Ile Leu Lys Asn Ala Thr Ile
495                 500                 505                 510 aac gat ggg tct gtc ata tagatcggct gcgtktgcg                          1576
Asn Asp Gly Ser Val Ile
                515

<210> SEQ ID NO 22
<211> LENGTH: 516
<212> TYPE: PRT
<213> ORGANISM: Zea mays

<400> SEQUENCE: 22

Met Gln Phe Ala Leu Ala Leu Asp Thr Asn Ser Gly Pro His Gln Ile
1               5                   10                  15
```

-continued

```
Arg Ser Cys Glu Gly Asp Gly Ile Asp Arg Leu Glu Lys Leu Ser Ile
         20                  25                  30
Gly Gly Arg Lys Gln Glu Lys Ala Leu Arg Asn Arg Cys Phe Gly Gly
         35                  40                  45
Arg Val Ala Ala Thr Thr Gln Cys Ile Leu Thr Ser Asp Ala Cys Pro
 50                  55                  60
Glu Thr Leu His Ser Gln Thr Gln Ser Ser Arg Lys Asn Tyr Ala Asp
 65                  70                  75                  80
Ala Asn Arg Val Ser Ala Ile Ile Leu Gly Gly Thr Gly Ser Gln
                 85                  90                  95
Leu Phe Pro Leu Thr Ser Thr Thr Ala Thr Pro Ala Val Pro Val Gly
             100                 105                 110
Gly Cys Tyr Arg Leu Ile Asp Ile Pro Met Ser Asn Cys Phe Asn Ser
             115                 120                 125
Gly Ile Asn Lys Ile Phe Val Met Ser Gln Phe Asn Ser Thr Ser Leu
         130                 135                 140
Asn Arg His Ile His Arg Thr Tyr Leu Glu Gly Ile Asn Phe Ala
145                 150                 155                 160
Asp Gly Ser Val Gln Val Leu Ala Ala Thr Gln Met Pro Glu Glu Pro
                 165                 170                 175
Ala Gly Trp Phe Gln Gly Thr Ala Asp Ser Ile Arg Lys Phe Ile Trp
             180                 185                 190
Val Leu Glu Asp Tyr Tyr Ser His Lys Ser Ile Asp Asn Ile Val Ile
         195                 200                 205
Leu Ser Gly Asp Gln Leu Tyr Arg Met Asn Tyr Met Glu Leu Val Gln
     210                 215                 220
Lys His Val Glu Asp Asp Ala Asp Ile Thr Ile Ser Cys Ala Pro Val
225                 230                 235                 240
Asp Glu Ser Arg Ala Ser Lys Asn Gly Leu Val Lys Ile Asp His Thr
                 245                 250                 255
Gly Arg Val Leu Gln Phe Phe Glu Lys Pro Lys Gly Ala Asp Leu Asn
             260                 265                 270
Ser Met Arg Val Glu Thr Asn Phe Leu Ser Tyr Ala Ile Asp Asp Ala
         275                 280                 285
Gln Lys Tyr Pro Tyr Leu Ala Ser Met Gly Ile Tyr Val Phe Lys Lys
     290                 295                 300
Asp Ala Leu Leu Asp Leu Leu Lys Ser Lys Tyr Thr Gln Leu His Asp
305                 310                 315                 320
Phe Gly Ser Glu Ile Leu Pro Arg Ala Val Leu Asp His Ser Val Gln
                 325                 330                 335
Ala Cys Ile Phe Thr Gly Tyr Trp Glu Asp Val Gly Thr Ile Lys Ser
             340                 345                 350
Phe Phe Asp Ala Asn Leu Ala Leu Thr Glu Gln Pro Ser Lys Phe Asp
         355                 360                 365
Phe Tyr Asp Pro Lys Thr Pro Phe Phe Thr Ala Pro Arg Cys Leu Pro
     370                 375                 380
Pro Thr Gln Leu Asp Lys Cys Lys Met Lys Tyr Ala Phe Ile Ser Asp
385                 390                 395                 400
Gly Cys Leu Leu Arg Glu Cys Asn Ile Glu His Ser Val Ile Gly Val
                 405                 410                 415
Cys Ser Arg Val Ser Ser Gly Cys Glu Leu Lys Asp Ser Val Met Met
             420                 425                 430
Gly Ala Asp Ile Tyr Glu Thr Glu Glu Glu Ala Ser Lys Leu Leu Leu
         435                 440                 445
```

```
Ala Gly Lys Val Pro Val Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515

<210> SEQ ID NO 23
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1389)
<223> OTHER INFORMATION: h = a or c or t/u.
<220> FEATURE:
<221> NAME/KEY: variation
<222> LOCATION: (1572)
<223> OTHER INFORMATION: k = g or t.

<400> SEQUENCE: 23 ggaggagat atg cag ttt gca ctt gca ttg gac acg aac tca ggt cct cac      51
          Met Gln Phe Ala Leu Ala Leu Asp Thr Asn Ser Gly Pro His
          1               5                   10 cag ata aga tct tgt gag ggt gat ggg att gac agg ttg gaa aaa tta        99
Gln Ile Arg Ser Cys Glu Gly Asp Gly Ile Asp Arg Leu Glu Lys Leu
15                  20                  25                  30 agt att ggg ggc aga aag cag gag aaa gct ttg aga aat agg tgc ttt       147
Ser Ile Gly Gly Arg Lys Gln Glu Lys Ala Leu Arg Asn Arg Cys Phe
                35                  40                  45 ggt ggt aga gtt gct gca act aca caa tgt att ctt acc tca gat gct       195
Gly Gly Arg Val Ala Ala Thr Thr Gln Cys Ile Leu Thr Ser Asp Ala
            50                  55                  60 tgt cct gaa act ctt cat tct caa aca cag tcc tct agg aaa aat tat       243
Cys Pro Glu Thr Leu His Ser Gln Thr Gln Ser Ser Arg Lys Asn Tyr
65                  70                  75 gct gat gca aac cgt gta tct gck atc att ttg ggc gga ggc act gga       291
Ala Asp Ala Asn Arg Val Ser Ala Ile Ile Leu Gly Gly Gly Thr Gly
    80                  85                  90 tct cag ctc ttt cct ctg aca agc aca aga gct acg cct gct gta cct       339
Ser Gln Leu Phe Pro Leu Thr Ser Thr Arg Ala Thr Pro Ala Val Pro
95                  100                 105                 110 gtt gga gga tgt tac agg ctt att gat atc cct atg agt aac tgc ttc       387
Val Gly Gly Cys Tyr Arg Leu Ile Asp Ile Pro Met Ser Asn Cys Phe
                115                 120                 125
```

|  |  |  |  |  |  |  |  |  |  |  |  |  |  |  |  |
|---|---|---|---|---|---|---|---|---|---|---|---|---|---|---|---|
| aac | agt | ggt | ata | aat | aag | ata | ttt | gtg | atg | agt | cag | ttc | aat | tct | act | 435
| Asn | Ser | Gly | Ile | Asn | Lys | Ile | Phe | Val | Met | Ser | Gln | Phe | Asn | Ser | Thr |
|  |  |  | 130 |  |  |  | 135 |  |  |  |  | 140 |  |  |  |

```
aac agt ggt ata aat aag ata ttt gtg atg agt cag ttc aat tct act        435
Asn Ser Gly Ile Asn Lys Ile Phe Val Met Ser Gln Phe Asn Ser Thr
            130                 135                 140 tcg ctt aac cgc cat att cat cgt aca tac ctt gaa ggc ggg atc aac        483
Ser Leu Asn Arg His Ile His Arg Thr Tyr Leu Glu Gly Gly Ile Asn
                145                 150                 155 ttt gct gat gga tct gta cag gta tta gcg gct aca caa atg cct gaa        531
Phe Ala Asp Gly Ser Val Gln Val Leu Ala Ala Thr Gln Met Pro Glu
    160                 165                 170 gag cca gct gga tgg ttc cag ggt aca gca gac tct atc aga aaa ttt        579
Glu Pro Ala Gly Trp Phe Gln Gly Thr Ala Asp Ser Ile Arg Lys Phe
175                 180                 185                 190 atc tgg gta ctc gag gat tat tac agt cac aaa tcc att gac aac att        627
Ile Trp Val Leu Glu Asp Tyr Tyr Ser His Lys Ser Ile Asp Asn Ile
                195                 200                 205 gta atc ttg agt ggc gat cag ctt tat cgg atg aat tac atg gaa ctt        675
Val Ile Leu Ser Gly Asp Gln Leu Tyr Arg Met Asn Tyr Met Glu Leu
                210                 215                 220 gtg cag aaa cat gtc gag gac gat gct gat atc act ata tca tgt gct        723
Val Gln Lys His Val Glu Asp Asp Ala Asp Ile Thr Ile Ser Cys Ala
                225                 230                 235 cct gtt gat gag agc cga gct tct aaa aat ggg cta gtg aag att gat        771
Pro Val Asp Glu Ser Arg Ala Ser Lys Asn Gly Leu Val Lys Ile Asp
240                 245                 250 cat act gga cgt gta ctt caa ttc ttt gaa aaa cca aag ggt gct gat        819
His Thr Gly Arg Val Leu Gln Phe Phe Glu Lys Pro Lys Gly Ala Asp
255                 260                 265                 270 ttg aat tct atg aga gtt gag acc aac ttc ctg agc tat gct ata gat        867
Leu Asn Ser Met Arg Val Glu Thr Asn Phe Leu Ser Tyr Ala Ile Asp
                275                 280                 285 gat gca cag aaa tat cca tac ctt gca tca atg gga att tat gtc ttc        915
Asp Ala Gln Lys Tyr Pro Tyr Leu Ala Ser Met Gly Ile Tyr Val Phe
            290                 295                 300 aag aaa gat gca ctt tta gac ctt ctc aag tca aaa tat act caa tta        963
Lys Lys Asp Ala Leu Leu Asp Leu Leu Lys Ser Lys Tyr Thr Gln Leu
                305                 310                 315 cat gac ttt gga tct gaa atc ctc cca aga gct gta cta gat tay agt       1011
His Asp Phe Gly Ser Glu Ile Leu Pro Arg Ala Val Leu Asp Tyr Ser
        320                 325                 330 gtg cag gca tgc att ttt acg ggc tat tgg gag gat gtt gga aca atc       1059
Val Gln Ala Cys Ile Phe Thr Gly Tyr Trp Glu Asp Val Gly Thr Ile
335                 340                 345                 350 aaa tca ttc ttt gat gca aac ttg gcc ctc act gag cag cct tcc aag       1107
Lys Ser Phe Phe Asp Ala Asn Leu Ala Leu Thr Glu Gln Pro Ser Lys
                355                 360                 365 ttt gat ttt tac gat cca aaa aca cct ttc ttc act gca ccc cga tgc       1155
Phe Asp Phe Tyr Asp Pro Lys Thr Pro Phe Phe Thr Ala Pro Arg Cys
            370                 375                 380 ttg cct ccg acg caa ttg gac aag tgc aag atg aaa tat gca ttt atc       1203
Leu Pro Pro Thr Gln Leu Asp Lys Cys Lys Met Lys Tyr Ala Phe Ile
                385                 390                 395 tca gat ggt tgc tta ctg aga gaa tgc aac atc gag cat tct gtg att       1251
Ser Asp Gly Cys Leu Leu Arg Glu Cys Asn Ile Glu His Ser Val Ile
400                 405                 410 gga gtc tgc tca cgt gtc agc tct gga tgt gaa ctc aag gac tcc gtg       1299
Gly Val Cys Ser Arg Val Ser Ser Gly Cys Glu Leu Lys Asp Ser Val
415                 420                 425                 430 atg atg gga gcg gac atc tat gaa act gaa gaa gaa gct tca aag cta       1347
Met Met Gly Ala Asp Ile Tyr Glu Thr Glu Glu Glu Ala Ser Lys Leu
                435                 440                 445
```

```
ctg tta gct ggg aag gtc ccr gtt gga ata gga agg aac ath aag ata    1395
Leu Leu Ala Gly Lys Val Pro Val Gly Ile Gly Arg Asn Ile Lys Ile
            450                 455                 460 agg aac tgt atc att gac atg aat gct agg att ggg aag aac gtg gtg    1443
Arg Asn Cys Ile Ile Asp Met Asn Ala Arg Ile Gly Lys Asn Val Val
        465                 470                 475 atc aca aac agt aag ggc atc caa gag gct gat cac ccg gaa gaa ggg    1491
Ile Thr Asn Ser Lys Gly Ile Gln Glu Ala Asp His Pro Glu Glu Gly
480                 485                 490 tac tac ata agg tct gga atc gtg gtg atc ctg aag aat gca acc atc    1539
Tyr Tyr Ile Arg Ser Gly Ile Val Val Ile Leu Lys Asn Ala Thr Ile
495                 500                 505                 510 aac gat ggg tct gtc ata tagatcggct gcgtktgcg                       1576
Asn Asp Gly Ser Val Ile
                515

<210> SEQ ID NO 24
<211> LENGTH: 516
<212> TYPE: PRT
<213> ORGANISM: Zea mays

<400> SEQUENCE: 24

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270
```

```
Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Tyr Ser Val Gln
                325                 330                 335

Ala Cys Ile Phe Thr Gly Tyr Trp Glu Asp Val Gly Thr Ile Lys Ser
                340                 345                 350

Phe Phe Asp Ala Asn Leu Ala Leu Thr Glu Gln Pro Ser Lys Phe Asp
                355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
                420                 425                 430

Gly Ala Asp Ile Tyr Glu Thr Glu Glu Glu Ala Ser Lys Leu Leu Leu
                435                 440                 445

Ala Gly Lys Val Pro Val Gly Ile Gly Arg Asn Ile Lys Ile Arg Asn
                450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
                500                 505                 510

Gly Ser Val Ile
        515

<210> SEQ ID NO 25
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (657)
<223> OTHER INFORMATION: n = a or g or c or t/u, unknown, or other.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 25
```

```
ggaggagat atg cag ttt gca ctt gca ttg gac acg aac tca ggt cct cac      51
        Met Gln Phe Ala Leu Ala Leu Asp Thr Asn Ser Gly Pro His
          1               5                  10 cag ata aga tct tgt gag ggt gat ggg att gac agg ttg gaa aaa tta         99
Gln Ile Arg Ser Cys Glu Gly Asp Gly Ile Asp Arg Leu Glu Lys Leu
 15              20                  25                  30 agt att ggg ggc aga aag cag gag aaa gct ttg aga aat agg tgc ttt        147
Ser Ile Gly Gly Arg Lys Gln Glu Lys Ala Leu Arg Asn Arg Cys Phe
                 35                  40                  45 ggt gga aga gtt gct gca act aca caa tgt att ctt acc tca gat gct        195
Gly Gly Arg Val Ala Ala Thr Thr Gln Cys Ile Leu Thr Ser Asp Ala
             50                  55                  60 tgt cct gaa act ctt cat tct caa aca cag tcc tct agg aaa aat tat        243
Cys Pro Glu Thr Leu His Ser Gln Thr Gln Ser Ser Arg Lys Asn Tyr
         65                  70                  75 gct gat gca aac cgt gta tct gck atc att ttg ggc gga ggc act gga        291
Ala Asp Ala Asn Arg Val Ser Ala Ile Ile Leu Gly Gly Gly Thr Gly
     80                  85                  90 tct cag ctc ttt cct ctg aca agc aca aga gct acg cct gct gta cct        339
Ser Gln Leu Phe Pro Leu Thr Ser Thr Arg Ala Thr Pro Ala Val Pro
 95                 100                 105                 110 gtt gga gga tgt tac agg ctt att gat atc cct atg agt aac tgc ttc        387
Val Gly Gly Cys Tyr Arg Leu Ile Asp Ile Pro Met Ser Asn Cys Phe
                115                 120                 125 aac agt ggt ata aat aag ata ttt gtg atg agt cag ttc aat tct act        435
Asn Ser Gly Ile Asn Lys Ile Phe Val Met Ser Gln Phe Asn Ser Thr
            130                 135                 140 tcg ctt aac cgc cat att cat cgt aca tac ctt gaa ggc ggg atc aac        483
Ser Leu Asn Arg His Ile His Arg Thr Tyr Leu Glu Gly Gly Ile Asn
        145                 150                 155 ttt gct gat gga tct gta cag gta tta gcg gct aca caa atg cct gaa        531
Phe Ala Asp Gly Ser Val Gln Val Leu Ala Ala Thr Gln Met Pro Glu
    160                 165                 170 gag cca gct gga tgg ttc cag ggt aca gca gac tct atc aga aaa ttt        579
Glu Pro Ala Gly Trp Phe Gln Gly Thr Ala Asp Ser Ile Arg Lys Phe
175                 180                 185                 190 atc tgg gta ctc gag gat tat tac agt cac aaa tcc att gac aac att        627
Ile Trp Val Leu Glu Asp Tyr Tyr Ser His Lys Ser Ile Asp Asn Ile
                195                 200                 205 gta atc ttg agt ggc gat cag ctt tat ccn atg aat tac atg gaa ctt        675
Val Ile Leu Ser Gly Asp Gln Leu Tyr Pro Met Asn Tyr Met Glu Leu
            210                 215                 220 gtg cag aaa cat gtc gag gac gat gct gat atc act ata tca tgt gct        723
Val Gln Lys His Val Glu Asp Asp Ala Asp Ile Thr Ile Ser Cys Ala
        225                 230                 235 cct gtt gat gag agc cga gct tct aaa aat ggg cta gtg aag att gat        771
Pro Val Asp Glu Ser Arg Ala Ser Lys Asn Gly Leu Val Lys Ile Asp
    240                 245                 250 cat act gga cgt gta ctt caa ttc ttt gaa aaa cca aag ggt gct gat        819
His Thr Gly Arg Val Leu Gln Phe Phe Glu Lys Pro Lys Gly Ala Asp
255                 260                 265                 270 ttg aat tct atg aga gtt gag acc aac ttc ctg agc tat gct ata gat        867
Leu Asn Ser Met Arg Val Glu Thr Asn Phe Leu Ser Tyr Ala Ile Asp
                275                 280                 285 gat gca cag aaa tat cca tac ctt gca tca atg ggc att tat gtc ttc        915
Asp Ala Gln Lys Tyr Pro Tyr Leu Ala Ser Met Gly Ile Tyr Val Phe
            290                 295                 300 aag aaa gat gca ctt tta gac ctt ctc aag tca aaa tat act caa tta        963
Lys Lys Asp Ala Leu Leu Asp Leu Leu Lys Ser Lys Tyr Thr Gln Leu
        305                 310                 315
```

| | | | | | | | | | | | | | | | | |
|---|---|---|---|---|---|---|---|---|---|---|---|---|---|---|---|---|
| cat | gac | ttt | gga | tct | gaa | atc | ctc | cca | aga | gct | gta | cta | gat | tay | agt | 1011 |
| His | Asp | Phe | Gly | Ser | Glu | Ile | Leu | Pro | Arg | Ala | Val | Leu | Asp | Tyr | Ser | |
| | 320 | | | | 325 | | | | | 330 | | | | | | |
| gtg | cag | gca | tgc | att | ttt | acg | ggc | tat | tgg | gag | gat | gtt | gga | aca | atc | 1059 |
| Val | Gln | Ala | Cys | Ile | Phe | Thr | Gly | Tyr | Trp | Glu | Asp | Val | Gly | Thr | Ile | |
| 335 | | | | | 340 | | | | | 345 | | | | | 350 | |
| aaa | tca | ttc | ttt | gat | gca | aac | ttg | gcc | ctc | act | gag | cag | cct | tcc | aag | 1107 |
| Lys | Ser | Phe | Phe | Asp | Ala | Asn | Leu | Ala | Leu | Thr | Glu | Gln | Pro | Ser | Lys | |
| | | | | 355 | | | | | 360 | | | | | 365 | | |
| ttt | gat | ttt | tac | gat | cca | aaa | aca | cct | ttc | ttc | act | gca | ccc | cga | tgc | 1155 |
| Phe | Asp | Phe | Tyr | Asp | Pro | Lys | Thr | Pro | Phe | Phe | Thr | Ala | Pro | Arg | Cys | |
| | | | 370 | | | | | 375 | | | | | 380 | | | |
| ttg | cct | ccg | acg | caa | ttg | gac | aag | tgc | aag | atg | aaa | tat | gca | ttt | atc | 1203 |
| Leu | Pro | Pro | Thr | Gln | Leu | Asp | Lys | Cys | Lys | Met | Lys | Tyr | Ala | Phe | Ile | |
| | | 385 | | | | | 390 | | | | | 395 | | | | |
| tca | gat | ggt | tgc | tta | ctg | aga | gaa | tgc | aac | atc | gag | cat | tct | gtg | att | 1251 |
| Ser | Asp | Gly | Cys | Leu | Leu | Arg | Glu | Cys | Asn | Ile | Glu | His | Ser | Val | Ile | |
| | 400 | | | | 405 | | | | | 410 | | | | | | |
| gga | gtc | tgc | tca | cgt | gtc | agc | tct | gga | tgt | gaa | ctc | aag | gac | tcc | gtg | 1299 |
| Gly | Val | Cys | Ser | Arg | Val | Ser | Ser | Gly | Cys | Glu | Leu | Lys | Asp | Ser | Val | |
| 415 | | | | | 420 | | | | | 425 | | | | | 430 | |
| atg | atg | gga | gcg | gac | atc | tat | gaa | act | gaa | gaa | gaa | gct | tca | aag | cta | 1347 |
| Met | Met | Gly | Ala | Asp | Ile | Tyr | Glu | Thr | Glu | Glu | Glu | Ala | Ser | Lys | Leu | |
| | | | | 435 | | | | | 440 | | | | | 445 | | |
| ctg | tta | gct | ggg | aag | gtc | ccr | gtt | gga | ata | gga | agg | aac | aca | aag | ata | 1395 |
| Leu | Leu | Ala | Gly | Lys | Val | Pro | Val | Gly | Ile | Gly | Arg | Asn | Thr | Lys | Ile | |
| | | | 450 | | | | | 455 | | | | | 460 | | | |
| agg | aac | tgt | atc | att | gac | atg | aat | gct | agg | att | ggg | aag | aac | gtg | gtg | 1443 |
| Arg | Asn | Cys | Ile | Ile | Asp | Met | Asn | Ala | Arg | Ile | Gly | Lys | Asn | Val | Val | |
| | | 465 | | | | | 470 | | | | | 475 | | | | |
| atc | aca | aac | agt | aag | ggc | atc | caa | gag | gct | gat | cac | ccg | gaa | gaa | ggg | 1491 |
| Ile | Thr | Asn | Ser | Lys | Gly | Ile | Gln | Glu | Ala | Asp | His | Pro | Glu | Glu | Gly | |
| | 480 | | | | 485 | | | | | 490 | | | | | | |
| tac | tac | ata | agg | tct | gga | atc | gtg | gtg | atc | ctg | aag | aat | gca | acc | atc | 1539 |
| Tyr | Tyr | Ile | Arg | Ser | Gly | Ile | Val | Val | Ile | Leu | Lys | Asn | Ala | Thr | Ile | |
| 495 | | | | | 500 | | | | | 505 | | | | | 510 | |
| aac | gat | ggg | tct | gtc | ata | tagatcggct | gcgtktgcg | | | | | | | | | 1576 |
| Asn | Asp | Gly | Ser | Val | Ile | | | | | | | | | | | |
| | | | | | 515 | | | | | | | | | | | |

<210> SEQ ID NO 26
<211> LENGTH: 516
<212> TYPE: PRT
<213> ORGANISM: Zea mays

<400> SEQUENCE: 26

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly

-continued

```
              100                 105                 110
Gly Cys Tyr Arg Leu Ile Asp Ile Pro Met Ser Asn Cys Phe Asn Ser
            115                 120                 125

Gly Ile Asn Lys Ile Phe Val Met Ser Gln Phe Asn Ser Thr Ser Leu
            130                 135             140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
            195                 200                 205

Leu Ser Gly Asp Gln Leu Tyr Pro Met Asn Tyr Met Glu Leu Val Gln
            210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
                260                 265                 270

Ser Met Arg Val Glu Thr Asn Phe Leu Ser Tyr Ala Ile Asp Asp Ala
                275                 280                 285

Gln Lys Tyr Pro Tyr Leu Ala Ser Met Gly Ile Tyr Val Phe Lys Lys
            290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Tyr Ser Val Gln
                325                 330                 335

Ala Cys Ile Phe Thr Gly Tyr Trp Glu Asp Val Gly Thr Ile Lys Ser
                340                 345                 350

Phe Phe Asp Ala Asn Leu Ala Leu Thr Glu Gln Pro Ser Lys Phe Asp
            355                 360                 365

Phe Tyr Asp Pro Lys Thr Pro Phe Phe Thr Ala Pro Arg Cys Leu Pro
370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
                420                 425                 430

Gly Ala Asp Ile Tyr Glu Thr Glu Glu Ala Ser Lys Leu Leu Leu
            435                 440                 445

Ala Gly Lys Val Pro Val Gly Ile Gly Arg Asn Thr Lys Ile Arg Asn
            450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
                500                 505                 510

Gly Ser Val Ile
            515
```

-continued

```
<210> SEQ ID NO 27
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (540)
<223> OTHER INFORMATION: n = a or g or c or t/u, unknown, or other.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1287)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 27 ggaggagat atg cag ttt gca ctt gca ttg gac acg aac tca ggt cct cac       51
          Met Gln Phe Ala Leu Ala Leu Asp Thr Asn Ser Gly Pro His
           1               5                  10 cag ata aga tct tgt gag ggt gat ggg att gac agg ttg gaa aaa tta         99
Gln Ile Arg Ser Cys Glu Gly Asp Gly Ile Asp Arg Leu Glu Lys Leu
 15              20                  25                  30 agt att ggg ggc aga aag cag gag aaa gct ttg aga aat agg tgc ttt        147
Ser Ile Gly Gly Arg Lys Gln Glu Lys Ala Leu Arg Asn Arg Cys Phe
             35                  40                  45 ggt ggt aga gtt gct gca act aca caa tgt att ctt acc tca gat gct        195
Gly Gly Arg Val Ala Ala Thr Thr Gln Cys Ile Leu Thr Ser Asp Ala
         50                  55                  60 tgt cct gaa act ctt cat tct caa aca cag tcc tct agg aaa aat tat        243
Cys Pro Glu Thr Leu His Ser Gln Thr Gln Ser Ser Arg Lys Asn Tyr
 65                  70                  75 gct gat gca aac cgt gta tct gck atc att ttg ggc gga ggc act gga        291
Ala Asp Ala Asn Arg Val Ser Ala Ile Ile Leu Gly Gly Gly Thr Gly
     80                  85                  90 tct cag ctc ttt cct ctg aca agc aca aga gct acg cct gct gta cct        339
Ser Gln Leu Phe Pro Leu Thr Ser Thr Arg Ala Thr Pro Ala Val Pro
 95                 100                 105                 110 gtt gga gga tgt tac agg ctt att gat atc cct atg agt aac tgc ttc        387
Val Gly Gly Cys Tyr Arg Leu Ile Asp Ile Pro Met Ser Asn Cys Phe
                115                 120                 125 aac agt ggt ata aat aag ata ttt gtg atg agt cag ttc aat tct act        435
Asn Ser Gly Ile Asn Lys Ile Phe Val Met Ser Gln Phe Asn Ser Thr
            130                 135                 140 tcg ctt aac cgc cat att cat cgt aca tac ctt gaa ggc ggg atc aac        483
Ser Leu Asn Arg His Ile His Arg Thr Tyr Leu Glu Gly Gly Ile Asn
        145                 150                 155 ttt gct gat gga tct gta cag gta tta gcg gct aca caa atg cct gaa        531
Phe Ala Asp Gly Ser Val Gln Val Leu Ala Ala Thr Gln Met Pro Glu
    160                 165                 170
```

| | | |
|---|---|---|
| gag cca gtn gga tgg ttc cag ggt aca gca gac tct atc aga aaa ttt<br>Glu Pro Val Gly Trp Phe Gln Gly Thr Ala Asp Ser Ile Arg Lys Phe<br>175                      180                        185                        190 | | 579 |
| atc tgg gta ctc gag gat tat tac agt cac aaa tcc att gac aac att<br>Ile Trp Val Leu Glu Asp Tyr Tyr Ser His Lys Ser Ile Asp Asn Ile<br>                  195                        200                        205 | | 627 |
| gta atc ttg agt ggc gat cag ctt tat cgg atg aat tac atg gaa ctt<br>Val Ile Leu Ser Gly Asp Gln Leu Tyr Arg Met Asn Tyr Met Glu Leu<br>          210                        215                        220 | | 675 |
| gtg cag aaa cat gtc gag gac gat gct gat atc act ata tca tgt gct<br>Val Gln Lys His Val Glu Asp Asp Ala Asp Ile Thr Ile Ser Cys Ala<br>                225                        230                        235 | | 723 |
| cct gtt gat gag agc cga gct tct aaa aat ggg cta gtg aag att gat<br>Pro Val Asp Glu Ser Arg Ala Ser Lys Asn Gly Leu Val Lys Ile Asp<br>240                      245                        250 | | 771 |
| cat act gga cgt gta ctt caa ttc ttt gaa aaa cca aag ggt gct gat<br>His Thr Gly Arg Val Leu Gln Phe Phe Glu Lys Pro Lys Gly Ala Asp<br>255                      260                        265                        270 | | 819 |
| ttg aat tct atg aga gtt gag acc aac ttc ctg agc tat gct ata gat<br>Leu Asn Ser Met Arg Val Glu Thr Asn Phe Leu Ser Tyr Ala Ile Asp<br>                275                        280                        285 | | 867 |
| gat gca cag aaa tat cca tac ctt gca tca atg ggc att tat gtc ttc<br>Asp Ala Gln Lys Tyr Pro Tyr Leu Ala Ser Met Gly Ile Tyr Val Phe<br>          290                        295                        300 | | 915 |
| aag aaa gat gca ctt tta gac ctt ctc aag tca aaa tat act caa tta<br>Lys Lys Asp Ala Leu Leu Asp Leu Leu Lys Ser Lys Tyr Thr Gln Leu<br>                305                        310                        315 | | 963 |
| cat gac ttt gga tct gaa atc ctc cca aga gct gta cta gat cay agt<br>His Asp Phe Gly Ser Glu Ile Leu Pro Arg Ala Val Leu Asp His Ser<br>320                      325                        330 | | 1011 |
| gtg cag gca tgc att ttt acg ggc tat tgg gag gat gtt gga aca atc<br>Val Gln Ala Cys Ile Phe Thr Gly Tyr Trp Glu Asp Val Gly Thr Ile<br>335                      340                        345                        350 | | 1059 |
| aaa tca ttc ttt gat gca aac ttg gcc ctc act gag cag cct tcc aag<br>Lys Ser Phe Phe Asp Ala Asn Leu Ala Leu Thr Glu Gln Pro Ser Lys<br>                355                        360                        365 | | 1107 |
| ttt gat ttt tac gat cca aaa aca cct ttc ttc act gca ccc cga tgc<br>Phe Asp Phe Tyr Asp Pro Lys Thr Pro Phe Phe Thr Ala Pro Arg Cys<br>          370                        375                        380 | | 1155 |
| ttg cct ccg acg caa ttg gac aag tgc aag atg aaa tat gca ttt atc<br>Leu Pro Pro Thr Gln Leu Asp Lys Cys Lys Met Lys Tyr Ala Phe Ile<br>                385                        390                        395 | | 1203 |
| tca gat ggt tgc tta ctg aga gaa tgc aac atc gag cat tct gtg att<br>Ser Asp Gly Cys Leu Leu Arg Glu Cys Asn Ile Glu His Ser Val Ile<br>400                      405                        410 | | 1251 |
| gga gtc tgc tca cgt gtc agc tct gga tgt gaa tty aag gac tcc gtg<br>Gly Val Cys Ser Arg Val Ser Ser Gly Cys Glu Phe Lys Asp Ser Val<br>415                      420                        425                        430 | | 1299 |
| atg atg gga gcg gac atc tat gaa act gaa gaa gaa gct tca aag cta<br>Met Met Gly Ala Asp Ile Tyr Glu Thr Glu Glu Glu Ala Ser Lys Leu<br>                      435                        440                        445 | | 1347 |
| ctg tta gct ggg aag gtc ccr gtt gga ata gga agg aac aca aag ata<br>Leu Leu Ala Gly Lys Val Pro Val Gly Ile Gly Arg Asn Thr Lys Ile<br>                450                        455                        460 | | 1395 |
| agg aac tgt atc att gac atg aat gct agg att ggg aag aac gtg gtg<br>Arg Asn Cys Ile Ile Asp Met Asn Ala Arg Ile Gly Lys Asn Val Val<br>          465                        470                        475 | | 1443 |
| atc aca aac agt aag ggc atc caa gag gct gat cac ccg gaa gaa ggg<br>Ile Thr Asn Ser Lys Gly Ile Gln Glu Ala Asp His Pro Glu Glu Gly<br>480                      485                        490 | | 1491 |

```
tac tac ata agg tct gga atc gtg gtg atc ctg aag aat gca acc atc      1539
Tyr Tyr Ile Arg Ser Gly Ile Val Val Ile Leu Lys Asn Ala Thr Ile
495                 500                 505                 510 aac gat ggg tct gtc ata tagatcggct gcgtktgcg                          1576
Asn Asp Gly Ser Val Ile
                515
```

<210> SEQ ID NO 28
<211> LENGTH: 516
<212> TYPE: PRT
<213> ORGANISM: Zea mays

<400> SEQUENCE: 28

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Val Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335
```

```
Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Phe Lys Asp Ser Val Met Met
            420                 425                 430

Gly Ala Asp Ile Tyr Glu Thr Glu Glu Glu Ala Ser Lys Leu Leu Leu
        435                 440                 445

Ala Gly Lys Val Pro Val Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515

<210> SEQ ID NO 29
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (981)
<223> OTHER INFORMATION: r = g or a.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1086)
<223> OTHER INFORMATION: n = a or g or c or t/u, unknown, or other.
<220> FEATURE:
<221> NAME/KEY: variation
<222> LOCATION: (1197)
<223> OTHER INFORMATION: n = a or g or c or t/u, unknown, or other.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 29 ggaggagat atg cag ttt gca ctt gca ttg gac acg aac tca ggt cct cac    51
          Met Gln Phe Ala Leu Ala Leu Asp Thr Asn Ser Gly Pro His
          1               5                   10
```

| | | | | | | | | | | | | | | | | |
|---|---|---|---|---|---|---|---|---|---|---|---|---|---|---|---|---|
| cag | ata | aga | tct | tgt | gag | ggt | gat | ggg | att | gac | agg | ttg | gaa | aaa | tta | 99 |
| Gln | Ile | Arg | Ser | Cys | Glu | Gly | Asp | Gly | Ile | Asp | Arg | Leu | Glu | Lys | Leu | |
| 15 | | | | 20 | | | | | 25 | | | | | 30 | | |
| agt | att | ggg | ggc | aga | aag | cag | gag | aaa | gct | ttg | aga | aat | agg | tgc | ttt | 147 |
| Ser | Ile | Gly | Gly | Arg | Lys | Gln | Glu | Lys | Ala | Leu | Arg | Asn | Arg | Cys | Phe | |
| | | | 35 | | | | | 40 | | | | | 45 | | | |
| ggt | ggt | aga | gtt | gct | gca | act | aca | caa | tgt | att | ctt | acc | tca | gat | gct | 195 |
| Gly | Gly | Arg | Val | Ala | Ala | Thr | Thr | Gln | Cys | Ile | Leu | Thr | Ser | Asp | Ala | |
| | | 50 | | | | | 55 | | | | | 60 | | | | |
| tgt | cct | gaa | act | ctt | cat | tct | caa | aca | cag | tcc | tct | agg | aaa | aat | tat | 243 |
| Cys | Pro | Glu | Thr | Leu | His | Ser | Gln | Thr | Gln | Ser | Ser | Arg | Lys | Asn | Tyr | |
| | 65 | | | | | 70 | | | | | 75 | | | | | |
| gct | gat | gca | aac | cgt | gta | tct | gck | atc | att | ttg | ggc | gga | ggc | act | gga | 291 |
| Ala | Asp | Ala | Asn | Arg | Val | Ser | Ala | Ile | Ile | Leu | Gly | Gly | Gly | Thr | Gly | |
| 80 | | | | | 85 | | | | | 90 | | | | | | |
| tct | cag | ctc | ttt | cct | ctg | aca | agc | aca | aga | gct | acg | cct | gct | gta | cct | 339 |
| Ser | Gln | Leu | Phe | Pro | Leu | Thr | Ser | Thr | Arg | Ala | Thr | Pro | Ala | Val | Pro | |
| 95 | | | | 100 | | | | | 105 | | | | | 110 | | |
| gtt | gga | gga | tgt | tac | agg | ctt | att | gat | atc | cct | atg | agt | aac | tgc | ttc | 387 |
| Val | Gly | Gly | Cys | Tyr | Arg | Leu | Ile | Asp | Ile | Pro | Met | Ser | Asn | Cys | Phe | |
| | | | | 115 | | | | | 120 | | | | | 125 | | |
| aac | agt | ggt | ata | aat | aag | ata | ttt | gtg | atg | agt | cag | ttc | aat | tct | act | 435 |
| Asn | Ser | Gly | Ile | Asn | Lys | Ile | Phe | Val | Met | Ser | Gln | Phe | Asn | Ser | Thr | |
| | | 130 | | | | | 135 | | | | | 140 | | | | |
| tcg | ctt | aac | cgc | cat | att | cat | cgt | aca | tac | ctt | gaa | ggc | ggg | atc | aac | 483 |
| Ser | Leu | Asn | Arg | His | Ile | His | Arg | Thr | Tyr | Leu | Glu | Gly | Gly | Ile | Asn | |
| | 145 | | | | | 150 | | | | | 155 | | | | | |
| ttt | gct | gat | gga | tct | gta | cag | gta | tta | gcg | gct | aca | caa | atg | cct | gaa | 531 |
| Phe | Ala | Asp | Gly | Ser | Val | Gln | Val | Leu | Ala | Ala | Thr | Gln | Met | Pro | Glu | |
| 160 | | | | | 165 | | | | | 170 | | | | | | |
| gag | cca | gct | gga | tgg | ttc | cag | ggt | aca | gca | gac | tct | atc | aga | aaa | ttt | 579 |
| Glu | Pro | Ala | Gly | Trp | Phe | Gln | Gly | Thr | Ala | Asp | Ser | Ile | Arg | Lys | Phe | |
| 175 | | | | 180 | | | | | 185 | | | | | 190 | | |
| atc | tgg | gta | ctc | gag | gat | tat | tac | agt | cac | aaa | tcc | att | gac | aac | att | 627 |
| Ile | Trp | Val | Leu | Glu | Asp | Tyr | Tyr | Ser | His | Lys | Ser | Ile | Asp | Asn | Ile | |
| | | | | 195 | | | | | 200 | | | | | 205 | | |
| gta | atc | ttg | agt | ggc | gat | cag | ctt | tat | cgg | atg | aat | tac | atg | gaa | ctt | 675 |
| Val | Ile | Leu | Ser | Gly | Asp | Gln | Leu | Tyr | Arg | Met | Asn | Tyr | Met | Glu | Leu | |
| | | 210 | | | | | 215 | | | | | 220 | | | | |
| gtg | cag | aaa | cat | gtc | gag | gac | gat | gct | gat | atc | act | ata | tca | tgt | gct | 723 |
| Val | Gln | Lys | His | Val | Glu | Asp | Asp | Ala | Asp | Ile | Thr | Ile | Ser | Cys | Ala | |
| | 225 | | | | | 230 | | | | | 235 | | | | | |
| cct | gtt | gat | gag | agc | cga | gct | tct | aaa | aat | ggg | cta | gtg | aag | att | gat | 771 |
| Pro | Val | Asp | Glu | Ser | Arg | Ala | Ser | Lys | Asn | Gly | Leu | Val | Lys | Ile | Asp | |
| 240 | | | | | 245 | | | | | 250 | | | | | | |
| cat | act | gga | cgt | gta | ctt | caa | ttc | ttt | gaa | aaa | cca | aag | ggt | gct | gat | 819 |
| His | Thr | Gly | Arg | Val | Leu | Gln | Phe | Phe | Glu | Lys | Pro | Lys | Gly | Ala | Asp | |
| 255 | | | | 260 | | | | | 265 | | | | | 270 | | |
| ttg | aat | tct | atg | aga | gtt | gag | acc | aac | ttc | ctg | agc | tat | gct | ata | gat | 867 |
| Leu | Asn | Ser | Met | Arg | Val | Glu | Thr | Asn | Phe | Leu | Ser | Tyr | Ala | Ile | Asp | |
| | | | 275 | | | | | 280 | | | | | 285 | | | |
| gat | gca | cag | aaa | tat | cca | tac | ctt | gca | tca | atg | ggc | att | tat | gtc | ttc | 915 |
| Asp | Ala | Gln | Lys | Tyr | Pro | Tyr | Leu | Ala | Ser | Met | Gly | Ile | Tyr | Val | Phe | |
| | | 290 | | | | | 295 | | | | | 300 | | | | |
| aag | aaa | gat | gca | ctt | tta | gac | ctt | ctc | aag | tca | aaa | tat | act | caa | tta | 963 |
| Lys | Lys | Asp | Ala | Leu | Leu | Asp | Leu | Leu | Lys | Ser | Lys | Tyr | Thr | Gln | Leu | |
| | 305 | | | | | 310 | | | | | 315 | | | | | |
| cat | gac | ttt | gga | tct | aar | atc | ctc | cca | aga | gct | gta | cta | gat | cay | agt | 1011 |
| His | Asp | Phe | Gly | Ser | Lys | Ile | Leu | Pro | Arg | Ala | Val | Leu | Asp | His | Ser | |
| 320 | | | | | 325 | | | | | 330 | | | | | | |

| | | | | | | | | | | | | | | | |
|---|---|---|---|---|---|---|---|---|---|---|---|---|---|---|---|
| gtg | cag | gca | tgc | att | ttt | acg | ggc | tat | tgg | gag | gat | gtt | gga | aca | atc | 1059
| Val | Gln | Ala | Cys | Ile | Phe | Thr | Gly | Tyr | Trp | Glu | Asp | Val | Gly | Thr | Ile |
| 335 | | | | | 340 | | | | | 345 | | | | | 350 |

```
gtg cag gca tgc att ttt acg ggc tat tgg gag gat gtt gga aca atc      1059
Val Gln Ala Cys Ile Phe Thr Gly Tyr Trp Glu Asp Val Gly Thr Ile
335                 340                 345                 350 aaa tca ttc ttt gat gca aac ttg gtn ctc act gag cag cct tcc aag      1107
Lys Ser Phe Phe Asp Ala Asn Leu Val Leu Thr Glu Gln Pro Ser Lys
            355                 360                 365 ttt gat ttt tac gat cca aaa aca cct ttc ttc act gca ccc cga tgc      1155
Phe Asp Phe Tyr Asp Pro Lys Thr Pro Phe Phe Thr Ala Pro Arg Cys
        370                 375                 380 ttg cct ccg acg caa ttg gac aag tgc aag atg aaa tat gtn ttt atc      1203
Leu Pro Pro Thr Gln Leu Asp Lys Cys Lys Met Lys Tyr Val Phe Ile
    385                 390                 395 tca gat ggt tgc tta ctg aga gaa tgc aac atc gag cat tct gtg att      1251
Ser Asp Gly Cys Leu Leu Arg Glu Cys Asn Ile Glu His Ser Val Ile
400                 405                 410 gga gtc tgc tca cgt gtc agc tct gga tgt gaa ctc aag gac tcc gtg      1299
Gly Val Cys Ser Arg Val Ser Ser Gly Cys Glu Leu Lys Asp Ser Val
415                 420                 425                 430 atg atg gga gcg gac atc tat gaa act gaa gaa gaa gct tca aag cta      1347
Met Met Gly Ala Asp Ile Tyr Glu Thr Glu Glu Glu Ala Ser Lys Leu
            435                 440                 445 ctg tta gct ggg aag gtc ccr gtt gga ata gga agg aac aca aag ata      1395
Leu Leu Ala Gly Lys Val Pro Val Gly Ile Gly Arg Asn Thr Lys Ile
        450                 455                 460 agg aac tgt atc att gac atg aat gct agg att ggg aag aac gtg gtg      1443
Arg Asn Cys Ile Ile Asp Met Asn Ala Arg Ile Gly Lys Asn Val Val
    465                 470                 475 atc aca aac agt aag ggc atc caa gag gct gat cac ccg gaa gaa ggg      1491
Ile Thr Asn Ser Lys Gly Ile Gln Glu Ala Asp His Pro Glu Glu Gly
480                 485                 490 tac tac ata agg tct gga atc gtg gtg atc ctg aag aat gca acc atc      1539
Tyr Tyr Ile Arg Ser Gly Ile Val Val Ile Leu Lys Asn Ala Thr Ile
495                 500                 505                 510 aac gat ggg tct gtc ata tagatcggct gcgtktgcg                         1576
Asn Asp Gly Ser Val Ile
            515
```

<210> SEQ ID NO 30
<211> LENGTH: 516
<212> TYPE: PRT
<213> ORGANISM: Zea mays

<400> SEQUENCE: 30

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125
```

Gly Ile Asn Lys Ile Phe Val Met Ser Gln Phe Asn Ser Thr Ser Leu
        130                 135                 140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
                180                 185                 190

Val Leu Glu Asp Tyr Tyr Ser His Lys Ser Ile Asp Asn Ile Val Ile
                195                 200                 205

Leu Ser Gly Asp Gln Leu Tyr Arg Met Asn Tyr Met Glu Leu Val Gln
        210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
                260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
        290                 295                 300

Asp Ala Leu Leu Asp Leu Leu Lys Ser Lys Tyr Thr Gln Leu His Asp
305                 310                 315                 320

Phe Gly Ser Lys Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
                340                 345                 350

Phe Phe Asp Ala Asn Leu Val Leu Thr Glu Gln Pro Ser Lys Phe Asp
        355                 360                 365

Phe Tyr Asp Pro Lys Thr Pro Phe Phe Thr Ala Pro Arg Cys Leu Pro
        370                 375                 380

Pro Thr Gln Leu Asp Lys Cys Lys Met Lys Tyr Val Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
                420                 425                 430

Gly Ala Asp Ile Tyr Glu Thr Glu Glu Ala Ser Lys Leu Leu Leu
        435                 440                 445

Ala Gly Lys Val Pro Val Gly Ile Gly Arg Asn Thr Lys Ile Arg Asn
        450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
                500                 505                 510

Gly Ser Val Ile
        515

<210> SEQ ID NO 31
<211> LENGTH: 1576
<212> TYPE: DNA

-continued

```
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 31 ggaggagat atg cag ttt gca ctt gca ttg gac acg aac tca ggt cct cac        51
          Met Gln Phe Ala Leu Ala Leu Asp Thr Asn Ser Gly Pro His
          1               5                   10 cag ata aga tct tgt gag ggt gat ggg att gac agg ttg gaa aaa tta          99
Gln Ile Arg Ser Cys Glu Gly Asp Gly Ile Asp Arg Leu Glu Lys Leu
15                  20                  25                  30 agt att ggg ggc aga aag cag gag aaa gct ttg aga aat agg tgc ttt         147
Ser Ile Gly Gly Arg Lys Gln Glu Lys Ala Leu Arg Asn Arg Cys Phe
                35                  40                  45 ggt ggt aga gtt gct gca act aca caa tgt att ctt acc tca gat gct         195
Gly Gly Arg Val Ala Ala Thr Thr Gln Cys Ile Leu Thr Ser Asp Ala
    50                  55                  60 tgt cct gaa act ctt cat tct caa aca cag tcc tct agg aaa aat tat         243
Cys Pro Glu Thr Leu His Ser Gln Thr Gln Ser Ser Arg Lys Asn Tyr
65                  70                  75 gct gat gca aac cgt gta tct gck atc att ttg ggc gga ggc act gga         291
Ala Asp Ala Asn Arg Val Ser Ala Ile Ile Leu Gly Gly Gly Thr Gly
        80                  85                  90 tct cag ctc ttt cct ctg aca agc aca aga gct acg cct gct gta cct         339
Ser Gln Leu Phe Pro Leu Thr Ser Thr Arg Ala Thr Pro Ala Val Pro
95                  100                 105                 110 gtt gga gga tgt tac agg ctt att gat atc cct atg agt aac tgc ttc         387
Val Gly Gly Cys Tyr Arg Leu Ile Asp Ile Pro Met Ser Asn Cys Phe
            115                 120                 125 aac agt ggt ata aat aag ata ttt gtg atg agt cag ttc aat tct act         435
Asn Ser Gly Ile Asn Lys Ile Phe Val Met Ser Gln Phe Asn Ser Thr
        130                 135                 140 tcg ctt aac cgc cat att cat cgt aca tac ctt gaa ggc ggg atc aac         483
Ser Leu Asn Arg His Ile His Arg Thr Tyr Leu Glu Gly Gly Ile Asn
    145                 150                 155 ttt gct gat gga tct gta cag gta tta gcg gct aca caa atg cct gaa         531
Phe Ala Asp Gly Ser Val Gln Val Leu Ala Ala Thr Gln Met Pro Glu
160                 165                 170 gag cca gct gga tgg ttc cag ggt aca gca gac tct atc aga aaa ttt         579
Glu Pro Ala Gly Trp Phe Gln Gly Thr Ala Asp Ser Ile Arg Lys Phe
175                 180                 185                 190 atc tgg gta ctc gag gat tat tac agt cac aaa tcc att gac aac att         627
Ile Trp Val Leu Glu Asp Tyr Tyr Ser His Lys Ser Ile Asp Asn Ile
                195                 200                 205 gta atc ttg agt ggc gat cag ctt tat cgg atg aat tac atg gaa ctt         675
Val Ile Leu Ser Gly Asp Gln Leu Tyr Arg Met Asn Tyr Met Glu Leu
        210                 215                 220
```

| | | | | | | | | | | | | | | | |
|---|---|---|---|---|---|---|---|---|---|---|---|---|---|---|---|
| gtg | cag | aaa | cat | gtc | gag | gac | gat | gct | gat | atc | act | ata | tca | tgt | gct |
| Val | Gln | Lys | His | Val | Glu | Asp | Asp | Ala | Asp | Ile | Thr | Ile | Ser | Cys | Ala |
| | 225 | | | | 230 | | | | 235 | | | | | | |

723 cct gtt gat gag agc cga gct tct aaa aat ggg cta gtg aag att gat    771
Pro Val Asp Glu Ser Arg Ala Ser Lys Asn Gly Leu Val Lys Ile Asp
    240             245                 250 cat act gga cgt gta ctt caa ttc ttt gaa aaa cca aag ggt gct gat    819
His Thr Gly Arg Val Leu Gln Phe Phe Glu Lys Pro Lys Gly Ala Asp
255             260                 265                 270 ttg aat tct atg aga gtt gag acc aac ttc ctg agc tat gct ata gat    867
Leu Asn Ser Met Arg Val Glu Thr Asn Phe Leu Ser Tyr Ala Ile Asp
            275                 280                 285 gat gca cag aaa tat cca tac ctt gca tca atg ggc att tat gtc ttc    915
Asp Ala Gln Lys Tyr Pro Tyr Leu Ala Ser Met Gly Ile Tyr Val Phe
        290                 295                 300 aag aaa gat gca ctt tta gac ctt ctc aag tca aaa tat act caa tta    963
Lys Lys Asp Ala Leu Leu Asp Leu Leu Lys Ser Lys Tyr Thr Gln Leu
    305                 310                 315 cat gac ttt gga tct gaa atc ctc cca aga gct gta cta gat tty agt    1011
His Asp Phe Gly Ser Glu Ile Leu Pro Arg Ala Val Leu Asp Phe Ser
320                 325                 330 gtg cag gca tgc att ttt acg ggc tat tgg gag gat gtt gga aca atc    1059
Val Gln Ala Cys Ile Phe Thr Gly Tyr Trp Glu Asp Val Gly Thr Ile
335             340                 345                 350 aaa tca ttc ttt gat gca aac ttg gcc ctc act gag cag cct tcc aag    1107
Lys Ser Phe Phe Asp Ala Asn Leu Ala Leu Thr Glu Gln Pro Ser Lys
            355                 360                 365 ttt gat ttt tac gat cca aaa aca cct ttc ttc act gca ccc cga tgc    1155
Phe Asp Phe Tyr Asp Pro Lys Thr Pro Phe Phe Thr Ala Pro Arg Cys
        370                 375                 380 ttg cct ccg acg caa ttg gac aag tgc aag atg aaa tat gca ttt atc    1203
Leu Pro Pro Thr Gln Leu Asp Lys Cys Lys Met Lys Tyr Ala Phe Ile
    385                 390                 395 tca gat ggt tgc tta ctg aga gaa tgc aac atc gag cat tct gtg att    1251
Ser Asp Gly Cys Leu Leu Arg Glu Cys Asn Ile Glu His Ser Val Ile
400                 405                 410 gga gtc tgc tca cgt gtc agc tct gga tgt gaa ctc aag gac tcc gtg    1299
Gly Val Cys Ser Arg Val Ser Ser Gly Cys Glu Leu Lys Asp Ser Val
415             420                 425                 430 atg atg gga gcg gac atc tat gaa act gaa gaa gaa gct tca aag cta    1347
Met Met Gly Ala Asp Ile Tyr Glu Thr Glu Glu Glu Ala Ser Lys Leu
            435                 440                 445 ctg tta gct ggg aag gtc ccr gtt gga ata gga agg aac aca aag ata    1395
Leu Leu Ala Gly Lys Val Pro Val Gly Ile Gly Arg Asn Thr Lys Ile
        450                 455                 460 agg aac tgt atc att gac atg aat gct agg att ggg aag aac gtg gtg    1443
Arg Asn Cys Ile Ile Asp Met Asn Ala Arg Ile Gly Lys Asn Val Val
    465                 470                 475 atc aca aac agt aag ggc atc caa gag gct gat cac ccg gaa gaa ggg    1491
Ile Thr Asn Ser Lys Gly Ile Gln Glu Ala Asp His Pro Glu Glu Gly
480                 485                 490 tac tac ata agg tct gga atc gtg gtg atc ctg aag aat gca acc atc    1539
Tyr Tyr Ile Arg Ser Gly Ile Val Val Ile Leu Lys Asn Ala Thr Ile
495             500                 505                 510 aac gat ggg tct gtc ata tagatcggct gcgtktgcg    1576
Asn Asp Gly Ser Val Ile
                515

<210> SEQ ID NO 32
<211> LENGTH: 516

-continued

```
<212> TYPE: PRT
<213> ORGANISM: Zea mays

<400> SEQUENCE: 32

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Phe Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400
```

```
Gly Cys Leu Leu Arg Glu Cys Asn Ile Glu His Ser Val Ile Gly Val
            405                 410                 415
Cys Ser Arg Val Ser Ser Gly Cys Glu Leu Lys Asp Ser Val Met Met
        420                 425                 430
Gly Ala Asp Ile Tyr Glu Thr Glu Glu Ala Ser Lys Leu Leu Leu
    435                 440                 445
Ala Gly Lys Val Pro Val Gly Ile Gly Arg Asn Thr Lys Ile Arg Asn
450                 455                 460
Cys Ile Ile Asp Met Asn Ala Arg Ile Gly Lys Asn Val Val Ile Thr
465                 470                 475                 480
Asn Ser Lys Gly Ile Gln Glu Ala Asp His Pro Glu Glu Gly Tyr Tyr
                485                 490                 495
Ile Arg Ser Gly Ile Val Val Ile Leu Lys Asn Ala Thr Ile Asn Asp
            500                 505                 510
Gly Ser Val Ile
        515

<210> SEQ ID NO 33
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 33 ggaggagat atg cag ttt gca ctt gca ttg gac acg aac tca ggt cct cac      51
          Met Gln Phe Ala Leu Ala Leu Asp Thr Asn Ser Gly Pro His
          1               5                   10 cag ata aga tct tgt gag ggt gat ggg att gac agg ttg gaa aaa tta        99
Gln Ile Arg Ser Cys Glu Gly Asp Gly Ile Asp Arg Leu Glu Lys Leu
 15              20                  25                  30 agt att ggg ggc aga aag cag gag aaa gct ttg aga aat agg tgc ttt       147
Ser Ile Gly Gly Arg Lys Gln Glu Lys Ala Leu Arg Asn Arg Cys Phe
             35                  40                  45 ggt ggt aga gtt gct gca act aca caa tgt att ctt acc tca gat gct       195
Gly Gly Arg Val Ala Ala Thr Thr Gln Cys Ile Leu Thr Ser Asp Ala
         50                  55                  60 tgt cct gaa act ctt cat tct caa aca cag tcc tct agg aaa aat tat       243
Cys Pro Glu Thr Leu His Ser Gln Thr Gln Ser Ser Arg Lys Asn Tyr
     65                  70                  75 gct gat gca aac cgt gta tct gck atc att ttg ggc gga ggc act gga       291
Ala Asp Ala Asn Arg Val Ser Ala Ile Ile Leu Gly Gly Gly Thr Gly
 80                  85                  90 tct cag ctc ttt cct ctg aca agc aca aga gct acg cct gct gta cct       339
Ser Gln Leu Phe Pro Leu Thr Ser Thr Arg Ala Thr Pro Ala Val Pro
 95                 100                 105                 110 gtt gga gga tgt tac agg ctt att gat atc cct atg agt aac tgc ttc       387
Val Gly Gly Cys Tyr Arg Leu Ile Asp Ile Pro Met Ser Asn Cys Phe
             115                 120                 125
```

-continued

| | |
|---|---|
| aac agt ggt ata aat aag ata ttt gtg atg agt cag ttc aat tct act<br>Asn Ser Gly Ile Asn Lys Ile Phe Val Met Ser Gln Phe Asn Ser Thr<br>                130                        135                        140 | 435 |
| tcg ctt aac cgc cat att cat cgt aca tac ctt gaa ggc ggg atc aac<br>Ser Leu Asn Arg His Ile His Arg Thr Tyr Leu Glu Gly Gly Ile Asn<br>            145                        150                        155 | 483 |
| ttt gct gat gga tct gta cag gta tta gcg gct aca caa atg cct gaa<br>Phe Ala Asp Gly Ser Val Gln Val Leu Ala Ala Thr Gln Met Pro Glu<br>160                        165                        170 | 531 |
| gag cca gct gga tgg ttc cag ggt aca gca gac tct atc aga aaa ttt<br>Glu Pro Ala Gly Trp Phe Gln Gly Thr Ala Asp Ser Ile Arg Lys Phe<br>175                        180                        185                        190 | 579 |
| atc tgg gta ctc gag gat tat tac agt cac aaa tcc att gac aac att<br>Ile Trp Val Leu Glu Asp Tyr Tyr Ser His Lys Ser Ile Asp Asn Ile<br>                        195                        200                        205 | 627 |
| gta atc ttg agt ggc gat cag ctt tat cgg atg aat tac atg gaa ctt<br>Val Ile Leu Ser Gly Asp Gln Leu Tyr Arg Met Asn Tyr Met Glu Leu<br>                    210                        215                        220 | 675 |
| gtg cag aaa cat gtc gag gac gat gct gat atc act ata tca tgt gct<br>Val Gln Lys His Val Glu Asp Asp Ala Asp Ile Thr Ile Ser Cys Ala<br>            225                        230                        235 | 723 |
| cct gtt gat gag agc cga gct tct aaa aat ggg cta gtg aag att gat<br>Pro Val Asp Glu Ser Arg Ala Ser Lys Asn Gly Leu Val Lys Ile Asp<br>240                        245                        250 | 771 |
| cat act gga cgt gta ctt caa ttc ttt gaa aaa cca aag ggt gct gat<br>His Thr Gly Arg Val Leu Gln Phe Phe Glu Lys Pro Lys Gly Ala Asp<br>255                        260                        265                        270 | 819 |
| ttg aat tct atg aga gtt gag acc aac ttc ctg agc tat gct ata gat<br>Leu Asn Ser Met Arg Val Glu Thr Asn Phe Leu Ser Tyr Ala Ile Asp<br>                    275                        280                        285 | 867 |
| gat gca cag aaa tat cca tac ctt gca tca atg ggc att tat gtc ttc<br>Asp Ala Gln Lys Tyr Pro Tyr Leu Ala Ser Met Gly Ile Tyr Val Phe<br>                        290                        295                        300 | 915 |
| aag aaa gat gca ctt tta gac ctt ctc aag tca aaa tat act caa tta<br>Lys Lys Asp Ala Leu Leu Asp Leu Leu Lys Ser Lys Tyr Thr Gln Leu<br>305                        310                        315 | 963 |
| cat gac ttt gga tct gaa atc ctc cca aga gct gta cta gat atg agt<br>His Asp Phe Gly Ser Glu Ile Leu Pro Arg Ala Val Leu Asp Met Ser<br>320                        325                        330 | 1011 |
| gtg cag gca tgc att ttt acg ggc tat tgg gag gat gtt gga aca atc<br>Val Gln Ala Cys Ile Phe Thr Gly Tyr Trp Glu Asp Val Gly Thr Ile<br>335                        340                        345                        350 | 1059 |
| aaa tca ttc ttt gat gca aac ttg gcc ctc act gag cag cct tcc aag<br>Lys Ser Phe Phe Asp Ala Asn Leu Ala Leu Thr Glu Gln Pro Ser Lys<br>                    355                        360                        365 | 1107 |
| ttt gat ttt tac gat cca aaa aca cct ttc ttc act gca ccc cga tgc<br>Phe Asp Phe Tyr Asp Pro Lys Thr Pro Phe Phe Thr Ala Pro Arg Cys<br>                        370                        375                        380 | 1155 |
| ttg cct ccg acg caa ttg gac aag tgc aag atg aaa tat gca ttt atc<br>Leu Pro Pro Thr Gln Leu Asp Lys Cys Lys Met Lys Tyr Ala Phe Ile<br>385                        390                        395 | 1203 |
| tca gat ggt tgc tta ctg aga gaa tgc aac atc gag cat tct gtg att<br>Ser Asp Gly Cys Leu Leu Arg Glu Cys Asn Ile Glu His Ser Val Ile<br>400                        405                        410 | 1251 |
| gga gtc tgc tca cgt gtc agc tct gga tgt gaa ctc aag gac tcc gtg<br>Gly Val Cys Ser Arg Val Ser Ser Gly Cys Glu Leu Lys Asp Ser Val<br>415                        420                        425                        430 | 1299 |
| atg atg gga gcg gac atc tat gaa act gaa gaa gaa gct tca aag cta<br>Met Met Gly Ala Asp Ile Tyr Glu Thr Glu Glu Glu Ala Ser Lys Leu<br>                    435                        440                        445 | 1347 |

```
ctg tta gct ggg aag gtc ccr gtt gga ata gga agg aac aca aag ata      1395
Leu Leu Ala Gly Lys Val Pro Val Gly Ile Gly Arg Asn Thr Lys Ile
        450                 455                 460 agg aac tgt atc att gac atg aat gct agg att ggg aag aac gtg gtg      1443
Arg Asn Cys Ile Ile Asp Met Asn Ala Arg Ile Gly Lys Asn Val Val
            465                 470                 475 atc aca aac agt aag ggc atc caa gag gct gat cac ccg gaa gaa ggg      1491
Ile Thr Asn Ser Lys Gly Ile Gln Glu Ala Asp His Pro Glu Glu Gly
480                 485                 490 tac tac ata agg tct gga atc gtg gtg atc ctg aag aat gca acc atc      1539
Tyr Tyr Ile Arg Ser Gly Ile Val Val Ile Leu Lys Asn Ala Thr Ile
495                 500                 505                 510 aac gat ggg tct gtc ata tagatcggct gcgtktgcg                         1576
Asn Asp Gly Ser Val Ile
                515

<210> SEQ ID NO 34
<211> LENGTH: 516
<212> TYPE: PRT
<213> ORGANISM: Zea mays

<400> SEQUENCE: 34

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
            85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270
```

```
Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Met Ser Val Gln
                325                 330                 335

Ala Cys Ile Phe Thr Gly Tyr Trp Glu Asp Val Gly Thr Ile Lys Ser
                340                 345                 350

Phe Phe Asp Ala Asn Leu Ala Leu Thr Glu Gln Pro Ser Lys Phe Asp
                355                 360                 365

Phe Tyr Asp Pro Lys Thr Pro Phe Phe Thr Ala Pro Arg Cys Leu Pro
370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                    405                 410                 415

Cys Ser Arg Val Ser Ser Gly Cys Glu Leu Lys Asp Ser Val Met Met
                420                 425                 430

Gly Ala Asp Ile Tyr Glu Thr Glu Glu Glu Ala Ser Lys Leu Leu Leu
            435                 440                 445

Ala Gly Lys Val Pro Val Gly Ile Gly Arg Asn Thr Lys Ile Arg Asn
        450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                    485                 490                 495

Ile Arg Ser Gly Ile Val Val Ile Leu Lys Asn Ala Thr Ile Asn Asp
                500                 505                 510

Gly Ser Val Ile
        515

<210> SEQ ID NO 35
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (540)
<223> OTHER INFORMATION: n = a or g or c or t/u, unknown, or other.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 35
```

```
ggaggagat atg cag ttt gca ctt gca ttg gac acg aac tca ggt cct cac      51
         Met Gln Phe Ala Leu Ala Leu Asp Thr Asn Ser Gly Pro His
          1               5                  10 cag ata aga tct tgt gag ggt gat ggg att gac agg ttg gaa aaa tta        99
Gln Ile Arg Ser Cys Glu Gly Asp Gly Ile Asp Arg Leu Glu Lys Leu
 15              20                  25                  30 agt att ggg ggc aga aag cag gag aaa gct ttg aga aat agg tgc ttt       147
Ser Ile Gly Gly Arg Lys Gln Glu Lys Ala Leu Arg Asn Arg Cys Phe
             35                  40                  45 ggt gga aga gtt gct gca act aca caa tgt att ctt acc tca gat gct       195
Gly Gly Arg Val Ala Ala Thr Thr Gln Cys Ile Leu Thr Ser Asp Ala
         50                  55                  60 tgt cct gaa act ctt cat tct caa aca cag tcc tct agg aaa aat tat       243
Cys Pro Glu Thr Leu His Ser Gln Thr Gln Ser Ser Arg Lys Asn Tyr
     65                  70                  75 gct gat gca aac cgt gta tct gck atc att ttg ggc gga ggc act gga       291
Ala Asp Ala Asn Arg Val Ser Ala Ile Ile Leu Gly Gly Gly Thr Gly
 80                  85                  90 tct cag ctc ttt cct ctg aca agc aca aga gct acg cct gct gta cct       339
Ser Gln Leu Phe Pro Leu Thr Ser Thr Arg Ala Thr Pro Ala Val Pro
 95             100                 105                 110 gtt gga gga tgt tac agg ctt att gat atc cct atg agt aac tgc ttc       387
Val Gly Gly Cys Tyr Arg Leu Ile Asp Ile Pro Met Ser Asn Cys Phe
            115                 120                 125 aac agt ggt ata aat aag ata ttt gtg atg agt cag ttc aat tct act       435
Asn Ser Gly Ile Asn Lys Ile Phe Val Met Ser Gln Phe Asn Ser Thr
        130                 135                 140 tcg ctt aac cgc cat att cat cgt aca tac ctt gaa ggc ggg atc aac       483
Ser Leu Asn Arg His Ile His Arg Thr Tyr Leu Glu Gly Gly Ile Asn
        145                 150                 155 ttt gct gat gga tct gta cag gta tta gcg gct aca caa atg cct gaa       531
Phe Ala Asp Gly Ser Val Gln Val Leu Ala Ala Thr Gln Met Pro Glu
160                 165                 170 gag cca gtn gga tgg ttc cag ggt aca gca gac tct atc aga aaa ttt       579
Glu Pro Val Gly Trp Phe Gln Gly Thr Ala Asp Ser Ile Arg Lys Phe
175                 180                 185                 190 atc tgg gta ctc gag gat tat tac agt cac aaa tcc att gac aac att       627
Ile Trp Val Leu Glu Asp Tyr Tyr Ser His Lys Ser Ile Asp Asn Ile
                195                 200                 205 gta atc ttg agt ggc gat cag ctt tat cgg atg aat tac atg gaa ctt       675
Val Ile Leu Ser Gly Asp Gln Leu Tyr Arg Met Asn Tyr Met Glu Leu
            210                 215                 220 gtg cag aaa cat gtc gag gac gat gct gat atc act ata tca tgt gct       723
Val Gln Lys His Val Glu Asp Asp Ala Asp Ile Thr Ile Ser Cys Ala
        225                 230                 235 cct gtt gat gag agc cga gct tct aaa aat ggg cta gtg aag att gat       771
Pro Val Asp Glu Ser Arg Ala Ser Lys Asn Gly Leu Val Lys Ile Asp
240                 245                 250 cat act gga cgt gta ctt caa ttc ttt gaa aaa cca aag ggt gct gat       819
His Thr Gly Arg Val Leu Gln Phe Phe Glu Lys Pro Lys Gly Ala Asp
255                 260                 265                 270 ttg aat tct atg aga gtt gag acc aac ttc ctg agc tat gct ata gat       867
Leu Asn Ser Met Arg Val Glu Thr Asn Phe Leu Ser Tyr Ala Ile Asp
                275                 280                 285 gat gca cag aaa tat cca tac ctt gca tca atg ggc att tat gtc ttc       915
Asp Ala Gln Lys Tyr Pro Tyr Leu Ala Ser Met Gly Ile Tyr Val Phe
            290                 295                 300 aag aaa gat gca ctt tta gac ctt ctc aag tca aaa tat act caa tta       963
Lys Lys Asp Ala Leu Leu Asp Leu Leu Lys Ser Lys Tyr Thr Gln Leu
        305                 310                 315
```

| | | |
|---|---|---|
| cat gac ttt gga tct gaa atc ctc cca aga gct gta cta gat tay agt<br>His Asp Phe Gly Ser Glu Ile Leu Pro Arg Ala Val Leu Asp Tyr Ser<br>320                           325                   330 | | 1011 |
| gtg cag gca tgc att ttt acg ggc tat tgg gag gat gtt gga aca atc<br>Val Gln Ala Cys Ile Phe Thr Gly Tyr Trp Glu Asp Val Gly Thr Ile<br>335                       340                   345               350 | | 1059 |
| aaa tca ttc ttt gat gca aac ttg gcc ctc act gag cag cct tcc aag<br>Lys Ser Phe Phe Asp Ala Asn Leu Ala Leu Thr Glu Gln Pro Ser Lys<br>                   355                   360                   365 | | 1107 |
| ttt gat ttt tac gat cca aaa aca cct ttc ttc act gca ccc cga tgc<br>Phe Asp Phe Tyr Asp Pro Lys Thr Pro Phe Phe Thr Ala Pro Arg Cys<br>                   370                   375                   380 | | 1155 |
| ttg cct ccg acg caa ttg gac aag tgc aag atg aaa tat gca ttt atc<br>Leu Pro Pro Thr Gln Leu Asp Lys Cys Lys Met Lys Tyr Ala Phe Ile<br>385                           390                   395 | | 1203 |
| tca gat ggt tgc tta ctg aga gaa tgc aac atc gag cat tct gtg att<br>Ser Asp Gly Cys Leu Leu Arg Glu Cys Asn Ile Glu His Ser Val Ile<br>400                           405                   410 | | 1251 |
| gga gtc tgc tca cgt gtc agc tct gga tgt gaa ctc aag gac tcc gtg<br>Gly Val Cys Ser Arg Val Ser Ser Gly Cys Glu Leu Lys Asp Ser Val<br>415                           420                   425               430 | | 1299 |
| atg atg gga gcg gac atc tat gaa act gaa gaa gaa gct tca aag cta<br>Met Met Gly Ala Asp Ile Tyr Glu Thr Glu Glu Glu Ala Ser Lys Leu<br>                   435                   440                   445 | | 1347 |
| ctg tta gct ggg aag gtc ccr gtt gga ata gga agg aac aca aag ata<br>Leu Leu Ala Gly Lys Val Pro Val Gly Ile Gly Arg Asn Thr Lys Ile<br>                   450                   455                   460 | | 1395 |
| agg aac tgt atc att gac atg aat gct agg att ggg aag aac gtg gtg<br>Arg Asn Cys Ile Ile Asp Met Asn Ala Arg Ile Gly Lys Asn Val Val<br>465                           470                   475 | | 1443 |
| atc aca aac agt aag ggc atc caa gag gct gat cac ccg gaa gaa ggg<br>Ile Thr Asn Ser Lys Gly Ile Gln Glu Ala Asp His Pro Glu Glu Gly<br>480                           485                   490 | | 1491 |
| tac tac ata agg tct gga atc gtg gtg atc ctg aag aat gca acc atc<br>Tyr Tyr Ile Arg Ser Gly Ile Val Val Ile Leu Lys Asn Ala Thr Ile<br>495                           500                   505               510 | | 1539 |
| aac gat ggg tct gtc ata tagatcggct gcgtktgcg<br>Asn Asp Gly Ser Val Ile<br>                   515 | | 1576 |

<210> SEQ ID NO 36
<211> LENGTH: 516
<212> TYPE: PRT
<213> ORGANISM: Zea mays

<400> SEQUENCE: 36

Met Gln Phe Ala Leu Ala Leu Asp Thr Asn Ser Gly Pro His Gln Ile
1                 5                   10                   15

Arg Ser Cys Glu Gly Asp Gly Ile Asp Arg Leu Glu Lys Leu Ser Ile
                   20                   25                   30

Gly Gly Arg Lys Gln Glu Lys Ala Leu Arg Asn Arg Cys Phe Gly Gly
                35                   40                   45

Arg Val Ala Ala Thr Thr Gln Cys Ile Leu Thr Ser Asp Ala Cys Pro
 50                   55                   60

Glu Thr Leu His Ser Gln Thr Gln Ser Ser Arg Lys Asn Tyr Ala Asp
65                 70                   75                   80

Ala Asn Arg Val Ser Ala Ile Ile Leu Gly Gly Thr Gly Ser Gln
                85                   90                   95

Leu Phe Pro Leu Thr Ser Thr Arg Ala Thr Pro Ala Val Pro Val Gly

```
                    100                 105                 110
Gly Cys Tyr Arg Leu Ile Asp Ile Pro Met Ser Asn Cys Phe Asn Ser
            115                 120                 125

Gly Ile Asn Lys Ile Phe Val Met Ser Gln Phe Asn Ser Thr Ser Leu
        130                 135                 140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Val Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Tyr Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
            420                 425                 430

Gly Ala Asp Ile Tyr Glu Thr Glu Glu Ala Ser Lys Leu Leu Leu
        435                 440                 445

Ala Gly Lys Val Pro Val Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515
```

<210> SEQ ID NO 37
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1197)
<223> OTHER INFORMATION: n = a or g or c or t/u, unknown, or other.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 37

```
ggaggagat atg cag ttt gca ctt gca ttg gac acg aac tca ggt cct cac        51
          Met Gln Phe Ala Leu Ala Leu Asp Thr Asn Ser Gly Pro His
          1               5                   10 cag ata aga tct tgt gag ggt gat ggg att gac agg ttg gaa aaa tta          99
Gln Ile Arg Ser Cys Glu Gly Asp Gly Ile Asp Arg Leu Glu Lys Leu
15                  20                  25                  30 agt att ggg ggc aga aag cag gag aaa gct ttg aga aat agg tgc ttt         147
Ser Ile Gly Gly Arg Lys Gln Glu Lys Ala Leu Arg Asn Arg Cys Phe
                35                  40                  45 ggt ggt aga gtt gct gca act aca caa tgt att ctt acc tca gat gct         195
Gly Gly Arg Val Ala Ala Thr Thr Gln Cys Ile Leu Thr Ser Asp Ala
    50                  55                  60 tgt cct gaa act ctt cat tct caa aca cag tcc tct agg aaa aat tat         243
Cys Pro Glu Thr Leu His Ser Gln Thr Gln Ser Ser Arg Lys Asn Tyr
65                  70                  75 gct gat gca aac cgt gta tct gck atc att ttg ggc gga ggc act gga         291
Ala Asp Ala Asn Arg Val Ser Ala Ile Ile Leu Gly Gly Gly Thr Gly
                80                  85                  90 tct cag ctc ttt cct ctg aca agc aca aga gct acg cct gct gta cct         339
Ser Gln Leu Phe Pro Leu Thr Ser Thr Arg Ala Thr Pro Ala Val Pro
95                  100                 105                 110 gtt gga gga tgt tac agg ctt att gat atc cct atg agt aac tgc ttc         387
Val Gly Gly Cys Tyr Arg Leu Ile Asp Ile Pro Met Ser Asn Cys Phe
                115                 120                 125 aac agt ggt ata aat aag ata ttt gtg atg agt cag ttc aat tct act         435
Asn Ser Gly Ile Asn Lys Ile Phe Val Met Ser Gln Phe Asn Ser Thr
            130                 135                 140 tcg ctt aac cgc cat att cat cgt aca tac ctt gaa ggc ggg atc aac         483
Ser Leu Asn Arg His Ile His Arg Thr Tyr Leu Glu Gly Gly Ile Asn
145                 150                 155 ttt gct gat gga tct gta cag gta tta gcg gct aca caa atg cct gaa         531
Phe Ala Asp Gly Ser Val Gln Val Leu Ala Ala Thr Gln Met Pro Glu
                160                 165                 170 gag cca gct gga tgg ttc cag ggt aca gca gac tct atc aga aaa ttt         579
Glu Pro Ala Gly Trp Phe Gln Gly Thr Ala Asp Ser Ile Arg Lys Phe
175                 180                 185                 190
```

| | | | | | | | | | | | | | | | |
|---|---|---|---|---|---|---|---|---|---|---|---|---|---|---|---|
| atc | tgg | gta | ctc | gag | gat | tat | tac | agt | cac | aaa | tcc | att | gac | aac | att | 627 |
| Ile | Trp | Val | Leu | Glu | Asp | Tyr | Tyr | Ser | His | Lys | Ser | Ile | Asp | Asn | Ile |
| | | | 195 | | | | | 200 | | | | | 205 | | | gta atc ttg agt ggc gat cag ctt tat cgg atg aat tac atg gaa ctt    675
Val Ile Leu Ser Gly Asp Gln Leu Tyr Arg Met Asn Tyr Met Glu Leu
        210                 215                 220 gtg cag aaa cat gtc gag gac gat gct gat atc act ata tca tgt gct    723
Val Gln Lys His Val Glu Asp Asp Ala Asp Ile Thr Ile Ser Cys Ala
            225                 230                 235 cct gtt gat gag agc cga gct tct aaa aat ggg cta gtg aag att gat    771
Pro Val Asp Glu Ser Arg Ala Ser Lys Asn Gly Leu Val Lys Ile Asp
        240                 245                 250 cat act gga cgt gta ctt caa ttc ttt gaa aaa cca aag ggt gct gat    819
His Thr Gly Arg Val Leu Gln Phe Phe Glu Lys Pro Lys Gly Ala Asp
255                 260                 265                 270 ttg aat tct atg aga gtt gag acc aac ttc ctg agc tat gct ata gat    867
Leu Asn Ser Met Arg Val Glu Thr Asn Phe Leu Ser Tyr Ala Ile Asp
            275                 280                 285 gat gca cag aaa tat cca tac ctt gca tca atg ggc att tat gtc ttc    915
Asp Ala Gln Lys Tyr Pro Tyr Leu Ala Ser Met Gly Ile Tyr Val Phe
        290                 295                 300 aag aaa gat gca ctt tta gac ctt ctc aag tca aaa tat act caa tta    963
Lys Lys Asp Ala Leu Leu Asp Leu Leu Lys Ser Lys Tyr Thr Gln Leu
305                 310                 315 cat gac ttt gga tct gaa atc ctc cca aga gct gta cta gat tay agt   1011
His Asp Phe Gly Ser Glu Ile Leu Pro Arg Ala Val Leu Asp Tyr Ser
        320                 325                 330 gtg cag gca tgc att ttt acg ggc tat tgg gag gat gtt gga aca atc   1059
Val Gln Ala Cys Ile Phe Thr Gly Tyr Trp Glu Asp Val Gly Thr Ile
335                 340                 345                 350 aaa tca ttc ttt gat gca aac ttg gcc ctc act gag cag cct tcc aag   1107
Lys Ser Phe Phe Asp Ala Asn Leu Ala Leu Thr Glu Gln Pro Ser Lys
            355                 360                 365 ttt gat ttt tac gat cca aaa aca cct ttc ttc act gca ccc cga tgc   1155
Phe Asp Phe Tyr Asp Pro Lys Thr Pro Phe Phe Thr Ala Pro Arg Cys
        370                 375                 380 ttg cct ccg acg caa ttg gac aag tgc aag atg aaa tat gtn ttt atc   1203
Leu Pro Pro Thr Gln Leu Asp Lys Cys Lys Met Lys Tyr Val Phe Ile
385                 390                 395 tca gat ggt tgc tta ctg aga gaa tgc aac atc gag cat tct gtg att   1251
Ser Asp Gly Cys Leu Leu Arg Glu Cys Asn Ile Glu His Ser Val Ile
400                 405                 410 gga gtc tgc tca cgt gtc agc tct gga tgt gaa ctc aag gac tcc gtg   1299
Gly Val Cys Ser Arg Val Ser Ser Gly Cys Glu Leu Lys Asp Ser Val
415                 420                 425                 430 atg atg gga gcg gac atc tat gaa act gaa gaa gaa gct tca aag cta   1347
Met Met Gly Ala Asp Ile Tyr Glu Thr Glu Glu Glu Ala Ser Lys Leu
            435                 440                 445 ctg tta gct ggg aag gtc ccr gtt gga ata gga agg aac aca aag ata   1395
Leu Leu Ala Gly Lys Val Pro Val Gly Ile Gly Arg Asn Thr Lys Ile
        450                 455                 460 agg aac tgt atc att gac atg aat gct agg att ggg aag aac gtg gtg   1443
Arg Asn Cys Ile Ile Asp Met Asn Ala Arg Ile Gly Lys Asn Val Val
465                 470                 475 atc aca aac agt aag ggc atc caa gag gct gat cac ccg gaa gaa ggg   1491
Ile Thr Asn Ser Lys Gly Ile Gln Glu Ala Asp His Pro Glu Glu Gly
            480                 485                 490 tac tac ata agg tct gga atc gtg gtg atc ctg aag aat gca acc atc   1539
Tyr Tyr Ile Arg Ser Gly Ile Val Val Ile Leu Lys Asn Ala Thr Ile
495                 500                 505                 510

```
aac gat ggg tct gtc ata tagatcggct gcgtktgcg              1576
Asn Asp Gly Ser Val Ile
            515

<210> SEQ ID NO 38
<211> LENGTH: 516
<212> TYPE: PRT
<213> ORGANISM: Zea mays

<400> SEQUENCE: 38

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65              70                  75                  80

Ala Asn Arg Val Ser Ala Ile Ile Leu Gly Gly Thr Gly Ser Gln
            85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
            165                 170                 175

Ala Gly Trp Phe Gln Gly Thr Ala Asp Ser Ile Arg Lys Phe Ile Trp
        180                 185                 190

Val Leu Glu Asp Tyr Tyr Ser His Lys Ser Ile Asp Asn Ile Val Ile
    195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
            245                 250                 255

Gly Arg Val Leu Gln Phe Phe Glu Lys Pro Lys Gly Ala Asp Leu Asn
        260                 265                 270

Ser Met Arg Val Glu Thr Asn Phe Leu Ser Tyr Ala Ile Asp Asp Ala
    275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Tyr Ser Val Gln
            325                 330                 335

Ala Cys Ile Phe Thr Gly Tyr Trp Glu Asp Val Gly Thr Ile Lys Ser
        340                 345                 350

Phe Phe Asp Ala Asn Leu Ala Leu Thr Glu Gln Pro Ser Lys Phe Asp
```

```
                355                 360                 365
Phe Tyr Asp Pro Lys Thr Pro Phe Phe Thr Ala Pro Arg Cys Leu Pro
        370                 375                 380

Pro Thr Gln Leu Asp Lys Cys Lys Met Lys Tyr Val Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
            420                 425                 430

Gly Ala Asp Ile Tyr Glu Thr Glu Glu Ala Ser Lys Leu Leu Leu
        435                 440                 445

Ala Gly Lys Val Pro Val Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515

<210> SEQ ID NO 39
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
<222> LOCATION: (267)
<223> OTHER INFORMATION: k = g or t; amino acid 86 = Ala.
<220> FEATURE:
<221> NAME/KEY: variation
<222> LOCATION: (540)
<223> OTHER INFORMATION: n = a or g or c or t/u, unknown, or other.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1197)
<223> OTHER INFORMATION: n = a or g or c or t/u, unknown, or other.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 39 ggaggagat atg cag ttt gca ctt gca ttg gac acg aac tca ggt cct cac    51
          Met Gln Phe Ala Leu Ala Leu Asp Thr Asn Ser Gly Pro His
            1               5                   10 cag ata aga tct tgt gag ggt gat ggg att gac agg ttg gaa aaa tta    99
Gln Ile Arg Ser Cys Glu Gly Asp Gly Ile Asp Arg Leu Glu Lys Leu
 15                  20                  25                  30 agt att ggg ggc aga aag cag gag aaa gct ttg aga aat agg tgc ttt   147
Ser Ile Gly Gly Arg Lys Gln Glu Lys Ala Leu Arg Asn Arg Cys Phe
             35                  40                  45
```

-continued

| | | |
|---|---|---|
| ggt ggt aga gtt gct gca act aca caa tgt att ctt acc tca gat gct<br>Gly Gly Arg Val Ala Ala Thr Thr Gln Cys Ile Leu Thr Ser Asp Ala<br>          50                   55                   60 | 195 |
| tgt cct gaa act ctt cat tct caa aca cag tcc tct agg aaa aat tat<br>Cys Pro Glu Thr Leu His Ser Gln Thr Gln Ser Ser Arg Lys Asn Tyr<br>    65                  70                   75 | 243 |
| gct gat gca aac cgt gta tct gck atc att ttg ggc gga ggc act gga<br>Ala Asp Ala Asn Arg Val Ser Ala Ile Ile Leu Gly Gly Gly Thr Gly<br>      80                  85                 90 | 291 |
| tct cag ctc ttt cct ctg aca agc aca aga gct acg cct gct gta cct<br>Ser Gln Leu Phe Pro Leu Thr Ser Thr Arg Ala Thr Pro Ala Val Pro<br>95                 100               105            110 | 339 |
| gtt gga gga tgt tac agg ctt att gat atc cct atg agt aac tgc ttc<br>Val Gly Gly Cys Tyr Arg Leu Ile Asp Ile Pro Met Ser Asn Cys Phe<br>               115              120            125 | 387 |
| aac agt ggt ata aat aag ata ttt gtg atg agt cag ttc aat tct act<br>Asn Ser Gly Ile Asn Lys Ile Phe Val Met Ser Gln Phe Asn Ser Thr<br>        130               135              140 | 435 |
| tcg ctt aac cgc cat att cat cgt aca tac ctt gaa ggc ggg atc aac<br>Ser Leu Asn Arg His Ile His Arg Thr Tyr Leu Glu Gly Gly Ile Asn<br>145                 150              155 | 483 |
| ttt gct gat gga tct gta cag gta tta gcg gct aca caa atg cct gaa<br>Phe Ala Asp Gly Ser Val Gln Val Leu Ala Ala Thr Gln Met Pro Glu<br>160                 165              170 | 531 |
| gag cca gtn gga tgg ttc cag ggt aca gca gac tct atc aga aaa ttt<br>Glu Pro Val Gly Trp Phe Gln Gly Thr Ala Asp Ser Ile Arg Lys Phe<br>175                 180              185            190 | 579 |
| atc tgg gta ctc gag gat tat tac agt cac aaa tcc att gac aac att<br>Ile Trp Val Leu Glu Asp Tyr Tyr Ser His Lys Ser Ile Asp Asn Ile<br>               195              200            205 | 627 |
| gta atc ttg agt ggc gat cag ctt tat cgg atg aat tac atg gaa ctt<br>Val Ile Leu Ser Gly Asp Gln Leu Tyr Arg Met Asn Tyr Met Glu Leu<br>        210               215              220 | 675 |
| gtg cag aaa cat gtc gag gac gat gct gat atc act ata tca tgt gct<br>Val Gln Lys His Val Glu Asp Asp Ala Asp Ile Thr Ile Ser Cys Ala<br>           225              230            235 | 723 |
| cct gtt gat gag agc cga gct tct aaa aat ggg cta gtg aag att gat<br>Pro Val Asp Glu Ser Arg Ala Ser Lys Asn Gly Leu Val Lys Ile Asp<br>240                 245              250 | 771 |
| cat act gga cgt gta ctt caa ttc ttt gaa aaa cca aag ggt gct gat<br>His Thr Gly Arg Val Leu Gln Phe Phe Glu Lys Pro Lys Gly Ala Asp<br>255                 260              265            270 | 819 |
| ttg aat tct atg aga gtt gag acc aac ttc ctg agc tat gct ata gat<br>Leu Asn Ser Met Arg Val Glu Thr Asn Phe Leu Ser Tyr Ala Ile Asp<br>           275              280            285 | 867 |
| gat gca cag aaa tat cca tac ctt gca tca atg ggc att tat gtc ttc<br>Asp Ala Gln Lys Tyr Pro Tyr Leu Ala Ser Met Gly Ile Tyr Val Phe<br>290                 295              300 | 915 |
| aag aaa gat gca ctt tta gac ctt ctc aag tca aaa tat act caa tta<br>Lys Lys Asp Ala Leu Leu Asp Leu Leu Lys Ser Lys Tyr Thr Gln Leu<br>           305              310            315 | 963 |
| cat gac ttt gga tct gaa atc ctc cca aga gct gta cta gat cay agt<br>His Asp Phe Gly Ser Glu Ile Leu Pro Arg Ala Val Leu Asp His Ser<br>320                 325              330 | 1011 |
| gtg cag gca tgc att ttt acg ggc tat tgg gag gat gtt gga aca atc<br>Val Gln Ala Cys Ile Phe Thr Gly Tyr Trp Glu Asp Val Gly Thr Ile<br>335                 340              345            350 | 1059 |
| aaa tca ttc ttt gat gca aac ttg gcc ctc act gag cag cct tcc aag<br>Lys Ser Phe Phe Asp Ala Asn Leu Ala Leu Thr Glu Gln Pro Ser Lys<br>           355              360            365 | 1107 |

| | | | | | | | | | | | | | | | |
|---|---|---|---|---|---|---|---|---|---|---|---|---|---|---|---|
| ttt | gat | ttt | tac | gat | cca | aaa | aca | cct | ttc | ttc | act | gca | ccc | cga | tgc | 1155
| Phe | Asp | Phe | Tyr | Asp | Pro | Lys | Thr | Pro | Phe | Phe | Thr | Ala | Pro | Arg | Cys |
| | | | 370 | | | | 375 | | | | | 380 | | | |

```
ttt gat ttt tac gat cca aaa aca cct ttc ttc act gca ccc cga tgc     1155
Phe Asp Phe Tyr Asp Pro Lys Thr Pro Phe Phe Thr Ala Pro Arg Cys
            370             375             380 ttg cct ccg acg caa ttg gac aag tgc aag atg aaa tat gtn ttt atc     1203
Leu Pro Pro Thr Gln Leu Asp Lys Cys Lys Met Lys Tyr Val Phe Ile
            385             390             395 tca gat ggt tgc tta ctg aga gaa tgc aac atc gag cat tct gtg att     1251
Ser Asp Gly Cys Leu Leu Arg Glu Cys Asn Ile Glu His Ser Val Ile
        400             405             410 gga gtc tgc tca cgt gtc agc tct ggt tgt gaa ctc aag gac tcc gtg     1299
Gly Val Cys Ser Arg Val Ser Ser Gly Cys Glu Leu Lys Asp Ser Val
415             420             425             430 atg atg gga gcg gac atc tat gaa act gaa gaa gaa gct tca aag cta     1347
Met Met Gly Ala Asp Ile Tyr Glu Thr Glu Glu Glu Ala Ser Lys Leu
                435             440             445 ctg tta gct ggg aag gtc ccr gtt gga ata gga agg aac aca aag ata     1395
Leu Leu Ala Gly Lys Val Pro Val Gly Ile Gly Arg Asn Thr Lys Ile
            450             455             460 agg aac tgt atc att gac atg aat gct agg att ggg aag aac gtg gtg     1443
Arg Asn Cys Ile Ile Asp Met Asn Ala Arg Ile Gly Lys Asn Val Val
            465             470             475 atc aca aac agt aag ggc atc caa gag gct gat cac ccg gaa gaa ggg     1491
Ile Thr Asn Ser Lys Gly Ile Gln Glu Ala Asp His Pro Glu Glu Gly
480             485             490 tac tac ata agg tct gga atc gtg gtg atc ctg aag aat gca acc atc     1539
Tyr Tyr Ile Arg Ser Gly Ile Val Val Ile Leu Lys Asn Ala Thr Ile
495             500             505             510 aac gat ggg tct gtc ata tagatcggct gcgtktgcg                         1576
Asn Asp Gly Ser Val Ile
                515
```

<210> SEQ ID NO 40
<211> LENGTH: 516
<212> TYPE: PRT
<213> ORGANISM: Zea mays

<400> SEQUENCE: 40

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
```

```
                165                 170                 175
Val Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Val Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
            420                 425                 430

Gly Ala Asp Ile Tyr Glu Thr Glu Glu Ala Ser Lys Leu Leu Leu
        435                 440                 445

Ala Gly Lys Val Pro Val Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515

<210> SEQ ID NO 41
<211> LENGTH: 1576
<212> TYPE: DNA
<213> ORGANISM: Zea mays
<220> FEATURE:
<221> NAME/KEY: CDS
<222> LOCATION: (10)..(1563)
<223> OTHER INFORMATION: Shrunken-2 gene revertant form, modified to be
      heat stable
<220> FEATURE:
<221> NAME/KEY: variation
```

```
<222> LOCATION: (267)
<223> OTHER INFORMATION: k = g or t; amino acid 86 = Ala.
<220> FEATURE:
<221> NAME/KEY: variation
<222> LOCATION: (540)
<223> OTHER INFORMATION: n = a or g or c or t/u, unknown, or other.
<220> FEATURE:
<221> NAME/KEY: variation
<222> LOCATION: (1008)
<223> OTHER INFORMATION: y = c or t.
<220> FEATURE:
<221> NAME/KEY: variation
<222> LOCATION: (1197)
<223> OTHER INFORMATION: n = a or g or c or t/u, unknown, or other.
<220> FEATURE:
<221> NAME/KEY: variation
<222> LOCATION: (1368)
<223> OTHER INFORMATION: r = a or g; amino acid 453 = Pro.
<220> FEATURE:
<221> NAME/KEY: variation
<222> LOCATION: (1572)
<223> OTHER INFORMATION: k = g or t.

<400> SEQUENCE: 41 ggaggagat atg cag ttt gca ctt gca ttg gac acg aac tca ggt cct cac        51
          Met Gln Phe Ala Leu Ala Leu Asp Thr Asn Ser Gly Pro His
          1               5                   10 cag ata aga tct tgt gag ggt gat ggg att gac agg ttg gaa aaa tta          99
Gln Ile Arg Ser Cys Glu Gly Asp Gly Ile Asp Arg Leu Glu Lys Leu
 15              20                  25                  30 agt att ggg ggc aga aag cag gag aaa gct ttg aga aat agg tgc ttt         147
Ser Ile Gly Gly Arg Lys Gln Glu Lys Ala Leu Arg Asn Arg Cys Phe
             35                  40                  45 ggt ggt aga gtt gct gca act aca caa tgt att ctt acc tca gat gct         195
Gly Gly Arg Val Ala Ala Thr Thr Gln Cys Ile Leu Thr Ser Asp Ala
         50                  55                  60 tgt cct gaa act ctt cat tct caa aca cag tcc tct agg aaa aat tat         243
Cys Pro Glu Thr Leu His Ser Gln Thr Gln Ser Ser Arg Lys Asn Tyr
 65                  70                  75 gct gat gca aac cgt gta tct gck atc att ttg ggc gga ggc act gga         291
Ala Asp Ala Asn Arg Val Ser Ala Ile Ile Leu Gly Gly Gly Thr Gly
             80                  85                  90 tct cag ctc ttt cct ctg aca agc aca aga gct acg cct gct gta cct         339
Ser Gln Leu Phe Pro Leu Thr Ser Thr Arg Ala Thr Pro Ala Val Pro
 95                 100                 105                 110 gtt gga gga tgt tac agg ctt att gat atc cct atg agt aac tgc ttc         387
Val Gly Gly Cys Tyr Arg Leu Ile Asp Ile Pro Met Ser Asn Cys Phe
                115                 120                 125 aac agt ggt ata aat aag ata ttt gtg atg agt cag ttc aat tct act         435
Asn Ser Gly Ile Asn Lys Ile Phe Val Met Ser Gln Phe Asn Ser Thr
            130                 135                 140 tcg ctt aac cgc cat att cat cgt aca tac ctt gaa ggc ggg atc aac         483
Ser Leu Asn Arg His Ile His Arg Thr Tyr Leu Glu Gly Gly Ile Asn
        145                 150                 155 ttt gct gat gga tct gta cag gta tta gcg gct aca caa atg cct gaa         531
Phe Ala Asp Gly Ser Val Gln Val Leu Ala Ala Thr Gln Met Pro Glu
    160                 165                 170 gag cca gtn gga tgg ttc cag ggt aca gca gac tct atc aga aaa ttt         579
Glu Pro Val Gly Trp Phe Gln Gly Thr Ala Asp Ser Ile Arg Lys Phe
175                 180                 185                 190 atc tgg gta ctc gag gat tat tac agt cac aaa tcc att gac aac att         627
Ile Trp Val Leu Glu Asp Tyr Tyr Ser His Lys Ser Ile Asp Asn Ile
                195                 200                 205 gta atc ttg agt ggc gat cag ctt tat cgg atg aat tac atg gaa ctt         675
Val Ile Leu Ser Gly Asp Gln Leu Tyr Arg Met Asn Tyr Met Glu Leu
            210                 215                 220
```

| | | | | | | | | | | | | | | | |
|---|---|---|---|---|---|---|---|---|---|---|---|---|---|---|---|
| gtg | cag | aaa | cat | gtc | gag | gac | gat | gct | gat | atc | act | ata | tca | tgt | gct | 723 |
| Val | Gln | Lys | His | Val | Glu | Asp | Asp | Ala | Asp | Ile | Thr | Ile | Ser | Cys | Ala | |
| | | 225 | | | | 230 | | | | 235 | | | | | | |

| cct | gtt | gat | gag | agc | cga | gct | tct | aaa | aat | ggg | cta | gtg | aag | att | gat | 771 |
| Pro | Val | Asp | Glu | Ser | Arg | Ala | Ser | Lys | Asn | Gly | Leu | Val | Lys | Ile | Asp | |
| 240 | | | | | 245 | | | | | 250 | | | | | | |

| cat | act | gga | cgt | gta | ctt | caa | ttc | ttt | gaa | aaa | cca | aag | ggt | gct | gat | 819 |
| His | Thr | Gly | Arg | Val | Leu | Gln | Phe | Phe | Glu | Lys | Pro | Lys | Gly | Ala | Asp | |
| 255 | | | | 260 | | | | | 265 | | | | | 270 | | |

| ttg | aat | tct | atg | aga | gtt | gag | acc | aac | ttc | ctg | agc | tat | gct | ata | gat | 867 |
| Leu | Asn | Ser | Met | Arg | Val | Glu | Thr | Asn | Phe | Leu | Ser | Tyr | Ala | Ile | Asp | |
| | | | | 275 | | | | | 280 | | | | | 285 | | |

| gat | gca | cag | aaa | tat | cca | tac | ctt | gca | tca | atg | ggc | att | tat | gtc | ttc | 915 |
| Asp | Ala | Gln | Lys | Tyr | Pro | Tyr | Leu | Ala | Ser | Met | Gly | Ile | Tyr | Val | Phe | |
| | | 290 | | | | | 295 | | | | | 300 | | | | |

| aag | aaa | gat | gca | ctt | tta | gac | ctt | ctc | aag | tca | aaa | tat | act | caa | tta | 963 |
| Lys | Lys | Asp | Ala | Leu | Leu | Asp | Leu | Leu | Lys | Ser | Lys | Tyr | Thr | Gln | Leu | |
| | | | 305 | | | | | 310 | | | | | 315 | | | |

| cat | gac | ttt | gga | tct | gaa | atc | ctc | cca | aga | gct | gta | cta | gat | tay | agt | 1011 |
| His | Asp | Phe | Gly | Ser | Glu | Ile | Leu | Pro | Arg | Ala | Val | Leu | Asp | Tyr | Ser | |
| 320 | | | | | 325 | | | | | 330 | | | | | | |

| gtg | cag | gca | tgc | att | ttt | acg | ggc | tat | tgg | gag | gat | gtt | gga | aca | atc | 1059 |
| Val | Gln | Ala | Cys | Ile | Phe | Thr | Gly | Tyr | Trp | Glu | Asp | Val | Gly | Thr | Ile | |
| 335 | | | | 340 | | | | | 345 | | | | | 350 | | |

| aaa | tca | ttc | ttt | gat | gca | aac | ttg | gcc | ctc | act | gag | cag | cct | tcc | aag | 1107 |
| Lys | Ser | Phe | Phe | Asp | Ala | Asn | Leu | Ala | Leu | Thr | Glu | Gln | Pro | Ser | Lys | |
| | | | | 355 | | | | | 360 | | | | | 365 | | |

| ttt | gat | ttt | tac | gat | cca | aaa | aca | cct | ttc | ttc | act | gca | ccc | cga | tgc | 1155 |
| Phe | Asp | Phe | Tyr | Asp | Pro | Lys | Thr | Pro | Phe | Phe | Thr | Ala | Pro | Arg | Cys | |
| | | 370 | | | | | 375 | | | | | 380 | | | | |

| ttg | cct | ccg | acg | caa | ttg | gac | aag | tgc | aag | atg | aaa | tat | gtn | ttt | atc | 1203 |
| Leu | Pro | Pro | Thr | Gln | Leu | Asp | Lys | Cys | Lys | Met | Lys | Tyr | Val | Phe | Ile | |
| | | 385 | | | | | 390 | | | | | 395 | | | | |

| tca | gat | ggt | tgc | tta | ctg | aga | gaa | tgc | aac | atc | gag | cat | tct | gtg | att | 1251 |
| Ser | Asp | Gly | Cys | Leu | Leu | Arg | Glu | Cys | Asn | Ile | Glu | His | Ser | Val | Ile | |
| 400 | | | | | 405 | | | | | 410 | | | | | | |

| gga | gtc | tgc | tca | cgt | gtc | agc | tct | gga | tgt | gaa | ctc | aag | gac | tcc | gtg | 1299 |
| Gly | Val | Cys | Ser | Arg | Val | Ser | Ser | Gly | Cys | Glu | Leu | Lys | Asp | Ser | Val | |
| 415 | | | | 420 | | | | | 425 | | | | | 430 | | |

| atg | atg | gga | gcg | gac | atc | tat | gaa | act | gaa | gaa | gaa | gct | tca | aag | cta | 1347 |
| Met | Met | Gly | Ala | Asp | Ile | Tyr | Glu | Thr | Glu | Glu | Glu | Ala | Ser | Lys | Leu | |
| | | | | 435 | | | | | 440 | | | | | 445 | | |

| ctg | tta | gct | ggg | aag | gtc | ccr | gtt | gga | ata | gga | agg | aac | aca | aag | ata | 1395 |
| Leu | Leu | Ala | Gly | Lys | Val | Pro | Val | Gly | Ile | Gly | Arg | Asn | Thr | Lys | Ile | |
| | | | 450 | | | | | 455 | | | | | 460 | | | |

| agg | aac | tgt | atc | att | gac | atg | aat | gct | agg | att | ggg | aag | aac | gtg | gtg | 1443 |
| Arg | Asn | Cys | Ile | Ile | Asp | Met | Asn | Ala | Arg | Ile | Gly | Lys | Asn | Val | Val | |
| | | 465 | | | | | 470 | | | | | 475 | | | | |

| atc | aca | aac | agt | aag | ggc | atc | caa | gag | gct | gat | cac | ccg | gaa | gaa | ggg | 1491 |
| Ile | Thr | Asn | Ser | Lys | Gly | Ile | Gln | Glu | Ala | Asp | His | Pro | Glu | Glu | Gly | |
| | | 480 | | | | | 485 | | | | | 490 | | | | |

| tac | tac | ata | agg | tct | gga | atc | gtg | gtg | atc | ctg | aag | aat | gca | acc | atc | 1539 |
| Tyr | Tyr | Ile | Arg | Ser | Gly | Ile | Val | Val | Ile | Leu | Lys | Asn | Ala | Thr | Ile | |
| 495 | | | | 500 | | | | | 505 | | | | | 510 | | |

| aac | gat | ggg | tct | gtc | ata | tagatcggct gcgtktgcg | | | | | | | | | | 1576 |
| Asn | Asp | Gly | Ser | Val | Ile | | | | | | | | | | | |
| | | | | 515 | | | | | | | | | | | | |

<210> SEQ ID NO 42
<211> LENGTH: 516

```
<212> TYPE: PRT
<213> ORGANISM: Zea mays

<400> SEQUENCE: 42

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
                165                 170                 175

Val Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Tyr Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Val Phe Ile Ser Asp
385                 390                 395                 400
```

```
Gly Cys Leu Leu Arg Glu Cys Asn Ile Glu His Ser Val Ile Gly Val
                405                 410                 415
Cys Ser Arg Val Ser Ser Gly Cys Glu Leu Lys Asp Ser Val Met Met
            420                 425                 430
Gly Ala Asp Ile Tyr Glu Thr Glu Glu Ala Ser Lys Leu Leu Leu
        435                 440                 445
Ala Gly Lys Val Pro Val Gly Ile Gly Arg Asn Thr Lys Ile Arg Asn
    450                 455                 460
Cys Ile Ile Asp Met Asn Ala Arg Ile Gly Lys Asn Val Val Ile Thr
465                 470                 475                 480
Asn Ser Lys Gly Ile Gln Glu Ala Asp His Pro Glu Glu Gly Tyr Tyr
                485                 490                 495
Ile Arg Ser Gly Ile Val Val Ile Leu Lys Asn Ala Thr Ile Asn Asp
                500                 505                 510
Gly Ser Val Ile
            515

<210> SEQ ID NO 43
<211> LENGTH: 521
<212> TYPE: PRT
<213> ORGANISM: Solanum tuberosum

<400> SEQUENCE: 43

Met Ala Ala Ser Ile Gly Ala Leu Lys Ser Ser Pro Ser Ser Asn Asn
1               5                   10                  15
Cys Ile Asn Glu Arg Arg Asn Asp Ser Thr Arg Ala Val Ser Ser Arg
            20                  25                  30
Asn Leu Ser Phe Ser Ser Ser His Leu Ala Gly Asp Lys Leu Met Pro
        35                  40                  45
Val Ser Ser Leu Arg Ser Gln Gly Val Arg Phe Asn Val Arg Arg Ser
    50                  55                  60
Pro Met Ile Val Ser Pro Lys Ala Val Ser Asp Ser Gln Asn Ser Gln
65                  70                  75                  80
Thr Cys Leu Asp Pro Asp Ala Ser Arg Ser Val Leu Gly Ile Ile Leu
                85                  90                  95
Gly Gly Gly Ala Gly Thr Arg Leu Tyr Pro Leu Thr Lys Lys Arg Ala
            100                 105                 110
Lys Pro Ala Val Pro Leu Gly Ala Asn Tyr Arg Leu Ile Asp Ile Pro
        115                 120                 125
Val Ser Asn Cys Leu Asn Ser Asn Ile Ser Lys Ile Tyr Val Leu Thr
    130                 135                 140
Gln Phe Asn Ser Ala Ser Leu Asn Arg His Leu Ser Arg Ala Tyr Ala
145                 150                 155                 160
Ser Asn Met Gly Gly Tyr Lys Asn Glu Gly Phe Val Glu Val Leu Ala
                165                 170                 175
Ala Gln Gln Ser Pro Glu Asn Pro Asp Trp Phe Gln Gly Thr Ala Asp
            180                 185                 190
Ala Val Arg Gln Tyr Leu Trp Leu Phe Glu Glu His Thr Val Leu Glu
        195                 200                 205
Tyr Leu Ile Leu Ala Gly Asp His Leu Tyr Arg Met Asp Tyr Glu Lys
    210                 215                 220
Phe Ile Gln Ala His Arg Glu Thr Asp Ala Asp Ile Thr Val Ala Ala
225                 230                 235                 240
Leu Pro Met Asp Glu Lys Arg Ala Thr Ala Phe Gly Leu Met Lys Ile
                245                 250                 255
```

```
Asp Glu Glu Gly Arg Ile Ile Glu Phe Ala Glu Lys Pro Gln Gly Glu
            260                 265                 270

Gln Leu Gln Ala Met Lys Val Asp Thr Thr Ile Leu Gly Leu Asp Asp
        275                 280                 285

Lys Arg Ala Lys Glu Met Pro Phe Ile Ala Ser Met Gly Ile Tyr Val
    290                 295                 300

Ile Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Leu Gly
                325                 330                 335

Met Arg Val Gln Ala Tyr Leu Tyr Asp Gly Tyr Trp Glu Asp Ile Gly
            340                 345                 350

Thr Ile Glu Ala Phe Tyr Asn Ala Asn Leu Gly Ile Thr Lys Lys Pro
        355                 360                 365

Val Pro Asp Phe Ser Phe Tyr Asp Arg Ser Ala Pro Ile Tyr Thr Gln
    370                 375                 380

Pro Arg Tyr Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
                405                 410                 415

Ser Val Val Gly Leu Arg Ser Cys Ile Ser Glu Gly Ala Ile Ile Glu
            420                 425                 430

Asp Ser Leu Leu Met Gly Ala Asp Tyr Tyr Glu Thr Asp Ala Asp Arg
        435                 440                 445

Lys Leu Leu Ala Ala Lys Gly Ser Val Pro Ile Gly Ile Gly Lys Asn
    450                 455                 460

Cys His Ile Lys Arg Ala Ile Ile Asp Lys Asn Ala Arg Ile Gly Asp
465                 470                 475                 480

Asn Val Lys Ile Ile Asn Lys Asp Asn Val Gln Glu Ala Ala Arg Glu
                485                 490                 495

Thr Asp Gly Tyr Phe Ile Lys Ser Gly Ile Val Thr Val Ile Lys Asp
            500                 505                 510

Ala Leu Ile Pro Ser Gly Ile Ile Ile
        515                 520

<210> SEQ ID NO 44
<211> LENGTH: 521
<212> TYPE: PRT
<213> ORGANISM: Artificial sequence
<220> FEATURE:
<223> OTHER INFORMATION: consensus sequence of SEQ ID NO:2 and SEQ ID
      NO:43.
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(24)
<223> OTHER INFORMATION: Xaa can be any naturally occurring amino acid
<220> FEATURE:
<221> NAME/KEY: misc_feature
<222> LOCATION: (26)..(31)
<223> OTHER INFORMATION: Xaa can be any naturally occurring amino acid
<220> FEATURE:
```

```
<221> NAME/KEY: misc_feature
<222> LOCATION: (33)..(36)
<223> OTHER INFORMATION: Xaa can be any naturally occurring amino acid
<220> FEATURE:
<221> NAME/KEY: misc_feature
<222> LOCATION: (39)..(77)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (270)..(270)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
```

```
<221> NAME/KEY: misc_feature
<222> LOCATION: (415)..(415)
<223> OTHER INFORMATION: Xaa can be any naturally occurring amino acid
<220> FEATURE:
<221> NAME/KEY: misc_feature
<222> LOCATION: (453)..(453)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (465)..(466)
<223> OTHER INFORMATION: Xaa can be any naturally occurring amino acid
<220> FEATURE:
<221> NAME/KEY: misc_feature
<222> LOCATION: (487)..(487)
<223> OTHER INFORMATION: Xaa can be any naturally occurring amino acid
<220> FEATURE:
<221> NAME/KEY: misc_feature
<222> LOCATION: (495)..(495)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
<222> LOCATION: (519)..(519)
<223> OTHER INFORMATION: Xaa can be any naturally occurring amino acid

<400> SEQUENCE: 44

Xaa Xaa Xaa Xaa Xaa Xaa Xaa Leu Xaa Xaa Ala Xaa Ala Ser Xaa Xaa
1               5                   10                  15

Xaa Xaa Xaa Xaa Xaa Xaa Xaa Xaa Ala Xaa Xaa Xaa Xaa Xaa Xaa Lys
            20                  25                  30

Xaa Xaa Xaa Xaa Ala Ala Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Asn Xaa Xaa
65                  70                  75                  80

Thr Xaa Leu Xaa Pro Xaa Ala Xaa Xaa Ser Val Leu Gly Ile Ile Leu
            85                  90                  95

Gly Gly Gly Ala Gly Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
            115                 120                 125

Val Ser Asn Cys Leu Asn Ser Asn Ile Ser Lys Ile Tyr Val Leu Thr
130                 135                 140

Gln Phe Asn Ser Ala Ser Leu Asn Arg His Leu Ser Arg Ala Tyr Ala
145                 150                 155                 160

Ser Asn Ile Gly Gly Tyr Lys Asn Glu Gly Phe Val Glu Val Leu Ala
                165                 170                 175

Ala Gln Gln Ser Pro Asp Asn Pro Xaa Trp Phe Gln Gly Thr Ala Asp
            180                 185                 190

Ala Val Arg Gln Tyr Leu Trp Leu Phe Glu Glu His Xaa Val Leu Glu
            195                 200                 205

Phe Leu Ile Leu Ala Gly Asp His Leu Tyr Arg Met Asp Tyr Glu Lys
            210                 215                 220

Phe Ile Gln Ala His Arg Glu Thr Xaa Ala Asp Ile Thr Val Ala Ala
225                 230                 235                 240

Leu Pro Met Asp Glu Lys Arg Ala Thr Ala Phe Gly Leu Met Lys Ile
```

-continued

```
                        245                 250                 255
Asp Glu Glu Gly Arg Ile Ile Glu Phe Ala Glu Lys Pro Xaa Gly Glu
            260                 265                 270

Gln Leu Xaa Ala Met Xaa Val Asp Thr Thr Ile Leu Gly Leu Asp Asp
            275                 280                 285

Xaa Arg Ala Lys Glu Met Pro Phe Ile Ala Ser Met Gly Ile Tyr Val
            290                 295                 300

Xaa Ser Lys Asp Val Met Leu Asn Leu Leu Arg Asp Xaa Phe Pro Xaa
305                 310                 315                 320

Ala Asn Asp Phe Gly Ser Glu Val Ile Pro Gly Ala Thr Ser Ile Gly
            325                 330                 335

Xaa Arg Val Gln Ala Tyr Leu Tyr Asp Gly Tyr Trp Glu Asp Ile Gly
            340                 345                 350

Thr Ile Xaa Ala Phe Tyr Asn Ala Asn Leu Gly Ile Thr Lys Lys Pro
            355                 360                 365

Ile Pro Asp Phe Ser Phe Tyr Asp Arg Xaa Ala Pro Ile Tyr Thr Gln
            370                 375                 380

Pro Arg His Leu Pro Pro Ser Lys Met Leu Asp Ala Asp Val Thr Asp
385                 390                 395                 400

Ser Val Ile Gly Glu Gly Cys Val Ile Lys Asn Cys Lys Ile Xaa His
            405                 410                 415

Ser Val Val Gly Leu Arg Ser Cys Ile Ser Glu Gly Ala Ile Ile Glu
            420                 425                 430

Asp Ser Leu Leu Met Gly Ala Asp Tyr Tyr Glu Thr Asp Ala Asp Lys
            435                 440                 445

Lys Leu Leu Ala Xaa Lys Gly Xaa Ile Pro Ile Gly Ile Gly Lys Asn
            450                 455                 460

Xaa Xaa Ile Lys Arg Ala Ile Ile Asp Lys Asn Ala Arg Ile Gly Asp
465                 470                 475                 480

Asn Val Lys Ile Ile Asn Xaa Asp Asn Val Gln Glu Ala Ala Xaa Glu
            485                 490                 495

Thr Asp Gly Tyr Phe Ile Lys Xaa Gly Ile Val Thr Val Ile Lys Asp
            500                 505                 510

Ala Leu Ile Pro Ser Gly Xaa Ile Ile
            515                 520
```